(12) United States Patent
Egawa et al.

(10) Patent No.: US 7,758,972 B2
(45) Date of Patent: Jul. 20, 2010

(54) STILBENE DERIVATIVE, LIGHT EMITTING ELEMENT, LIGHT EMITTING DEVICE, AND ELECTRONIC APPLIANCE

(75) Inventors: Masakazu Egawa, Tochigi (JP); Sachiko Kawakami, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 480 days.

(21) Appl. No.: 11/856,160

(22) Filed: Sep. 17, 2007

(65) Prior Publication Data

US 2008/0145700 A1 Jun. 19, 2008

(30) Foreign Application Priority Data

Sep. 26, 2006 (JP) .............................. 2006-261336

(51) Int. Cl.
| | |
|---|---|
| C07D 209/86 | (2006.01) |
| C07D 403/10 | (2006.01) |
| H01J 1/62 | (2006.01) |
| C09K 11/06 | (2006.01) |
| H01L 51/50 | (2006.01) |
| H01L 51/54 | (2006.01) |

(52) U.S. Cl. ...................... 428/690; 428/917; 313/504; 313/506; 548/440; 257/40

(58) Field of Classification Search ........................ None
See application file for complete search history.

(56) References Cited

U.S. PATENT DOCUMENTS 6,562,982 B1 * 5/2003 Hu et al. ...................... 548/440
6,670,054 B1 * 12/2003 Hu et al. ...................... 428/690

FOREIGN PATENT DOCUMENTS

| JP | 2004-75580 | | 3/2004 |
|---|---|---|---|
| JP | 2004-196716 | * | 7/2004 |
| WO | WO 2007/058503 A1 | * | 5/2007 |

OTHER PUBLICATIONS

Cha et al., Synthetic Metals, vol. 143, (2004), pp. 97-101.*

* cited by examiner

*Primary Examiner*—Dawn L Garrett
(74) *Attorney, Agent, or Firm*—Husch Blackwell Sanders LLP

(57) ABSTRACT

An object is to provide a novel substance which exhibits blue light emission with excellent color purity, and to provide a light emitting element and a light emitting device using the novel substance. A stilbene derivative represented by the general formula (G1) is provided. Note that in the general formula (G1), each of $A^1$ and $B^1$ represents any one of structures represented by the following general formulae (G1-1) to (G1-4). In addition, in each of the general formulae (G1-1) to (G1-4), each of $R^1$ to $R^{24}$ represents any one of hydrogen and an alkyl group having 1 to 4 carbon atoms. Such a stilbene derivative can exhibit blue light emission with excellent color purity.

(G1)

-continued
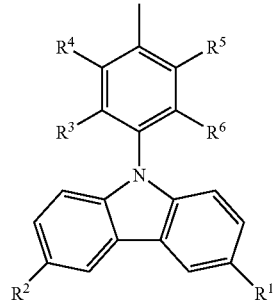
(G1-1)
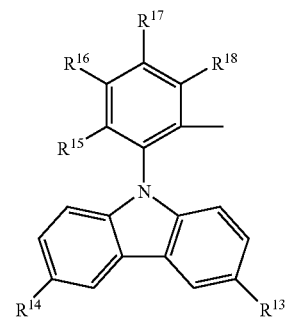
(G1-3)
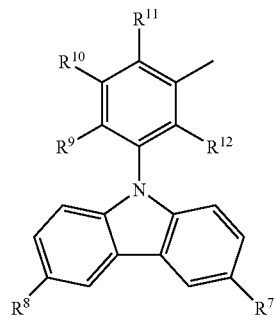
(G1-2)
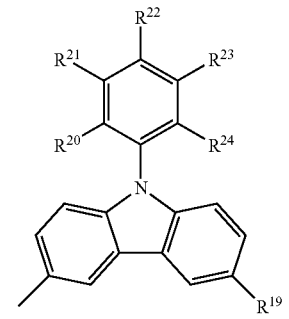
(G1-4)
11 Claims, 30 Drawing Sheets

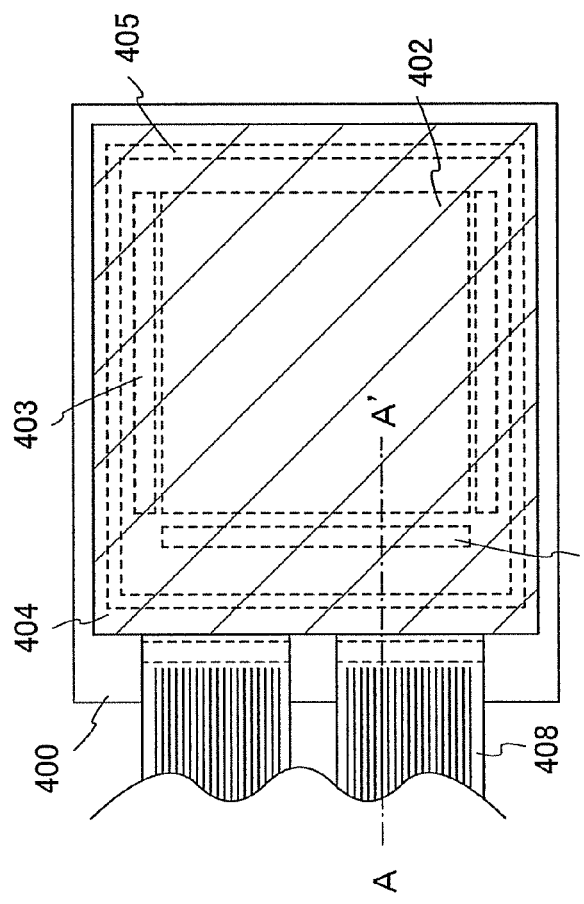
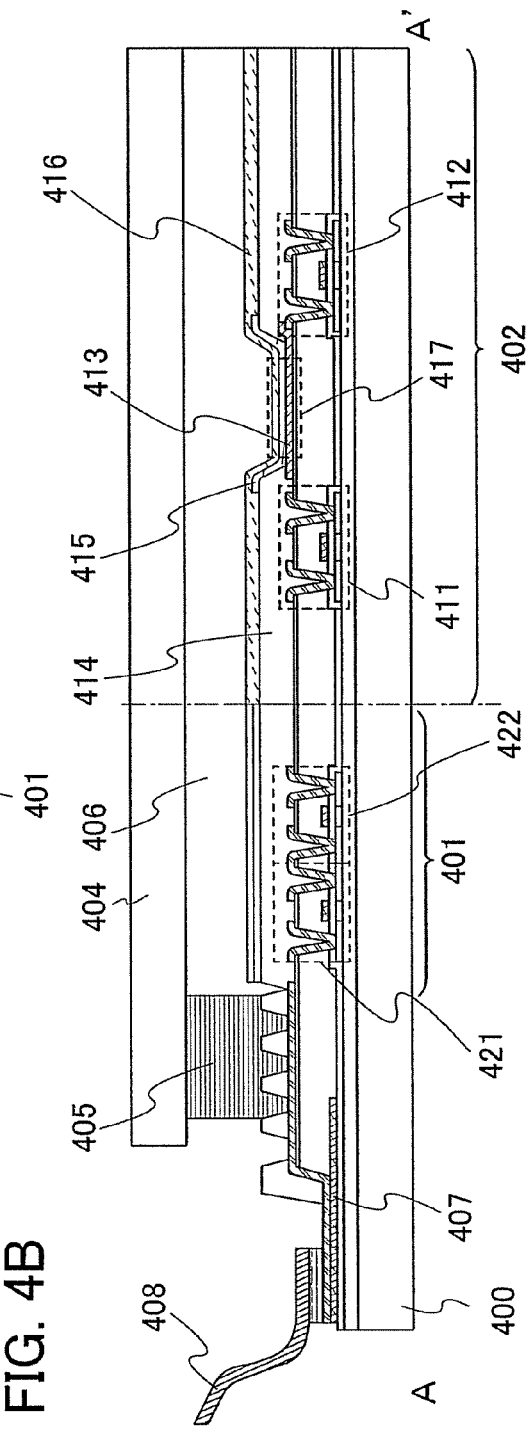
FIG. 4A
FIG. 4B

STILBENE DERIVATIVE, LIGHT EMITTING ELEMENT, LIGHT EMITTING DEVICE, AND ELECTRONIC APPLIANCE

BACKGROUND OF THE INVENTION

1. Field of the Invention

The present invention relates to a stilbene derivative, a light emitting element using the stilbene derivative, and a light emitting device and an electronic appliance having the stilbene derivative or the light emitting element.

2. Description of the Related Art

A light emitting element which has characteristics such as thinness, lightweight, and rapid response is expected to be applied to flat panel displays of the next generation. In addition, it is said that a light emitting device in which light emitting elements are arranged in matrix is superior to a conventional liquid crystal display device, especially in wide viewing angle and visibility.

A light emitting element has a structure in which a layer including a light emitting substance is interposed between a pair of electrodes (an anode and a cathode). It is said that, in such a light emitting element, when voltage is applied between the electrodes, holes injected from the anode and electrons injected from the cathode are recombined in the layer including a light emitting substance, so that molecular excitons of the light emitting substance are formed, and light is emitted when the molecular excitons return to the ground state.

Accordingly, emission wavelength of a light emitting element is determined by a band gap of a light emitting substance contained in the light emitting element. Therefore, various emission colors can be obtained by devising a structure of the light emitting substance. A full-color light emitting device can be realized, by forming light emitting elements capable of emitting red light, blue light, and green light, which are the three primary colors of light, and using the light emitting elements.

However, there has been a problem such that it is difficult to realize a light emitting element having high reliability and excellent color purity. As a result of recent development of materials, high reliability and excellent color purity of light emitting elements of green and red have been achieved. On the other hand, excellent color purity and high reliability of a light emitting element of blue has not been sufficiently realized, and many researches thereof are carried out (for example, Reference 1: Japanese Published Patent Application No. 2004-75580).

SUMMARY OF THE INVENTION

The present invention has been made in view of the foregoing problems. It is an object of the present invention to provide a novel substance which exhibits blue light emission with excellent color purity, and to provide a light emitting element, a light emitting device, and an electronic appliance using the novel substance.

One aspect of the present invention is a stilbene derivative represented by a general formula (G1).

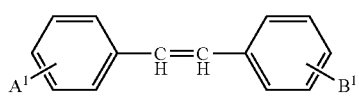
(G1)

In the general formula (G1), each of $A^1$ and $B^1$ represents any one of structures represented by following general formulae (G1-1) to (G1-4). In addition, in each of the general formulae (G1-1) to (G1-4), each of $R^1$ to $R^{24}$ represents any one of hydrogen and an alkyl group having 1 to 4 carbon atoms.

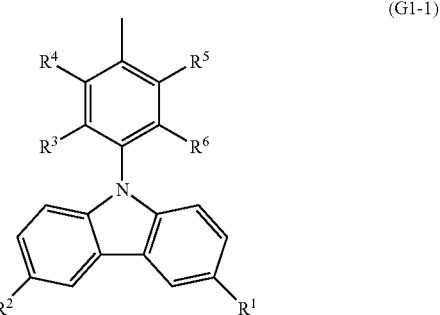
(G1-1)

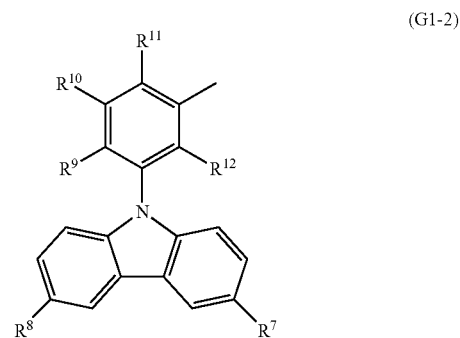
(G1-2)

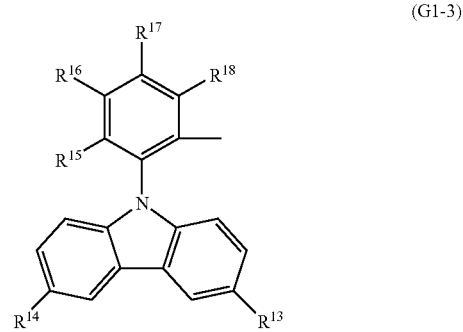
(G1-3)

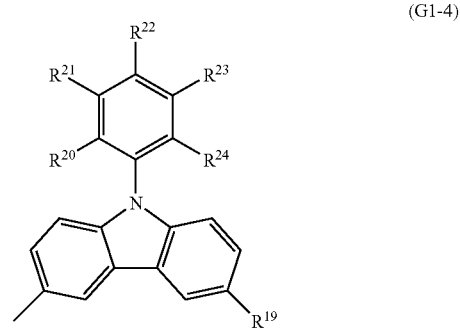
(G1-4)

Note that, as to a substituent which represents any one of hydrogen and an alkyl group having 1 to 4 carbon atoms, such as $R^1$ to $R^{24}$, any one of structural formulae (G1'-1) to (G1'-9) can be used, for example.

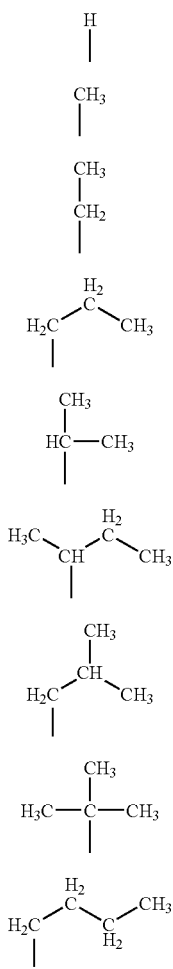

(G1'-1)
(G1'-2)
(G1'-3)
(G1'-4)
(G1'-5)
(G1'-6)
(G1'-7)
(G1'-8)
(G1'-9)

One aspect of the present invention is a stilbene derivative which is represented by the foregoing general formula (G1) and which has $A^1$ and $B^1$ having the same structure.

One aspect of the present invention is a stilbene derivative represented by a general formula (G2).

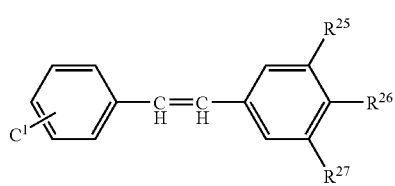

(G2)

In the general formula (G2), $C^1$ represents any one of structures represented by the foregoing general formulae (G1-1) to (G1-4), and each of $R^{25}$ to $R^{27}$ represents any one of hydrogen and an alkyl group having 1 to 4 carbon atoms. Note that, as to the foregoing substituent which represents any one of hydrogen and an alkyl group having 1 to 4 carbon atoms, such as $R^{25}$ to $R^{27}$, any one of the foregoing structural formulae (G1'-1) to (G1'-9) can be used, for example.

One aspect of the present invention is a stilbene derivative represented by a general formula (G3).

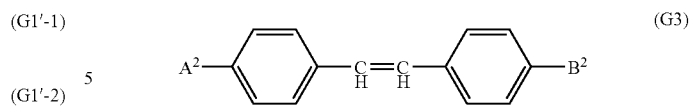

(G3)

In the general formula (G3), each of $A^2$ and $B^2$ represents any one of structures represented by the foregoing general formulae (G1-1) to (G1-4).

One aspect of the present invention is a stilbene derivative which is represented by the foregoing general formula (G3) and which includes $A^2$ and $B^2$ having the same structure.

Note that, although the general formula (G3) shows a structure in which the 4-position and 4'-position of stilbene are substituted by $A^2$ and $B^2$, respectively; a position which is substituted by any one of the foregoing general formulae (G1-1) to (G1-4) is not limited, as shown in the general formula (G1). For example, the 3-position and 4'-position of stilbene may be substituted by any one of the foregoing general formulae (G1-1) to (G1-4).

One aspect of the present invention is a stilbene derivative represented by a general formula (G4).

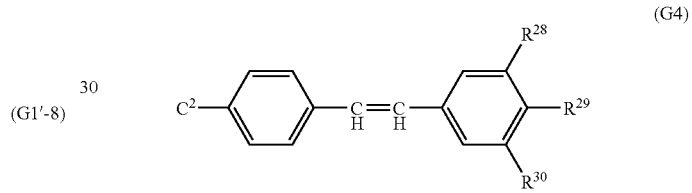

(G4)

In the general formula (G4), $C^2$ represents any one of structures represented by the foregoing general formulae (G1-1) to (G1-4), and each of $R^{28}$ to $R^{30}$ represents any one of hydrogen and an alkyl group having 1 to 4 carbon atoms. Note that, as to the foregoing substituent which represents any one of hydrogen and an alkyl group having 1 to 4 carbon atoms, such as $R^{28}$ to $R^{30}$, any one of the foregoing structural formulae (G1'-1) to (G1'-9) can be used, for example.

Note that, although the general formula (G4) shows a structure in which the 4-position of stilbene is substituted by $C^2$, a position which is substituted by any one of the foregoing general formulae (G1-1) to (G1-4) is not limited, as shown in the general formula (G2).

One aspect of the present invention is a stilbene derivative represented by a general formula (G5).

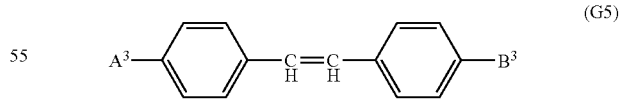

(G5)

In the general formula (G5), each of $A^3$ and $B^3$ represents a structure represented by a following general formula (G2-1) or (G2-2). In each of the general formulae (G2-1) and (G2-2), each of $R^{31}$ to $R^{33}$ represents any one of hydrogen and an alkyl group having 1 to 4 carbon atoms. Note that, as to the foregoing substituent which represents any one of hydrogen and an alkyl group having 1 to 4 carbon atoms, such as $R^{31}$ to $R^{33}$, any one of the foregoing structural formulae (G1'-1) to (G1'-9) can be used, for example.

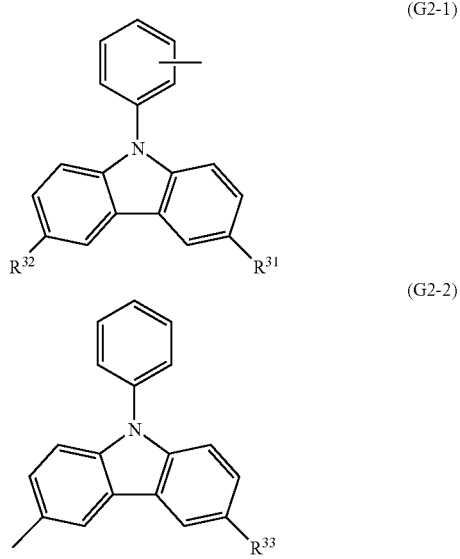

(G2-1)

(G2-2)

One aspect of the present invention is a stilbene derivative which is represented by the foregoing general formula (G5) and which has $A^3$ and $B^3$ having the same structure.

One aspect of the present invention is a stilbene derivative represented by a general formula (G6).

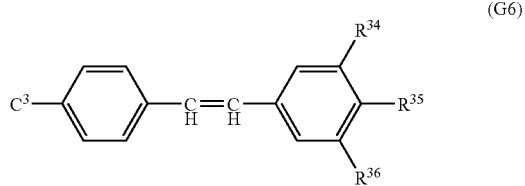

(G6)

In the general formula (G6), $C^3$ represents any one of structures represented by the foregoing general formulae (G2-1) and (G2-2), and each of $R^{34}$ to $R^{36}$ represents any one of hydrogen and an alkyl group having 1 to 4 carbon atoms. Note that, as to the foregoing substituent which represents any one of hydrogen and an alkyl group having 1 to 4 carbon atoms, such as $R^{34}$ to $R^{36}$, any one of the foregoing structural formulae (G1'-1) to (G1'-9) can be used, for example.

Note that a stilbene derivative of the present invention includes geometric isomers: a cis form and a trans form. Both the cis form and the trans form are included in the present invention; however, the trans form is preferable from the point of vies of stability One aspect of the present invention is a light emitting element which includes any of the foregoing stilbene derivatives between a pair of electrodes.

Another aspect of the present invention is a light emitting element which includes a light emitting layer between a pair of electrodes, in which the light emitting layer contains any of the foregoing stilbene derivatives. Note that, since a stilbene derivative of the present invention exhibits blue light emission with excellent color purity, it is preferable that the stilbene derivative be used mainly as a guest material and make the light emitting layer with another host material. Needless to say, the light emitting layer may be formed of only a stilbene derivative of the present invention. Further, a stilbene derivative of the present invention can be used as a host material and is also preferable as a host material for a blue light emitting material.

Yet another aspect of the present invention is a light emitting device and an electronic appliance which include the foregoing light emitting element.

By the present invention, a stilbene derivative which exhibits blue light emission with excellent color purity can be obtained. Further, by forming a light emitting element using the stilbene derivative, a light emitting element and a light emitting device capable of emitting blue light with excellent color purity can be provided. Further, a light emitting device and an electronic appliance capable of showing an image superior in color can be provided.

BRIEF DESCRIPTION OF THE DRAWINGS

FIGS. 4A and 4B are views of a light emitting device using a light emitting element of the present invention;

DETAILED DESCRIPTION OF THE INVENTION

Figure 1:
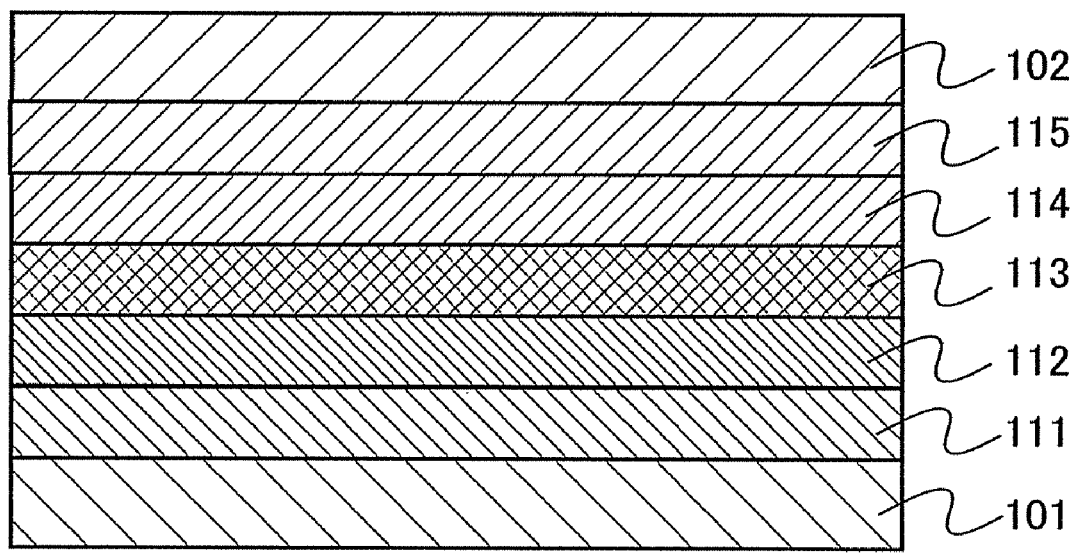
FIG. 1 shows an element structure of a light emitting element of the present invention.

Hereinafter, one mode of the present invention is described. The present invention can be carried out in many different modes. It is easily understood by those skilled in the art that modes and details herein disclosed can be modified in various ways without departing from the purpose and the scope of the present invention. Accordingly, the present invention should not be interpreted as being limited to the embodiment modes and embodiments.

Embodiment Mode 1

One aspect of the present invention is a stilbene derivative represented by any one of following structural formulae (1) to (107). Note that a stilbene derivative of the present invention is not limited to the following structural formulae.

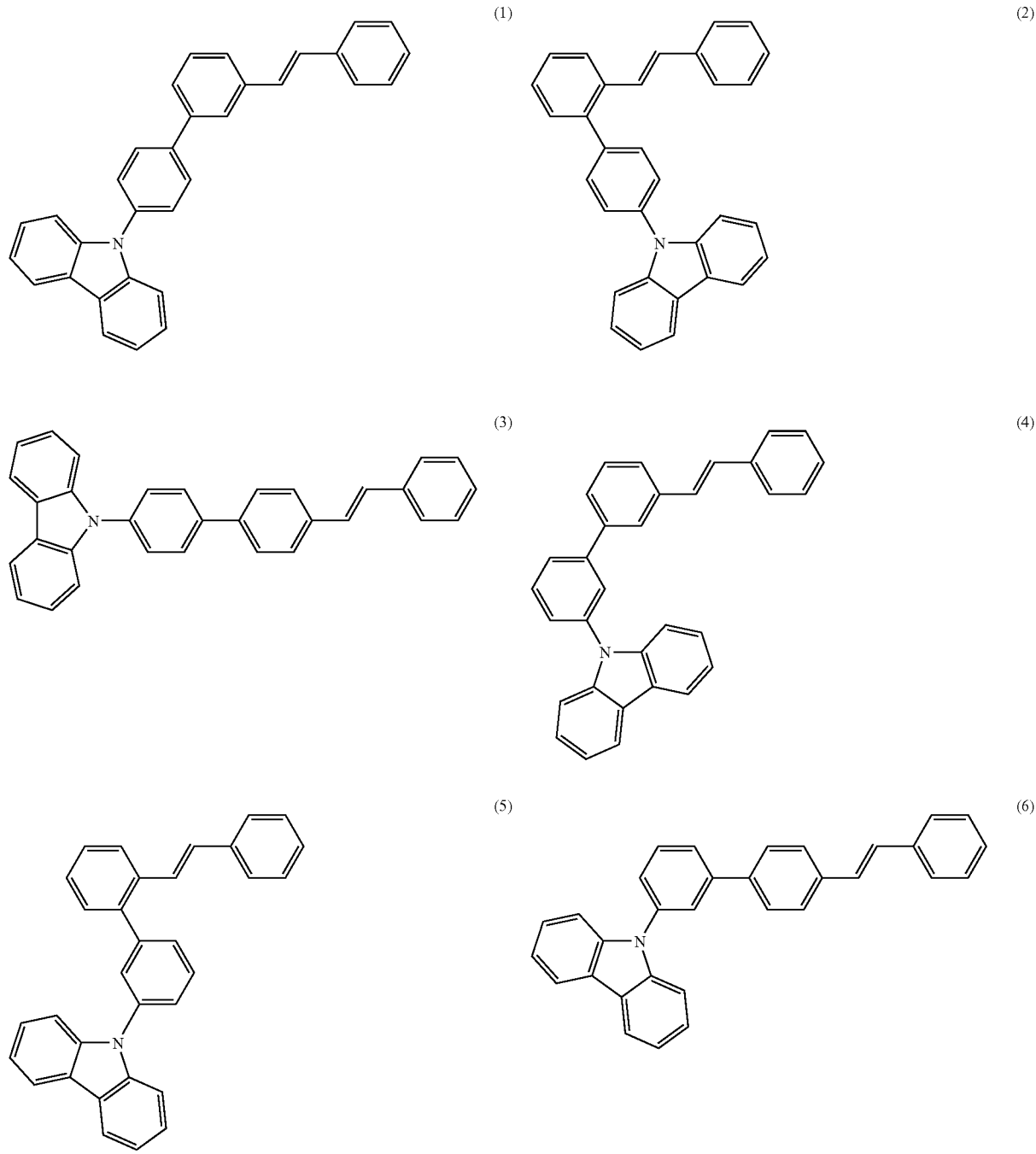

-continued
(7)
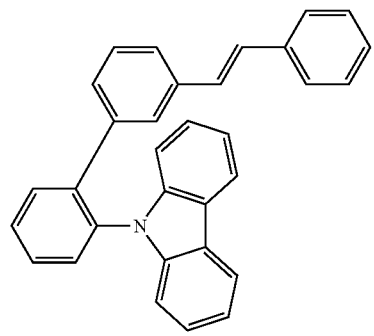
(8)
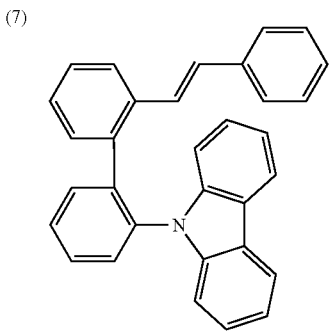
(9)
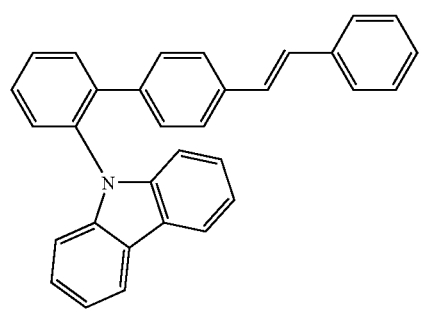
(10)
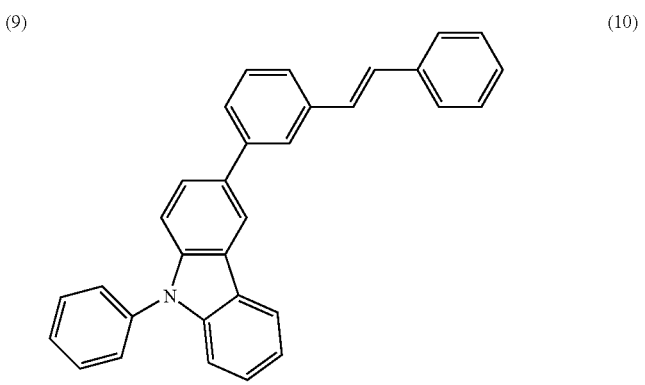
(11)
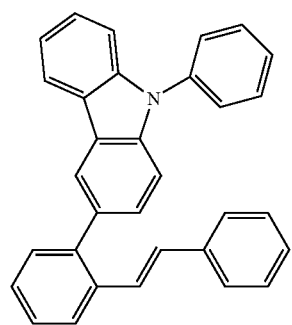
(12)
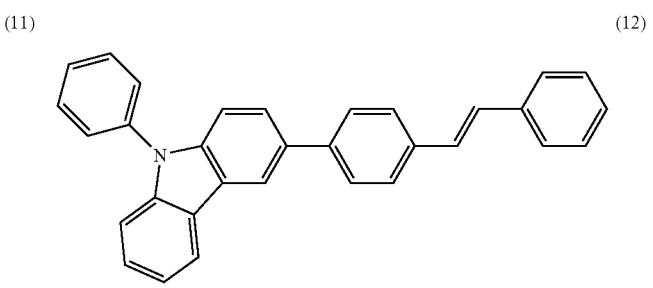
(13)
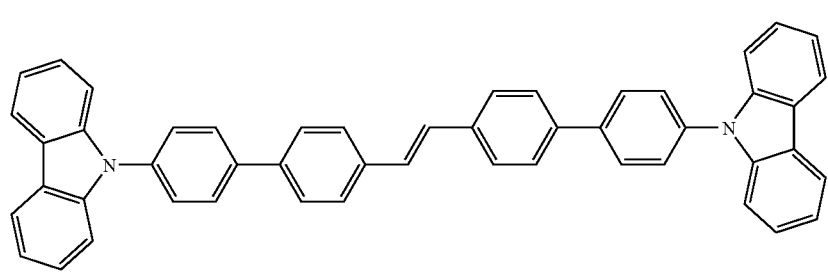

-continued
(14)
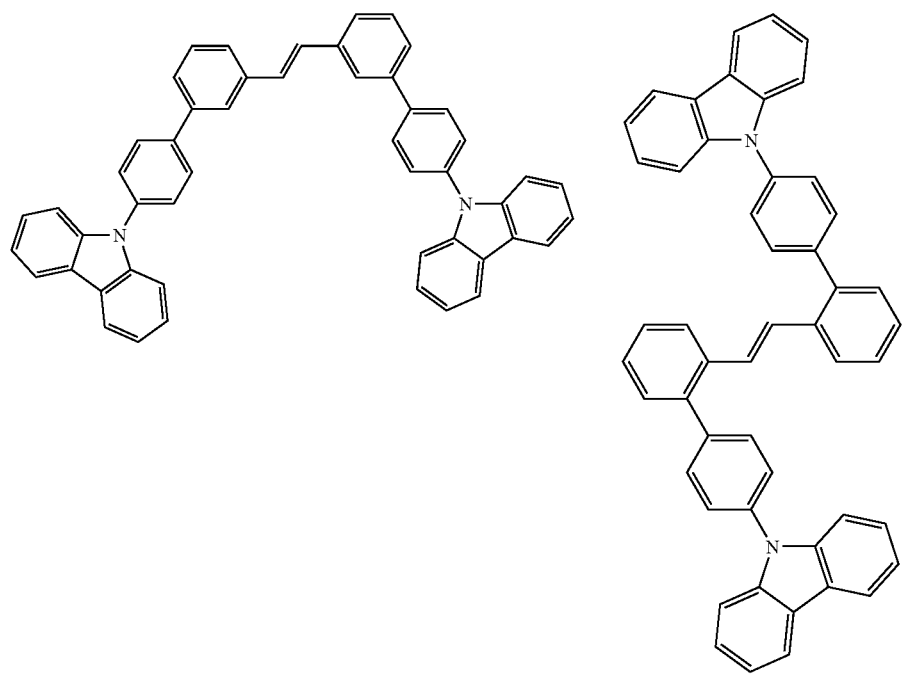
(15)
(16)
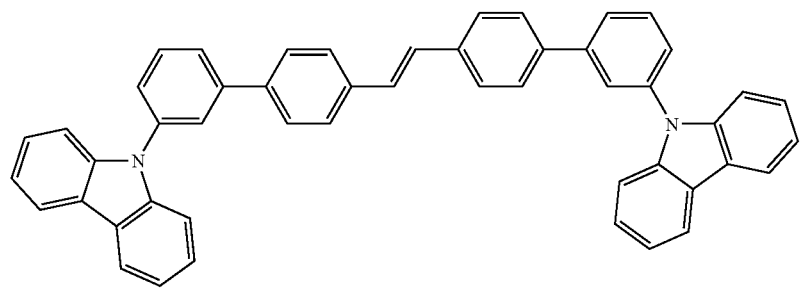
(17)
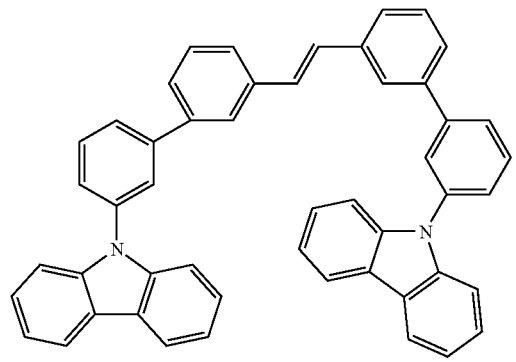
(18)
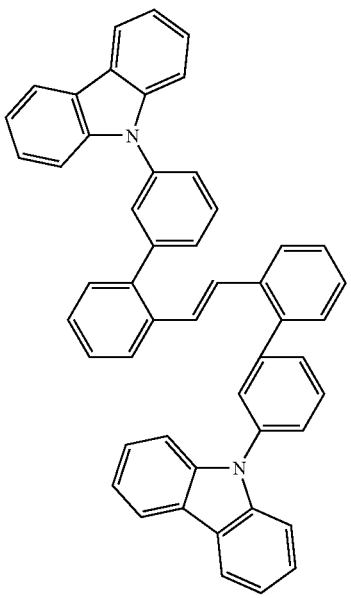

-continued
(19)
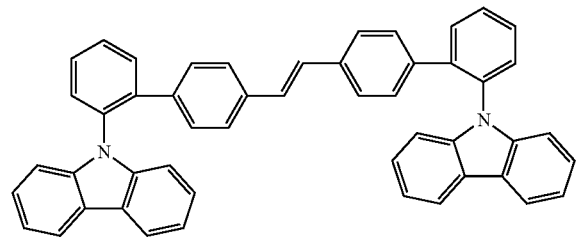
(20)
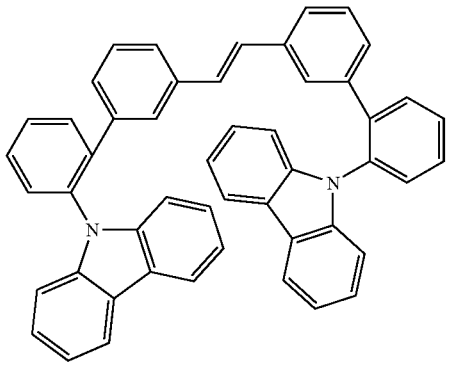
(21)
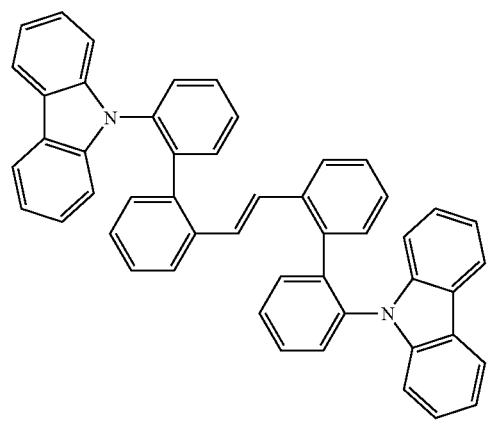
(22)
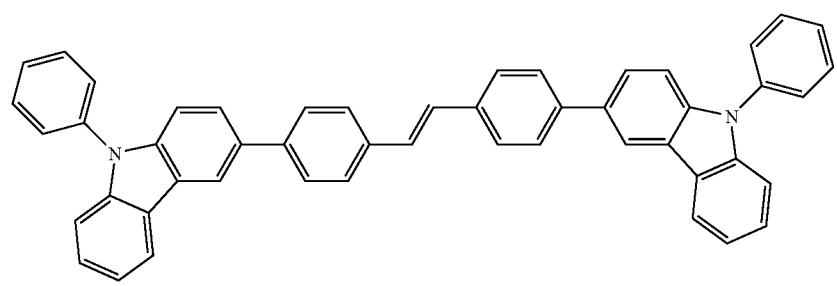

(23)
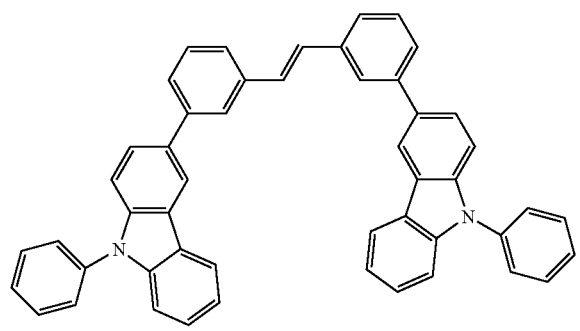
(24)
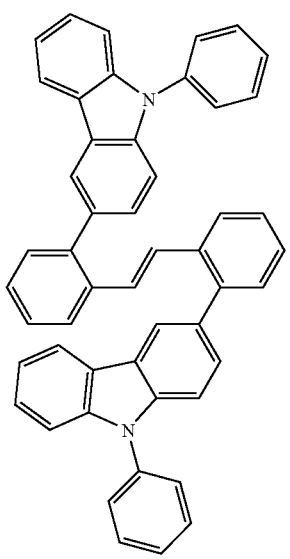
(25)
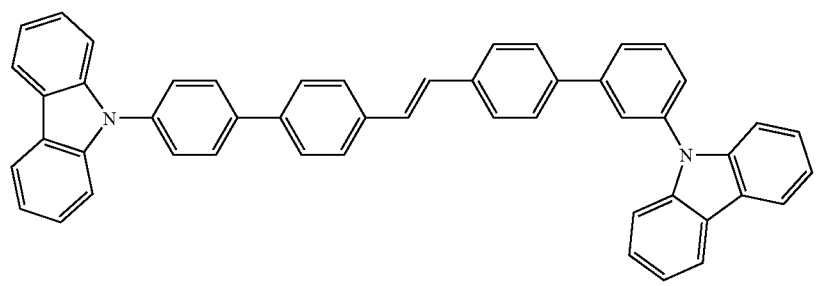
(26)
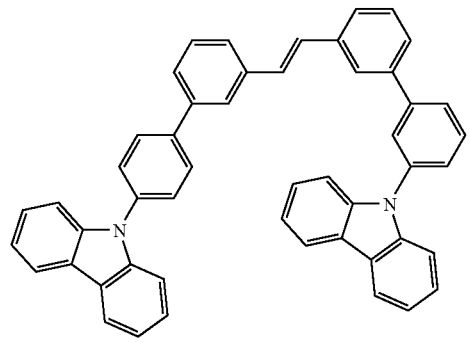
(27)
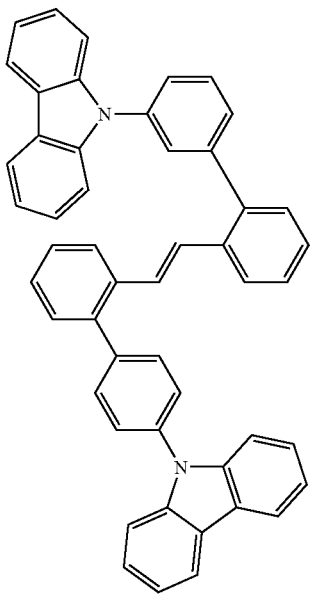

-continued
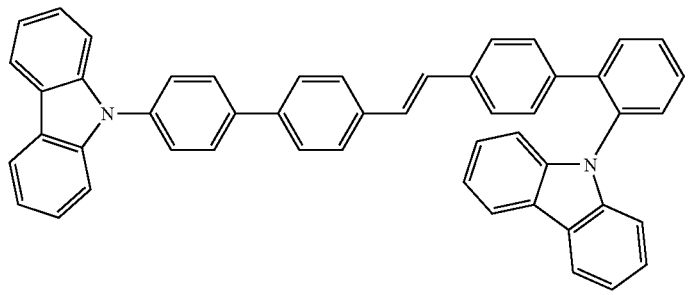
(28)
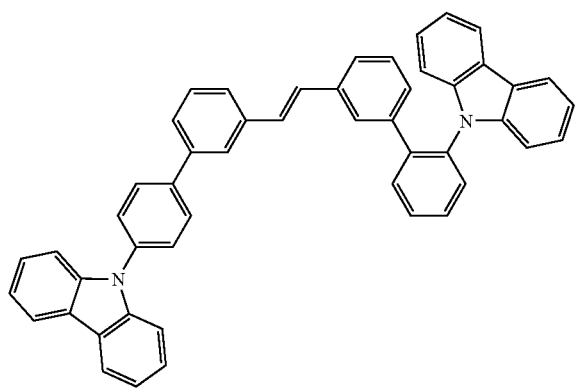
(29)
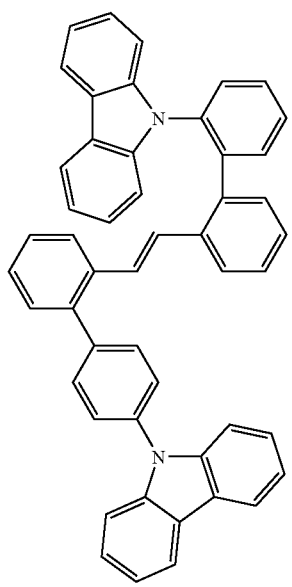
(30)
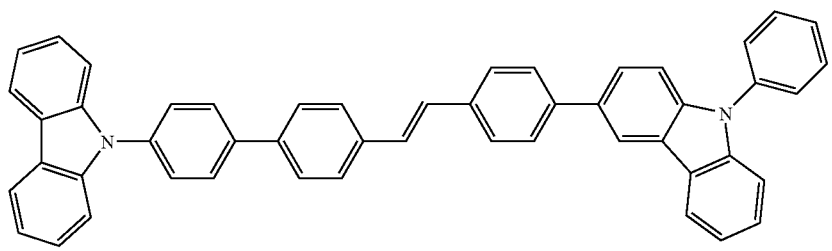
(31)

-continued
(32)
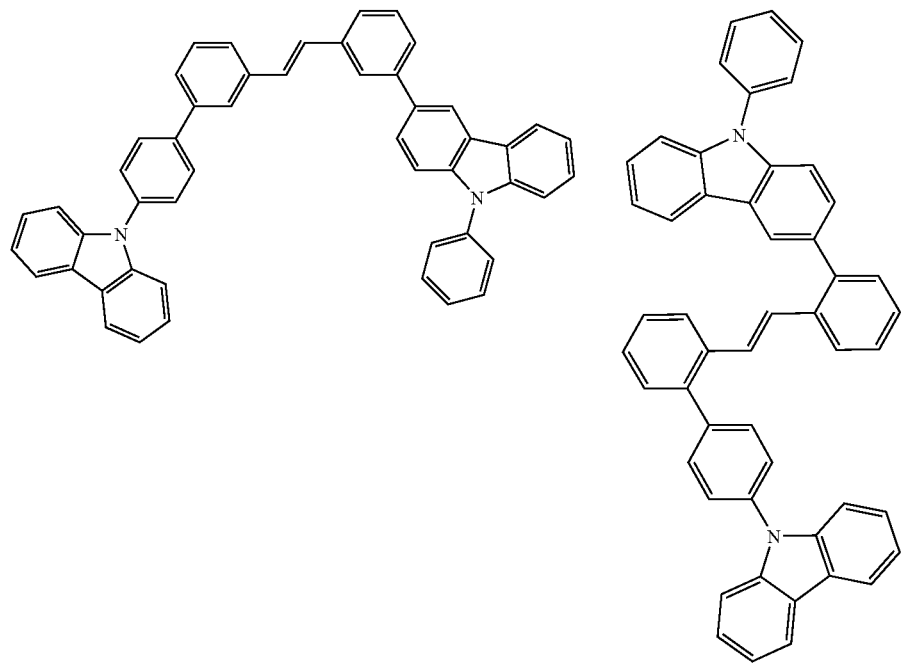
(33)
(34)
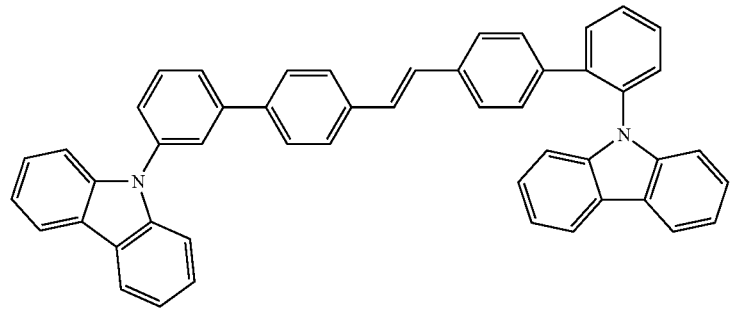
(35)
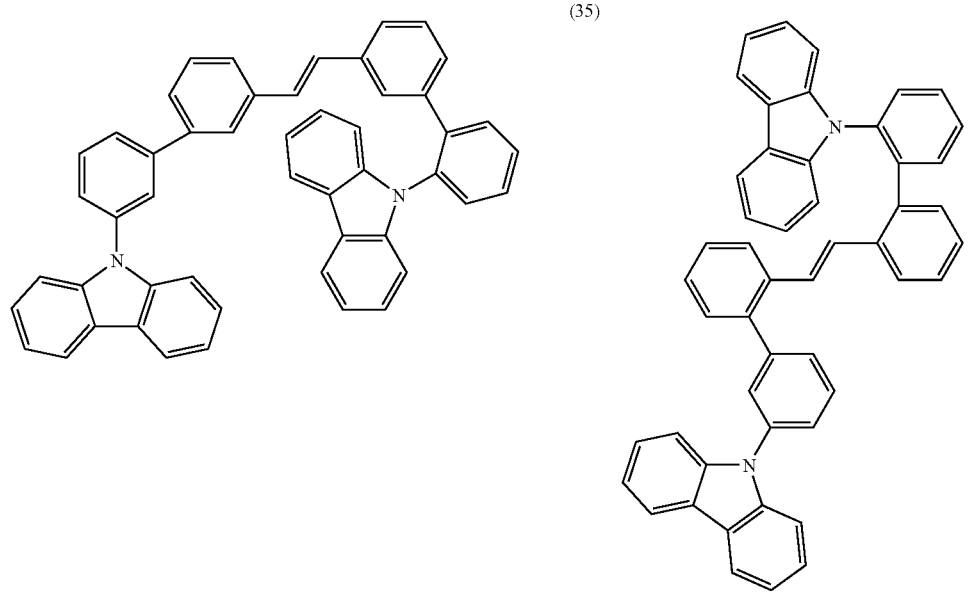
(36)

-continued
(37)
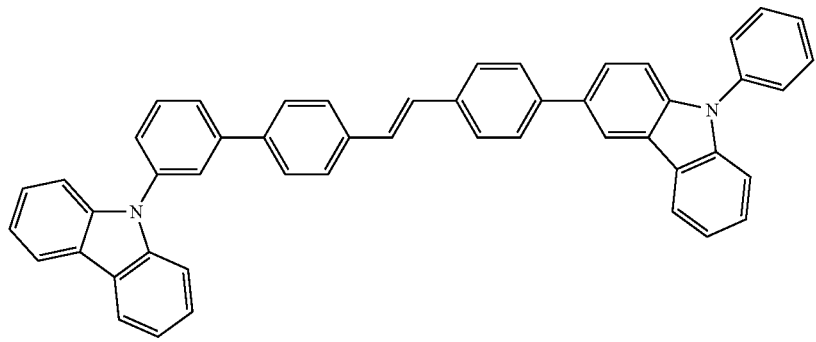
(38)
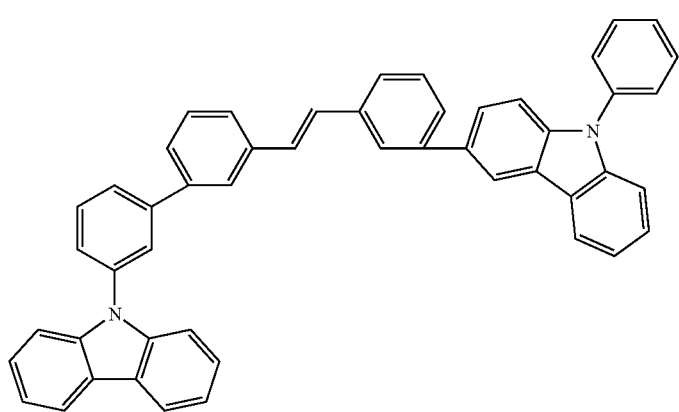
(39)
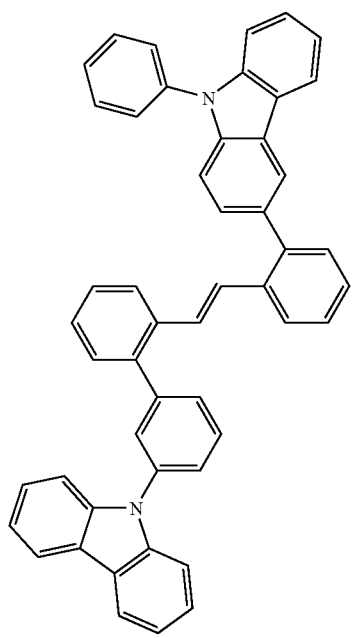
(40)
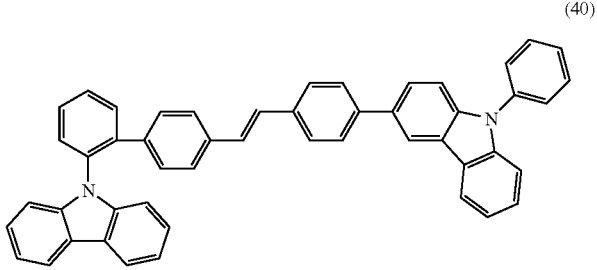

-continued
(41)
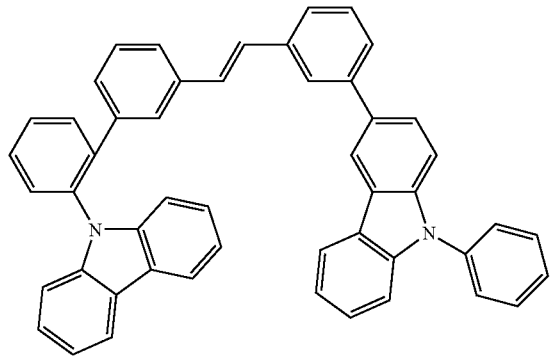
(42)
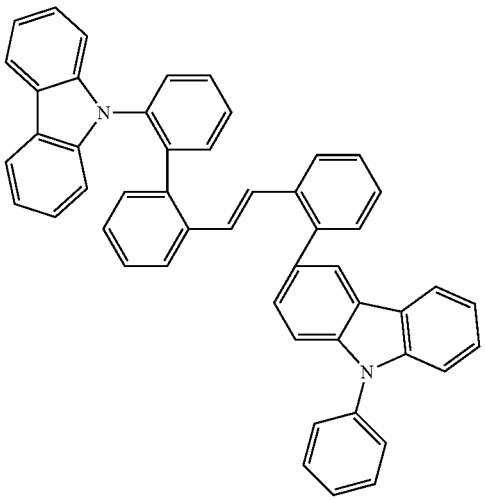
(43)
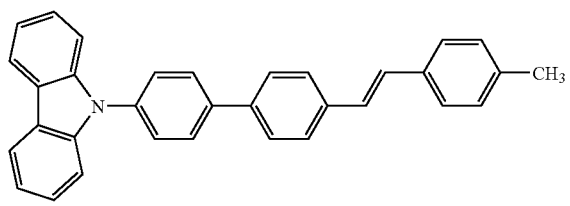
(44)
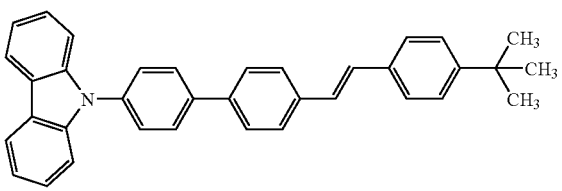
(45)
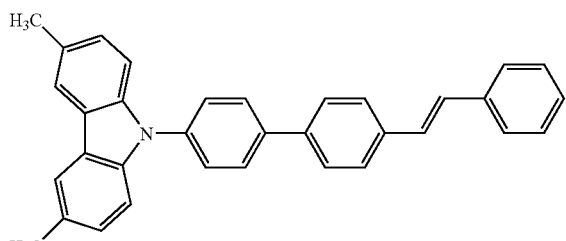
(46)
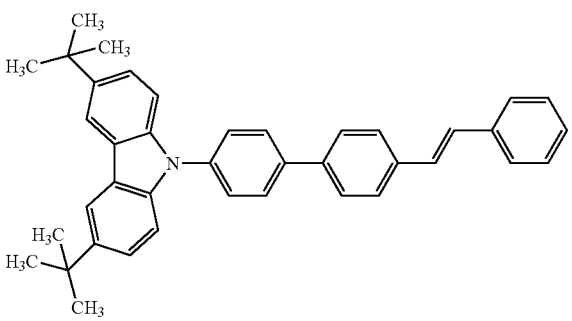
(47)
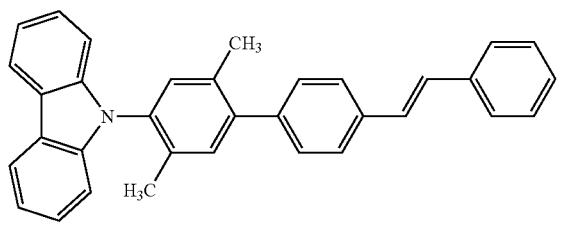
(48)
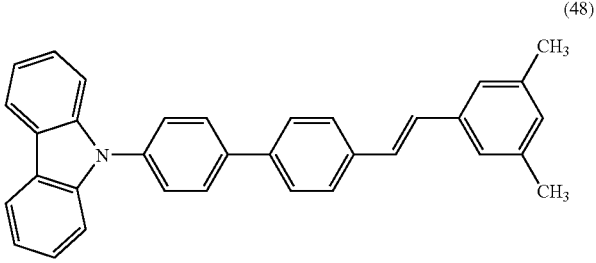

-continued
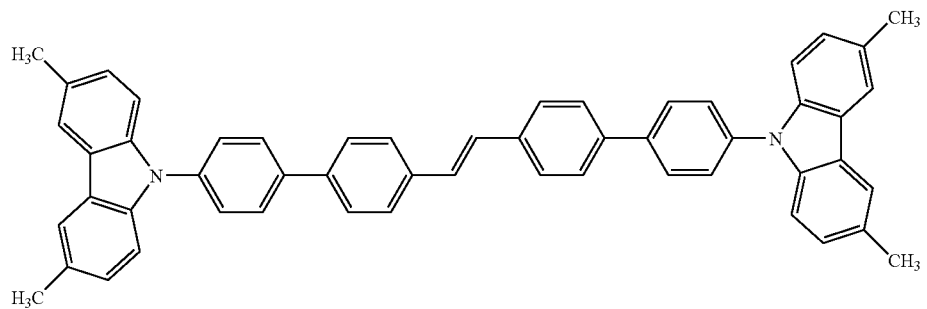
(49)
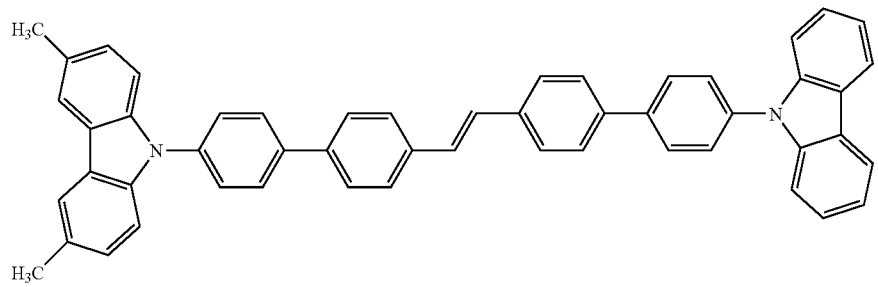
(50)
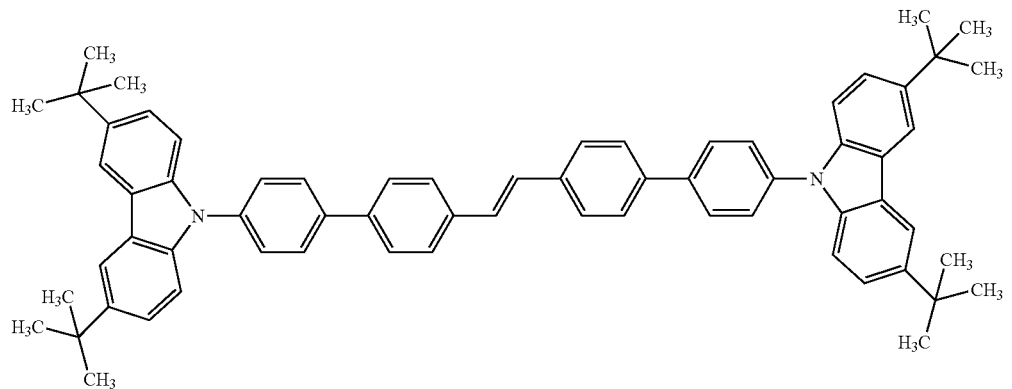
(51)
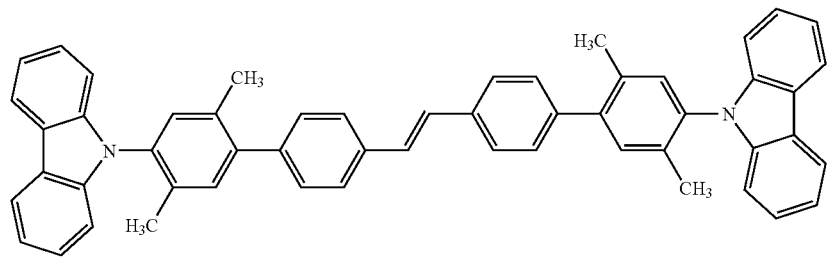
(52)
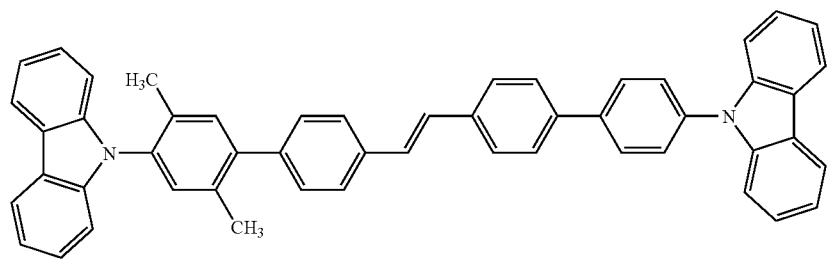
(53)

-continued
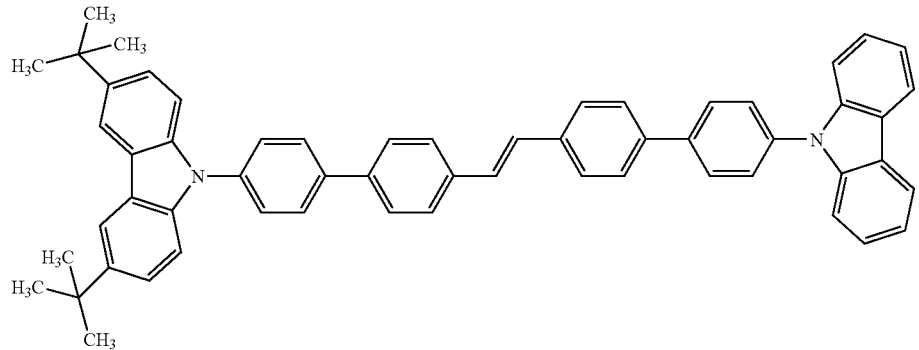
(54)
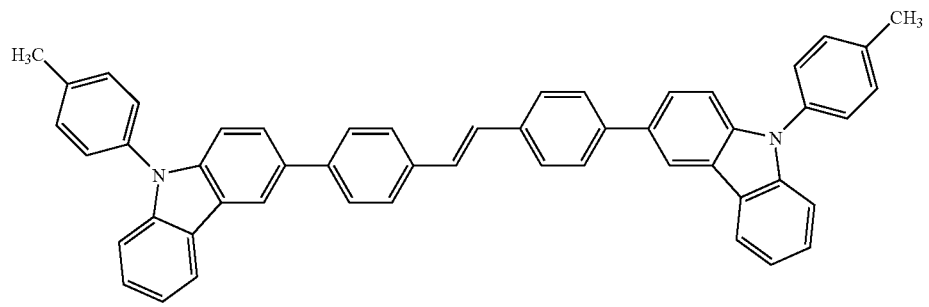
(55)
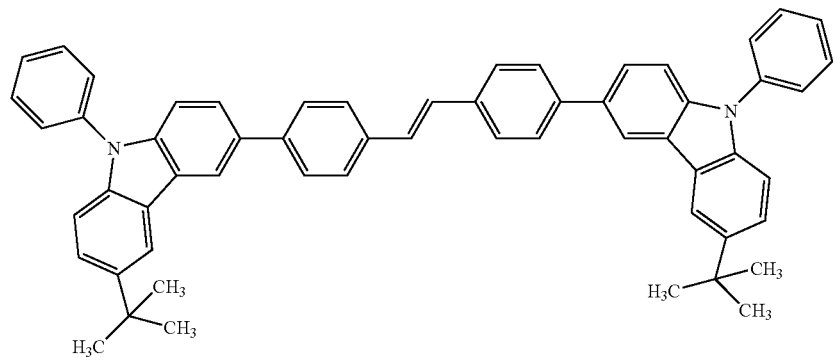
(56)
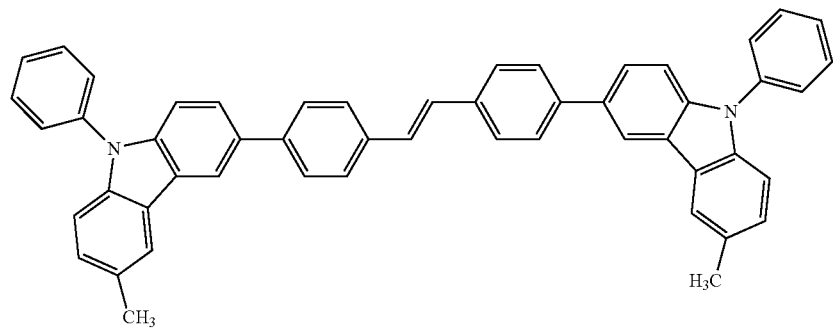
(57)
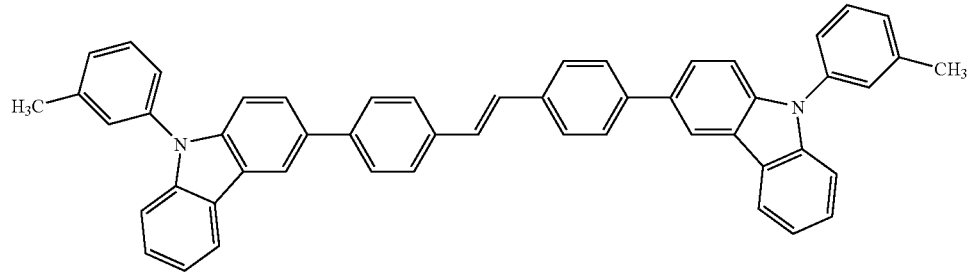
(58)

-continued
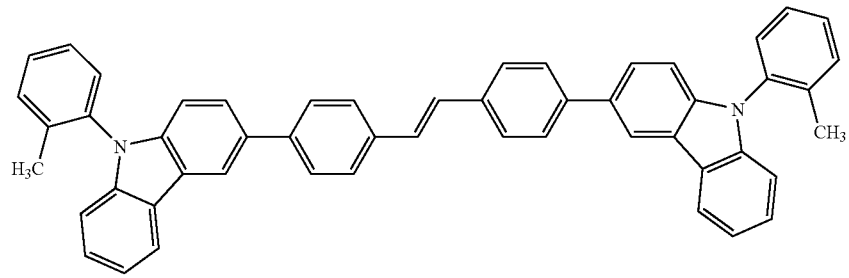
(59)
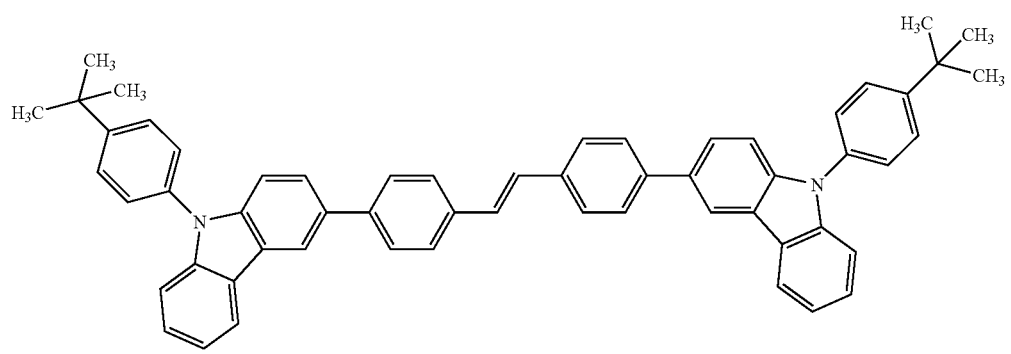
(60)
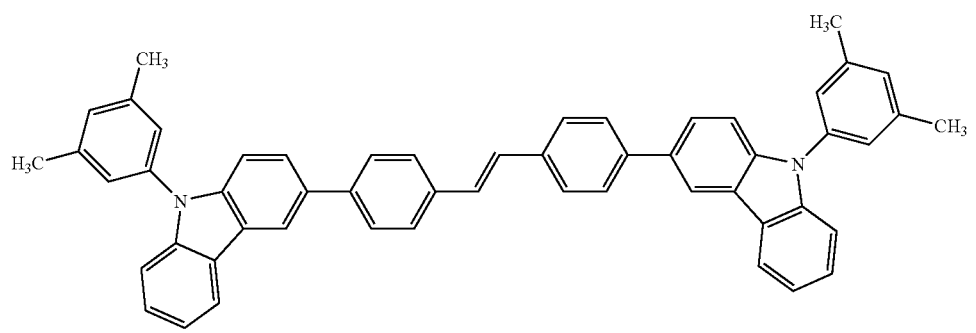
(61)
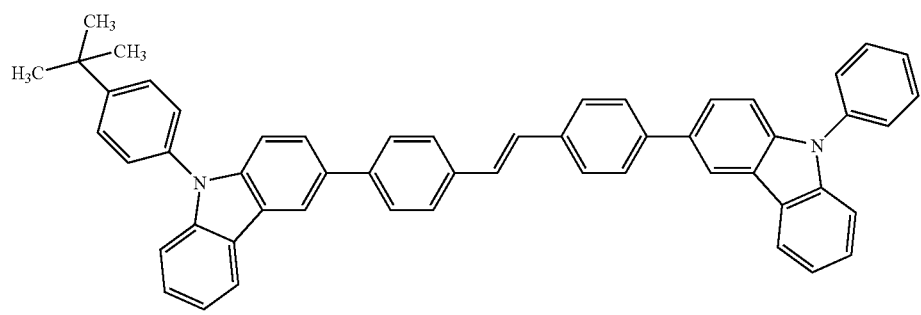
(62)
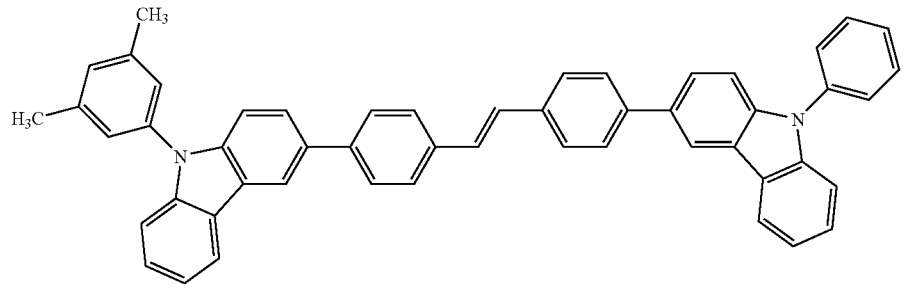
(63)

-continued
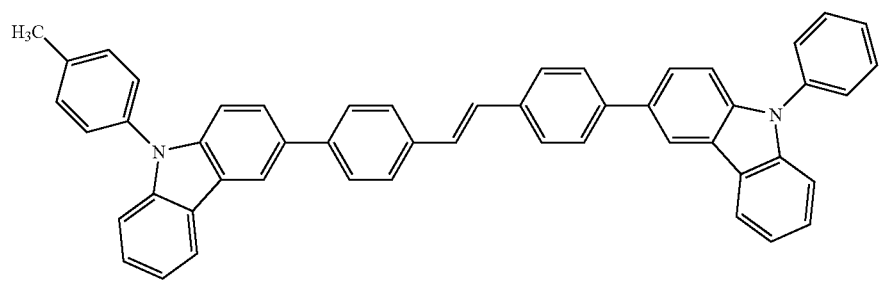
(64)
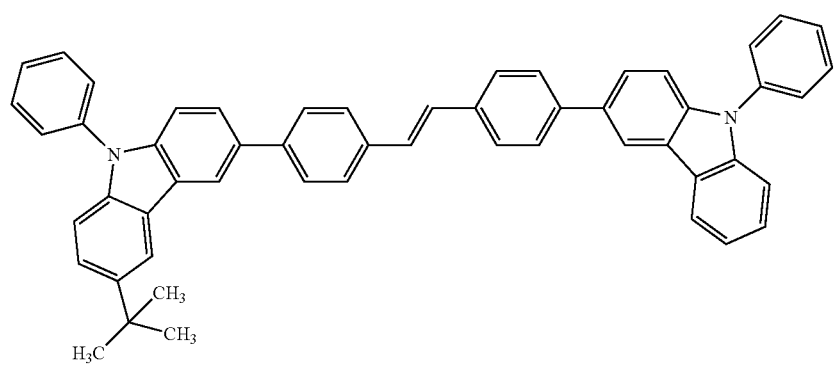
(65)
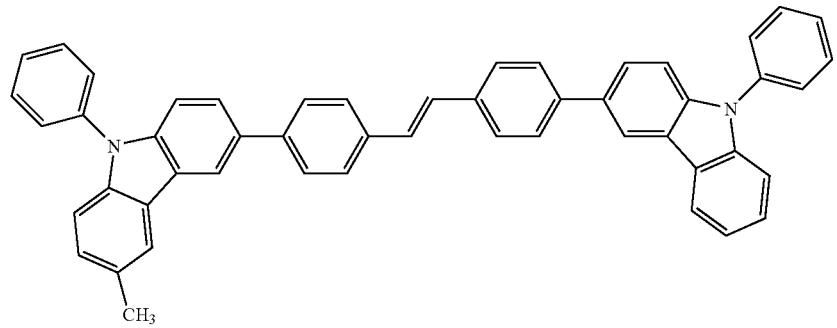
(66)
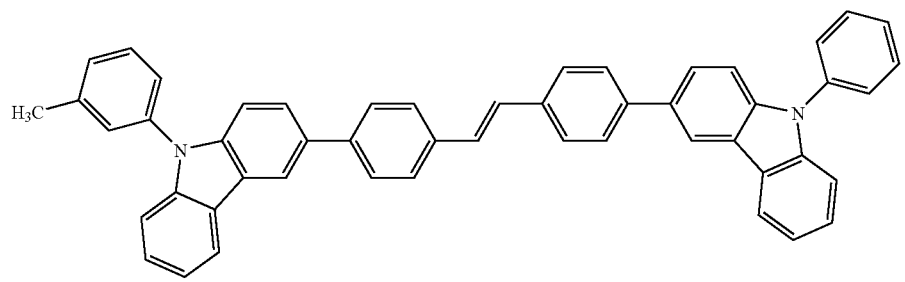
(67)
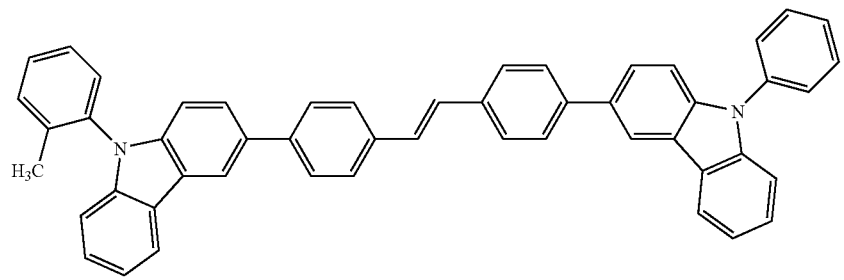
(68)

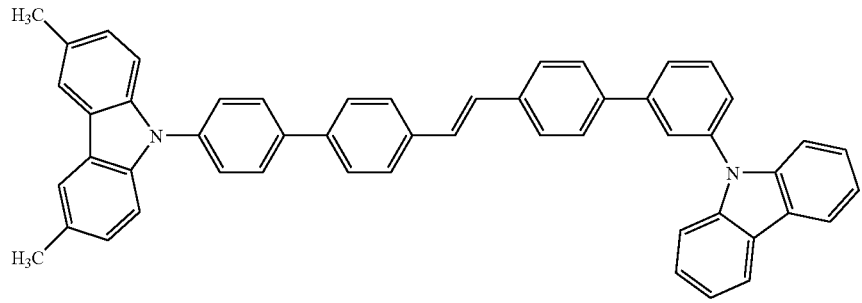
(69)
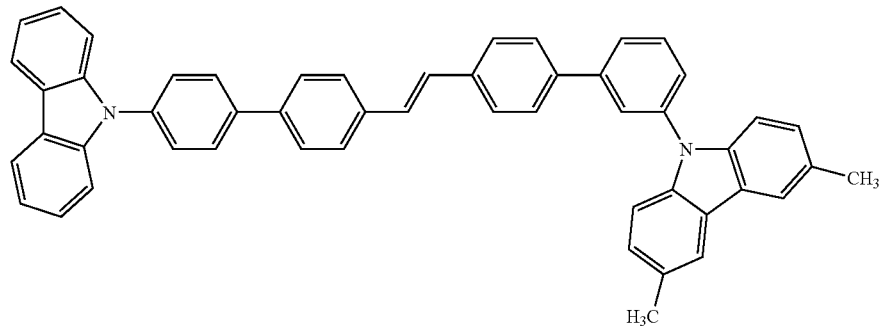
(70)
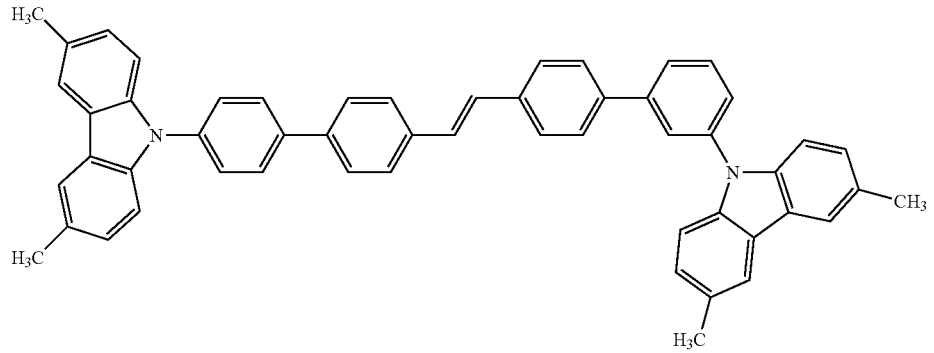
(71)
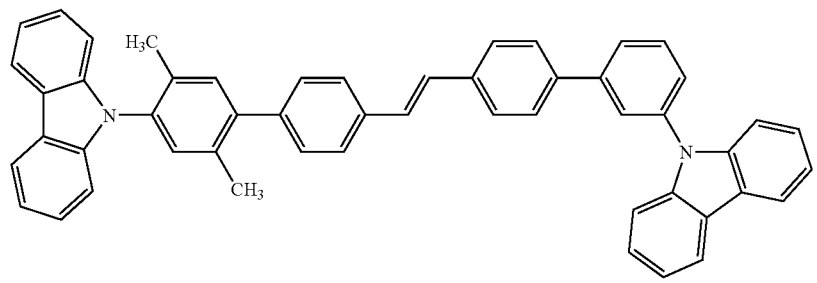
(72)
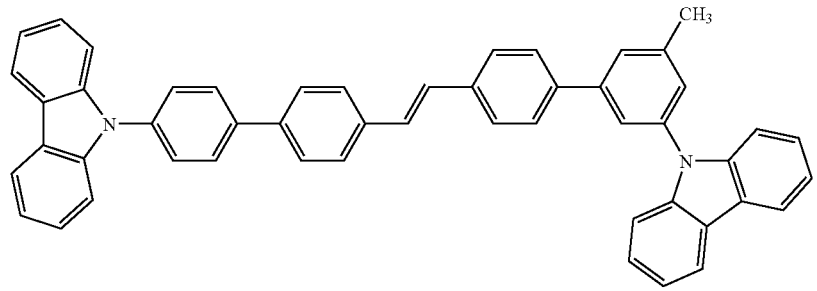
(73)

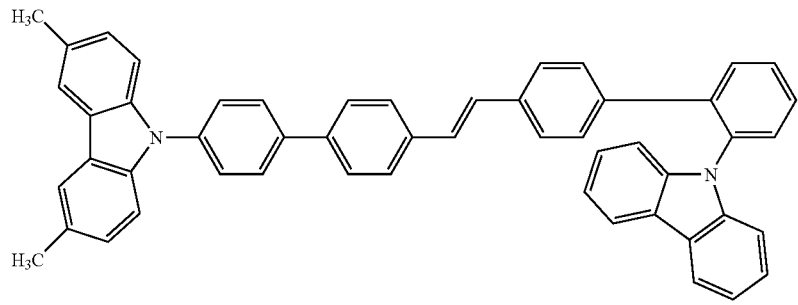
(74)
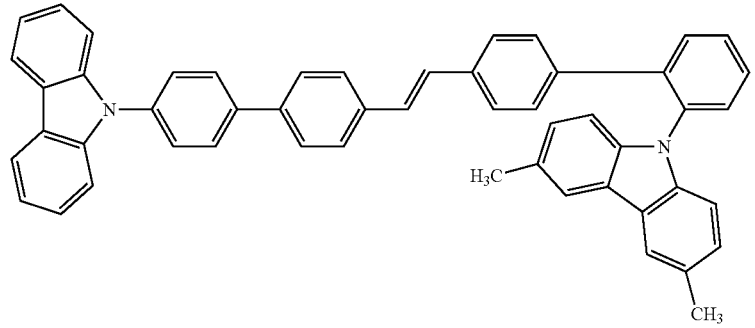
(75)
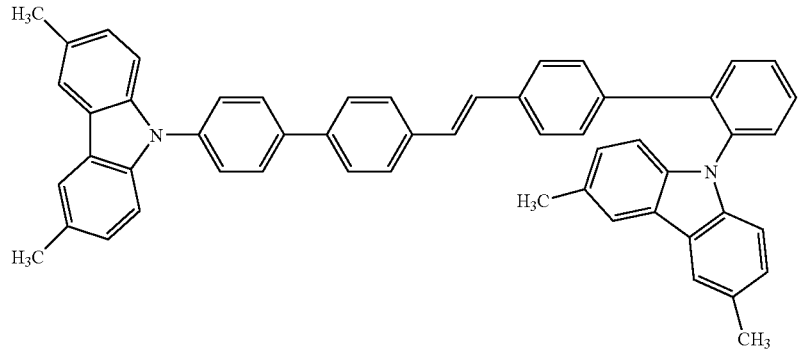
(76)
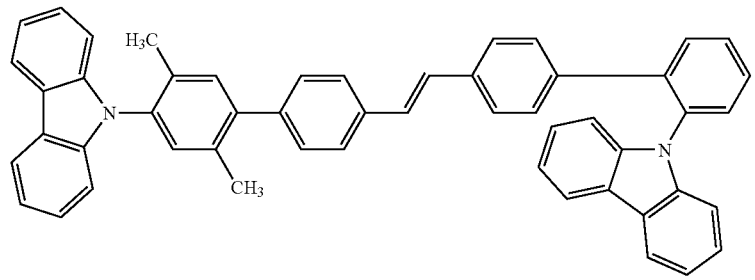
(77)
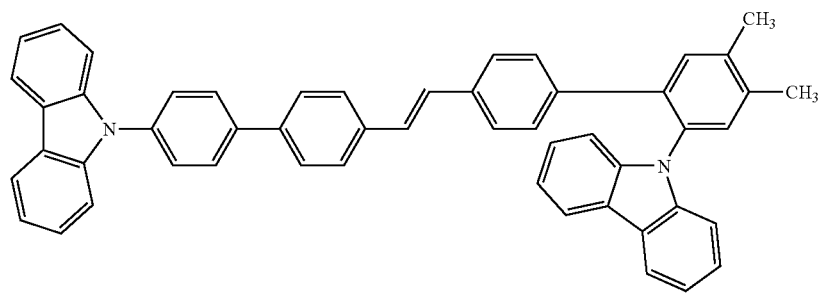
(78)

-continued
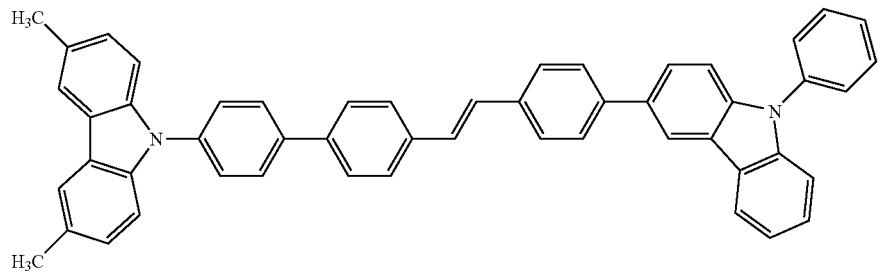
(79)
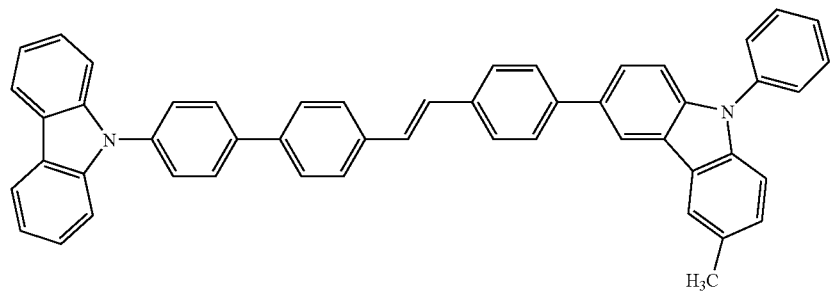
(80)
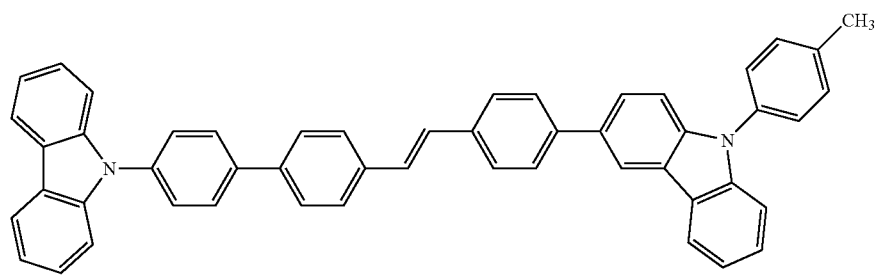
(81)
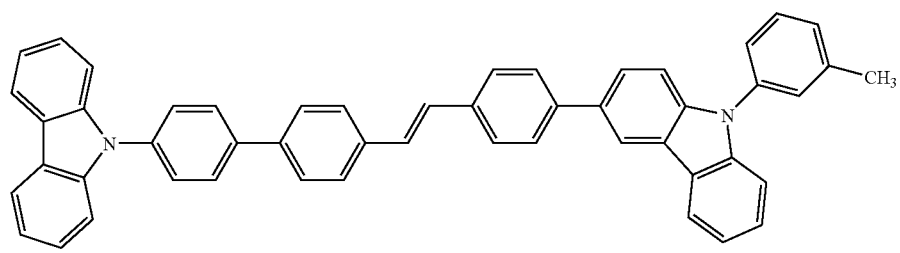
(82)
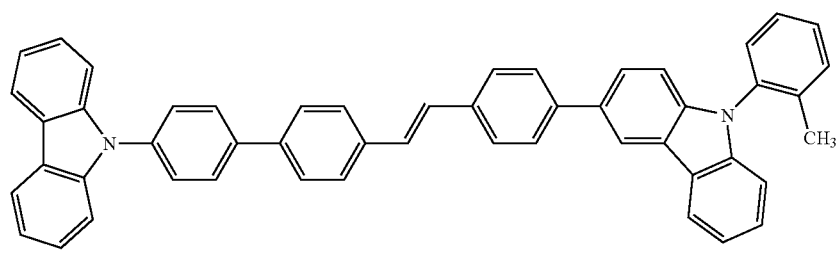
(83)
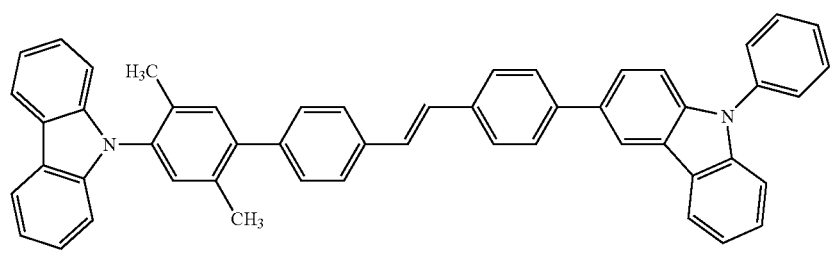
(84)

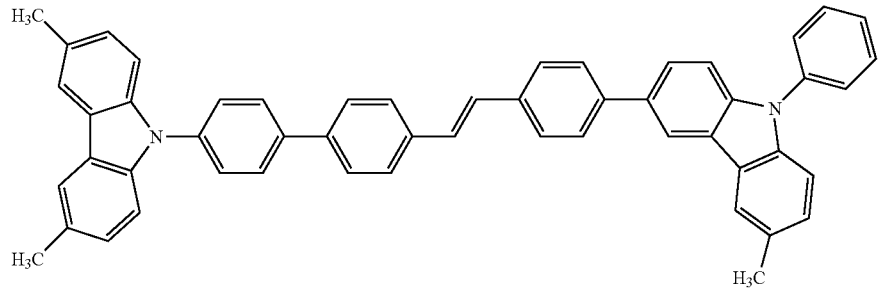
(85)
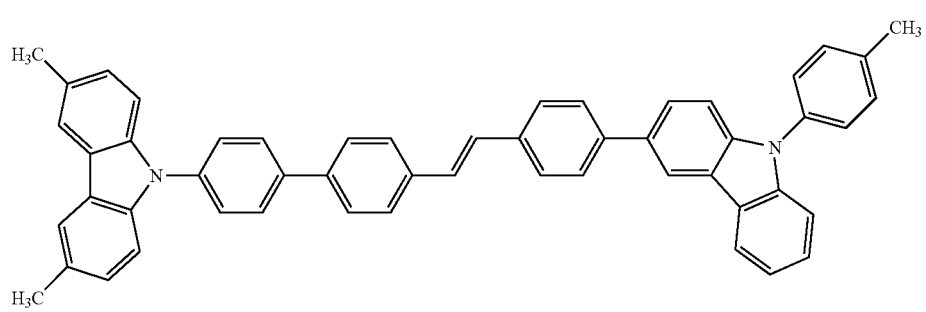
(86)
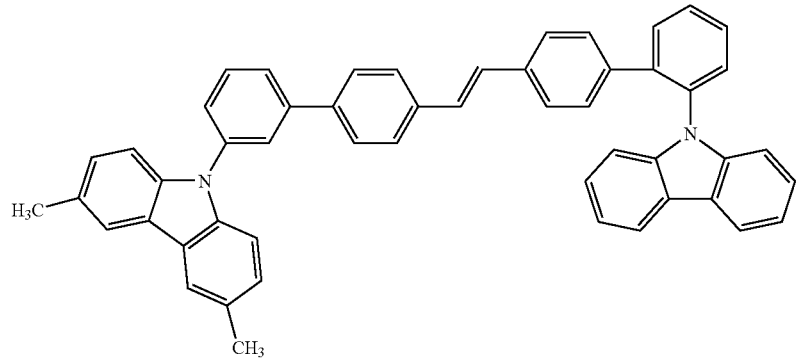
(87)
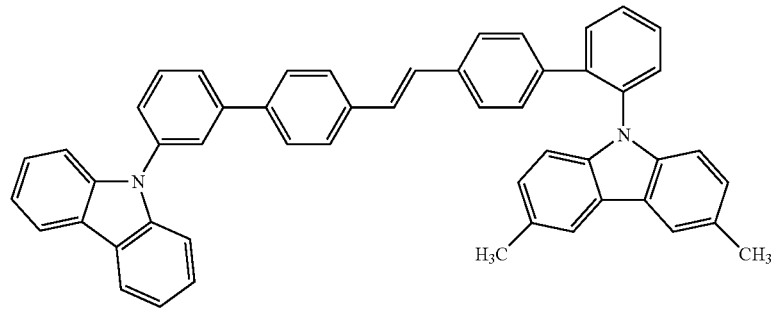
(88)

-continued
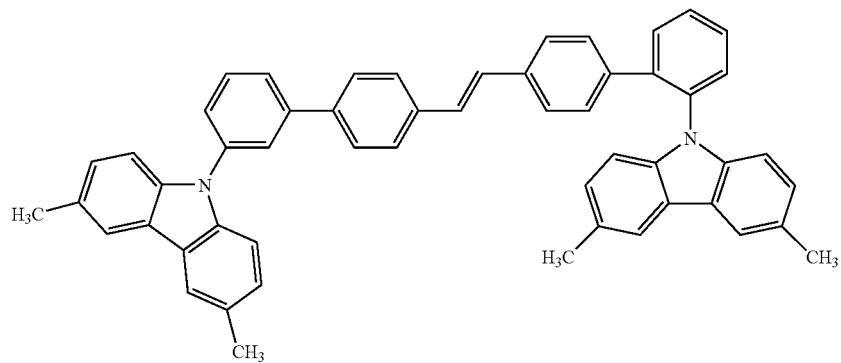
(89)
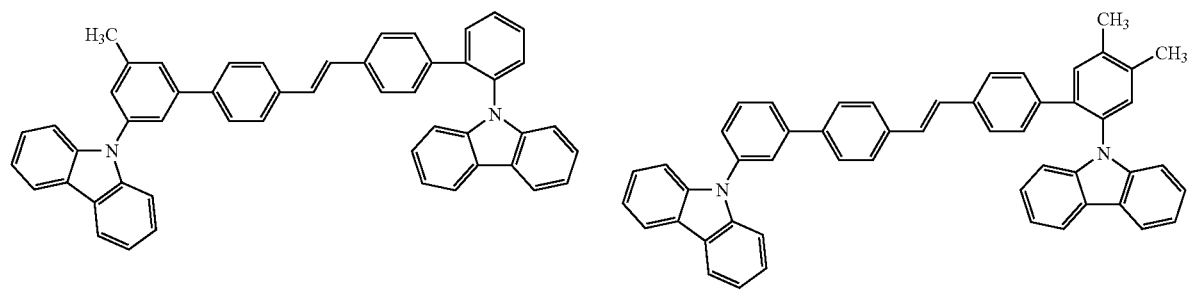
(90) (91)
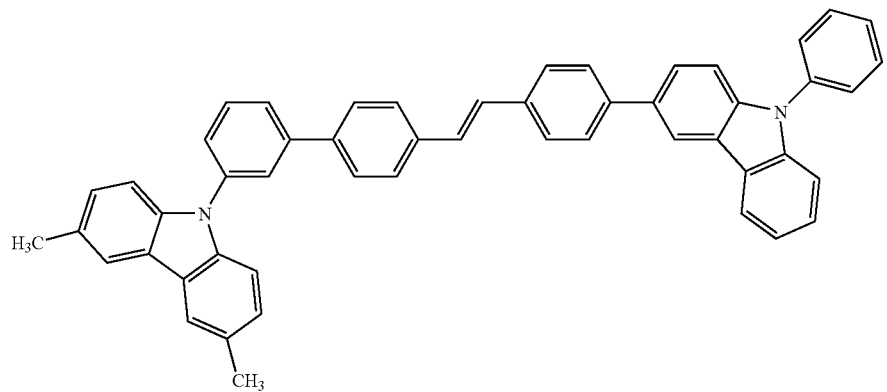
(92)
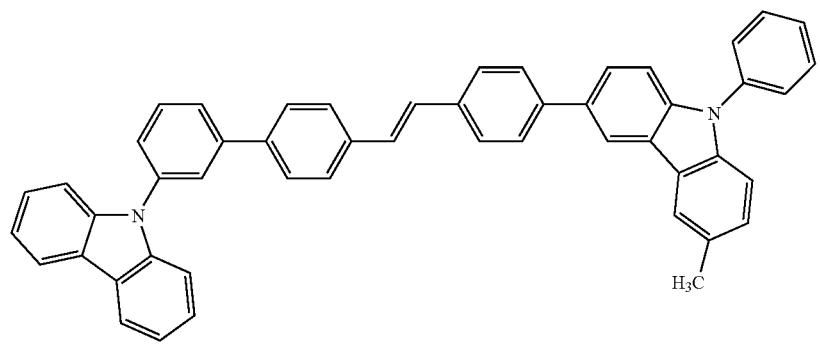
(93)

-continued
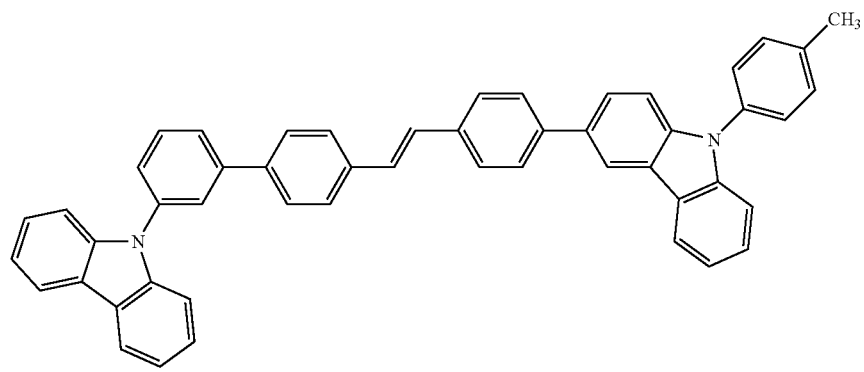
(94)
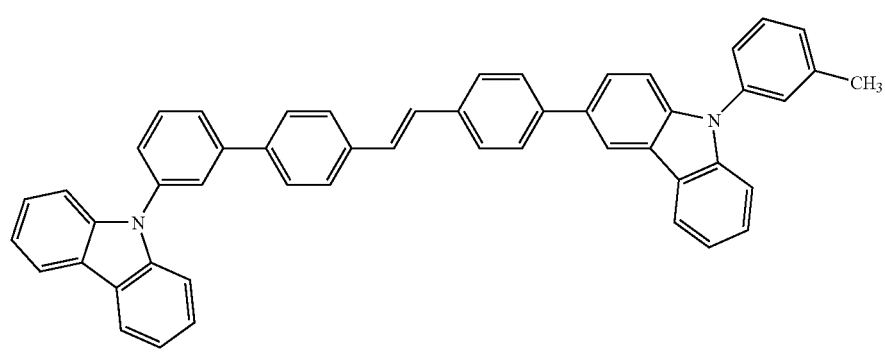
(95)
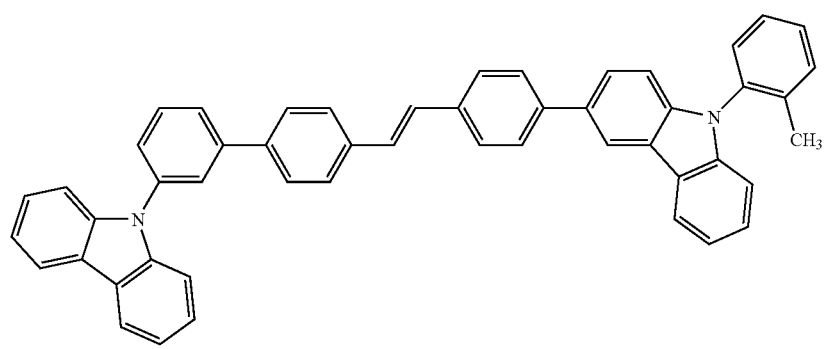
(96)
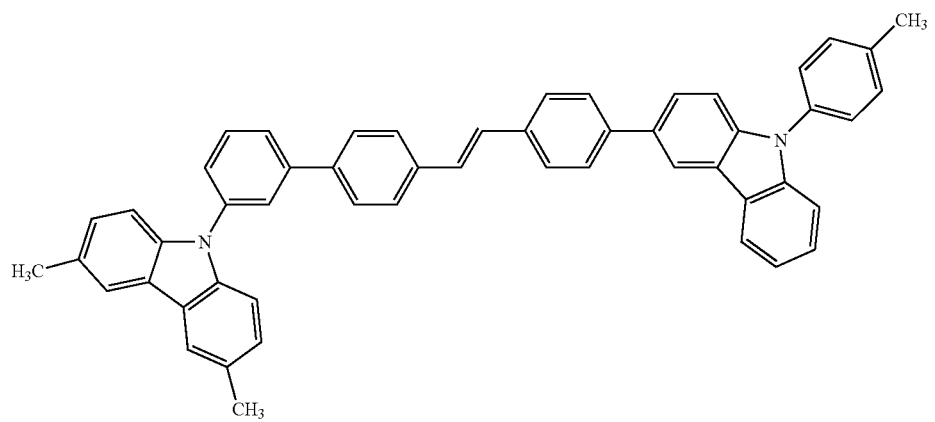
(97)

-continued
(98)
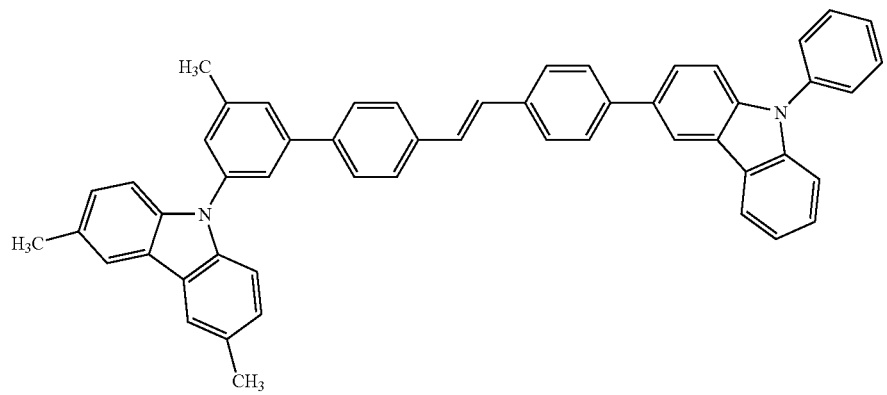
(99) (100)
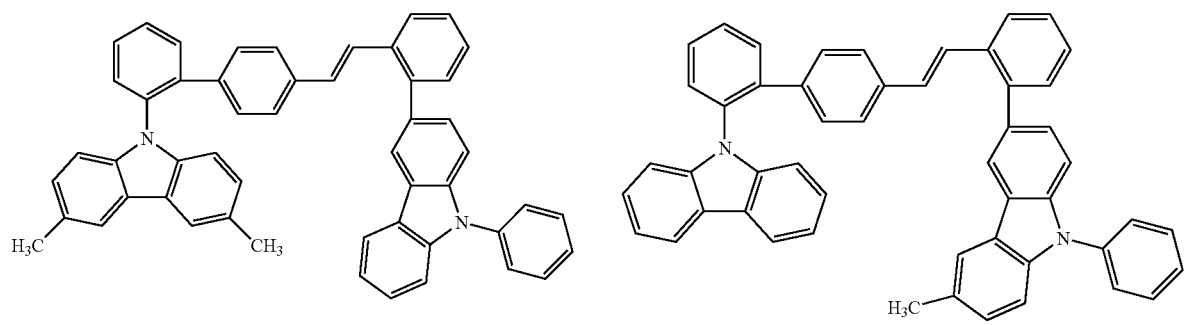
(101) (102)
(103) (104)
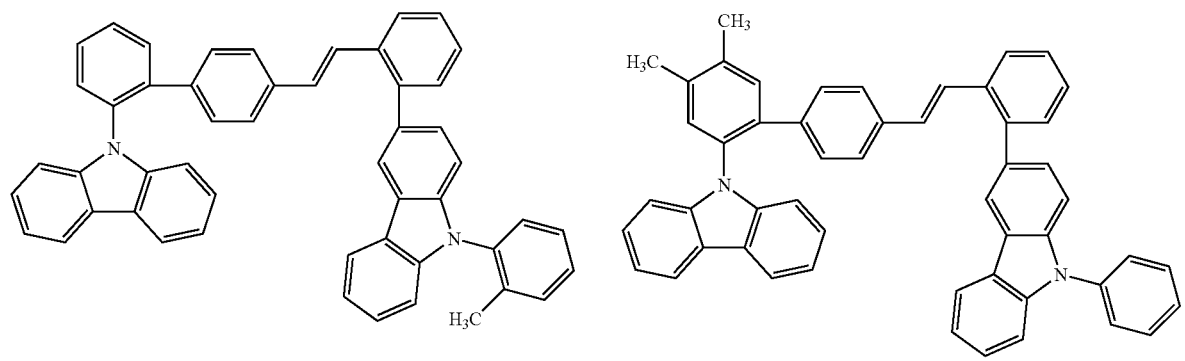

-continued (105)
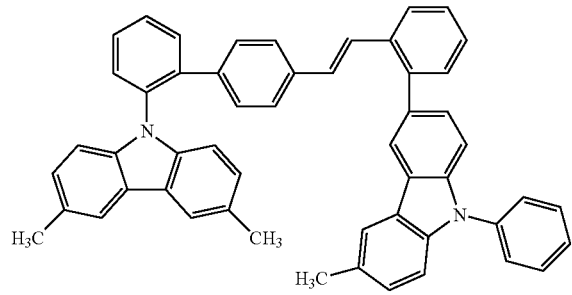

(106)
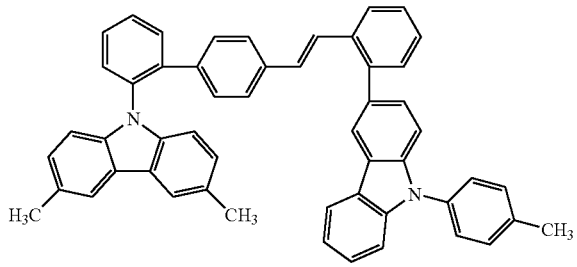

(107)
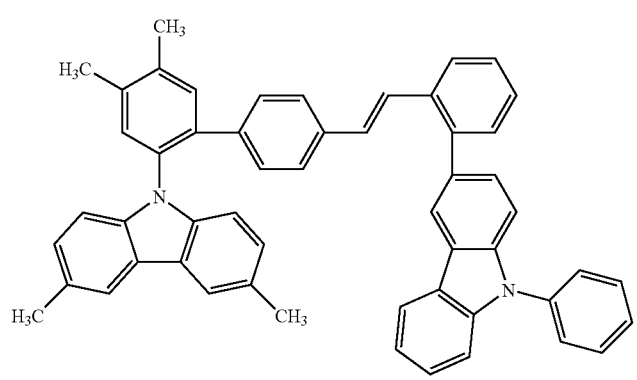

The above described stilbene derivatives of the present invention can exhibit blue light emission with excellent color purity. Therefore, the stilbene derivatives are highly useful as light emitting materials. Further, the stilbene derivatives have excellent resistance to repetition of oxidation reactions.

Embodiment Mode 2

A synthesis method of a stilbene derivative of the present invention represented by a general formula (G7) is described below. Note that a synthesis method of the stilbene derivative of the present invention is not limited to the one described in this embodiment mode, and another synthesis method may be employed for the synthesis.

Note that, in the general formula (G7), each of $R^1$ to $R^6$ represents any one of hydrogen and an alkyl group having 1 to 4 carbon atoms.

As represented in a following synthesis scheme (a-1), the stilbene derivative of the present invention represented by the general formula (G7) can be obtained by a coupling reaction of a dihalogen compound of stilbene and a boronic acid derivative of phenylcarbazole or a phenylcarbazole derivative substituted by organoboron, in the presence of a base using a metal catalyst. Note that, as the metal catalyst in the coupling, a palladium catalyst such as palladium acetate(II), tetrakis(triphenylphosphine)palladium(0), or bis(tricyclohexylphosphine)palladium(II)dichloride, is preferable. As the base, an inorganic base such as potassium carbonate or sodium carbonate, an organic base such as a metal alkoxide like sodium-tert-butoxide or potassium-tert-butoxide, or the like can be used.

(G7)
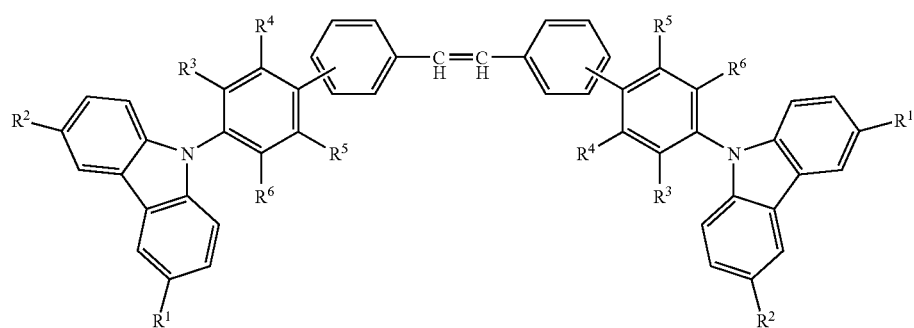

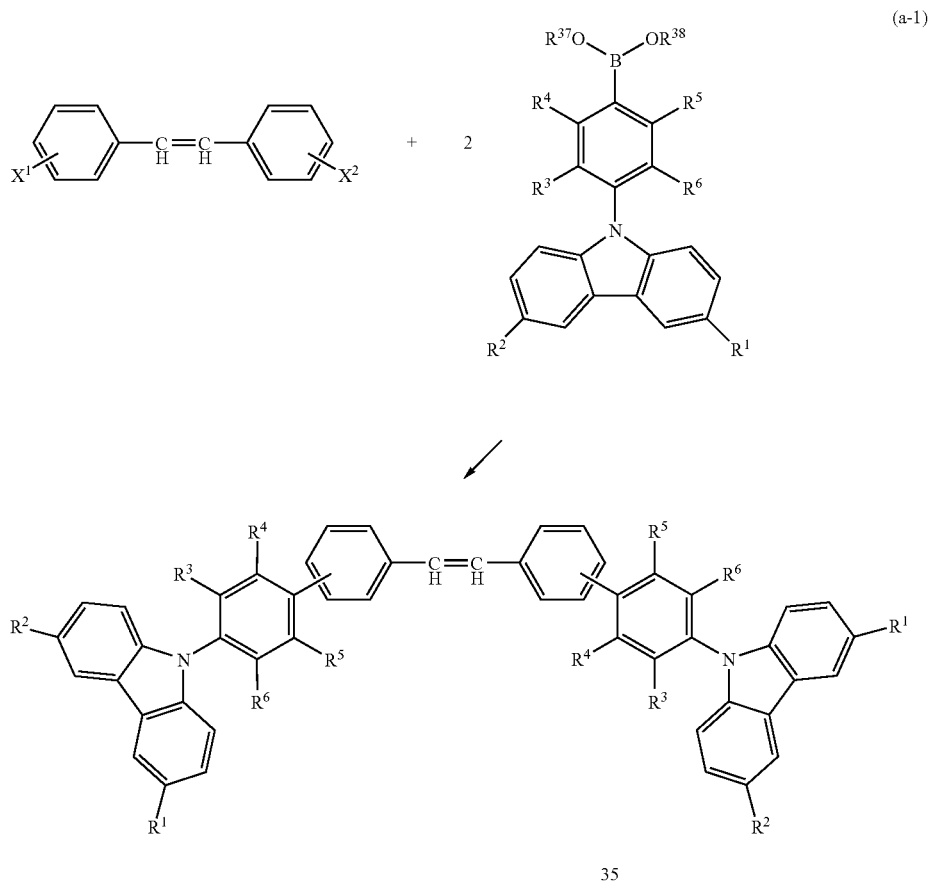

Note that, in the synthesis scheme (a-1), each of $R^1$ to $R^6$ represents any one of hydrogen and an alkyl group having 1 to 4 carbon atoms, and each of $R^{37}$ and $R^{38}$ represents any one of hydrogen and an alkyl group having 1 to 10 carbon atoms. Note that $R^{37}$ and $R^{38}$ may be connected to each other and form a ring. In addition, each of $X^1$ and $X^2$ represents a halogen group and they may be either the same or different. In particular, $X^1$ and $X^2$ are preferably bromine and iodine, which have high reactivity, are preferable.

The stilbene derivative obtained as described above can exhibit blue light emission with excellent color purity. Accordingly, the stilbene derivative is highly useful as a light emitting material. In addition, the stilbene derivative has excellent resistance to repetition of oxidation reactions.

Note that the dihalogen compound of stilbene, which is a reactant used in the synthesis scheme (a-1), can be obtained by a method such as one represented by a following synthesis scheme (b-1). In the synthesis scheme (b-1), each of $X^1$ to $X^3$ represents a halogen group, preferably, bromine or iodine, which has high reactivity.

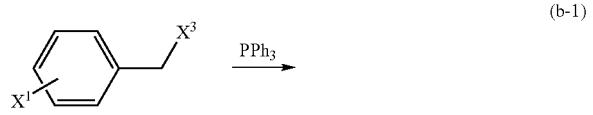

(b-1)

-continued

As shown by the synthesis scheme (b-1), the dihalogen compound of stilbene is obtained by so-called Wittig reaction, in which halogenated benzyltriphenylphosphonium salt (α1) and halogenated benzaldehyde (β1) react in the presence of a base.

Alternatively, the dihalogen compound of stilbene can be obtained by Horner-Emmons reaction in which phosphonate ester (α2) is used instead of the triphenylphosphonium salt (α1) in the synthesis scheme (b-1), as shown in a following synthesis scheme (b-2). Note that, in the synthesis scheme (b-2), each of $X^1$ to $X^3$ represents a halogen group preferably, bromine or iodine, which has high reactivity; and $R^{39}$ represents any alkyl group having 1 to 10 carbon atoms.

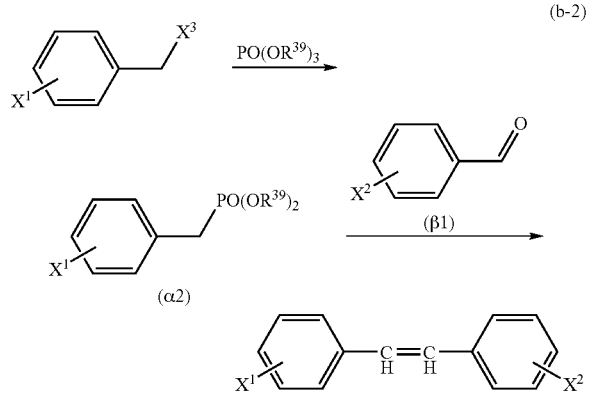

(b-2)

(α2)

(β1)

Note that synthesis scheme (a-1) shows the case, in which as the boronic acid derivative of phenylcarbazole or the phenylcarbazole derivative substituted by organoboron, which are the reactants, a substance which has phenylcarbazole having a phenyl group with a boronic acid at the para-position or a substance which has phenylcarbazole having a phenyl group with the para-position substituted by organoboron is used; however, the position is not limited thereto. For example, when a boronic acid derivative of phenylcarbazole which has phenylcarbazole having a phenyl group with a boronic acid at the meta-position or a phenylcarbazole derivative which has phenylcarbazole having a phenyl group with the meta-position substituted by organoboron is used as the reactant, a stilbene derivative represented by a following general formula (G8) is obtained. When the position is the ortho-position, a stilbene derivative represented by a following general formula (G9) is obtained. Further, when a boronic acid derivative of phenylcarbazole which has phenylcarbazole having carbazole with a boronic acid at the 3-position or a phenylcarbazole derivative which has phenylcarbazole having carbazole with the 3-position substituted by organoboron is used, a stilbene derivative represented by a following general formula (G10) is obtained.

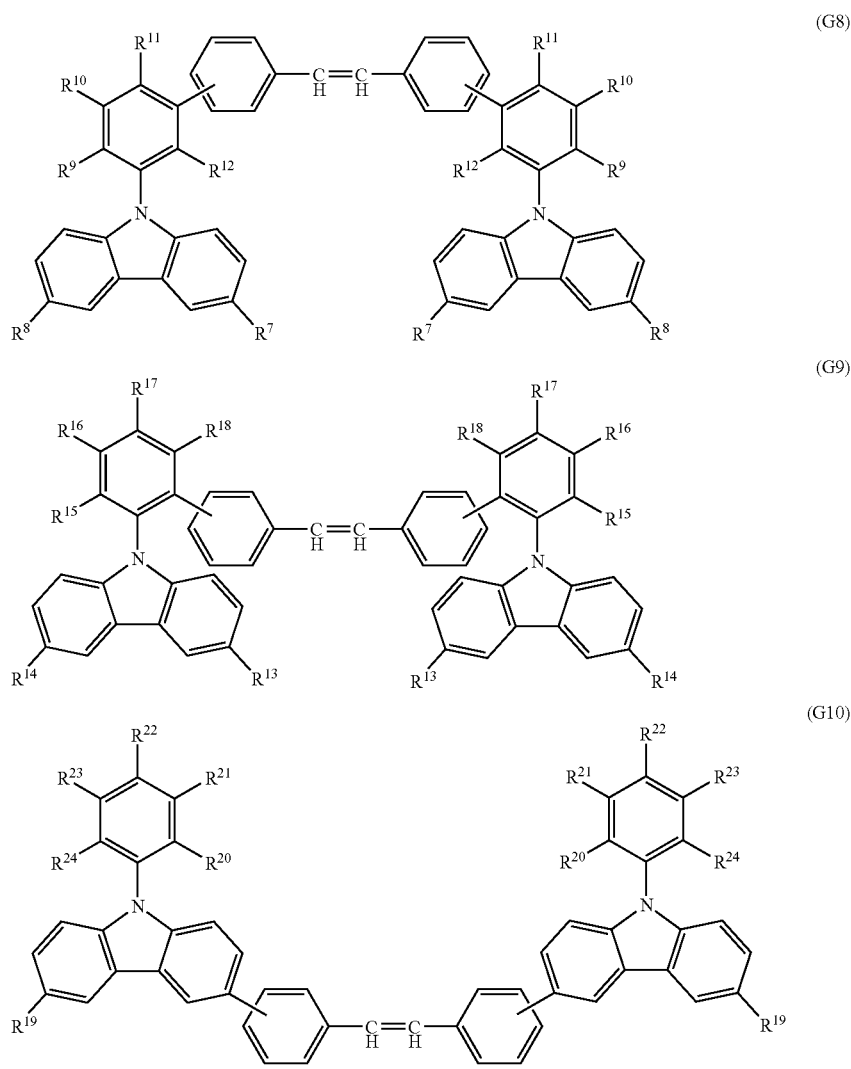

Note that, in each of the general formulae (G8) to (G10), each of $R^7$ to $R^{24}$ represents any one of hydrogen and an alkyl group having 1 to 4 carbon atoms.

The stilbene derivatives as described above can exhibit blue light emission with excellent color purity. Accordingly, the stilbene derivatives are highly useful as light emitting materials. In addition, the stilbene derivatives have excellent resistance to repetition of oxidation reactions.

Embodiment Mode 3

In this embodiment mode, a synthesis method of a stilbene derivative of the present invention which is represented by the foregoing general formula (G1) and has $A^1$ and $B^1$ with different structures is described. Note that a synthesis method of the stilbene derivative of the present invention is not limited to the one described in this embodiment mode, and another synthesis method may be employed for the synthesis.

A synthesis method of a stilbene derivative of the present invention represented by a general formula (G11) is described below.

of hydrogen and an alkyl group having 1 to 4 carbon atoms, and each of $R^{37}$ and $R^{38}$ represents any one of hydrogen and an alkyl group having 1 to 10 carbon atoms. Note that $R^{37}$ and $R^{38}$ may be connected to each other and form a ring. Each of $R^{40}$ and $R^{41}$ represents any one of hydrogen and an alkyl group having 1 to 10 carbon atoms and they may be connected to each other and form a ring. In addition, each of $X^1$ and $X^2$ represents a halogen group and they may be either the same or different. In particular, $X^1$ and $X^2$ are preferably bromine or iodine, which have high reactivity; and more preferably, they are different from each other.

As represented in the synthesis scheme (c-1), first, a stilbene derivative having a phenylcarbazole skeleton (Compound A) can be obtained by a coupling reaction of a dihalogen compound of stilbene and a first boronic acid derivative of phenylcarbazole or phenylcarbazole derivative substituted by organoboron, in the presence of a base using a metal catalyst. Then, the stilbene derivative of the present invention represented by the general formula (G11) can be obtained by a coupling reaction using the obtained stilbene derivative

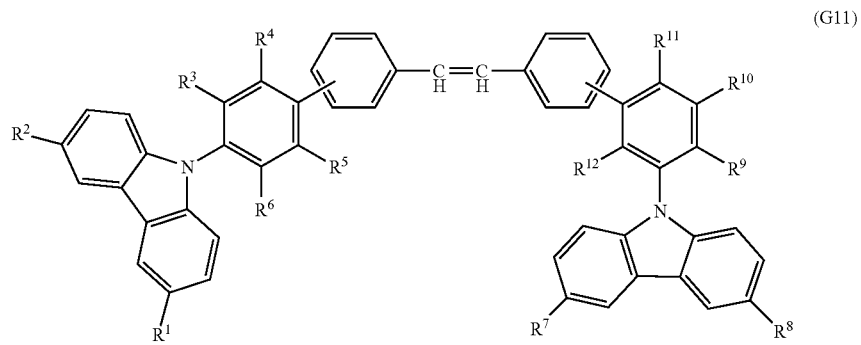

(G11)

Note that, in the general formula (G11), each of $R^1$ to $R^{12}$ represents any one of hydrogen and an alkyl group having 1 to 4 carbon atoms.

As represented in a following synthesis scheme (c-1), the stilbene derivative of the present invention represented by the general formula (G11) can be obtained by a two-step coupling reaction in which a dihalogen compound of stilbene and boronic acid derivatives of phenylcarbazole or phenylcarbazole derivatives substituted by organoboron, which are substituted in different positions, are used. Note that, in the synthesis scheme (c-1), each of $R^1$ to $R^{12}$ represents any one having a phenylcarbazole skeleton (Compound A) and a second boronic acid derivative of phenylcarbazole or phenylcarbazole derivative substituted by organoboron, in the presence of a base using a metal catalyst. Note that. as the metal catalyst in the coupling, a palladium catalyst such as palladium acetate(II), tetrakis(triphenylphosphine)palladium(0), or bis(tricyclohexylphosphine)palladium(II)dichloride is preferable. As the base, an inorganic base such as potassium carbonate or sodium carbonate, an organic base such as a metal alkoxide like sodium-tert-butoxide or potassium-tert-butoxide, or the like can be used.

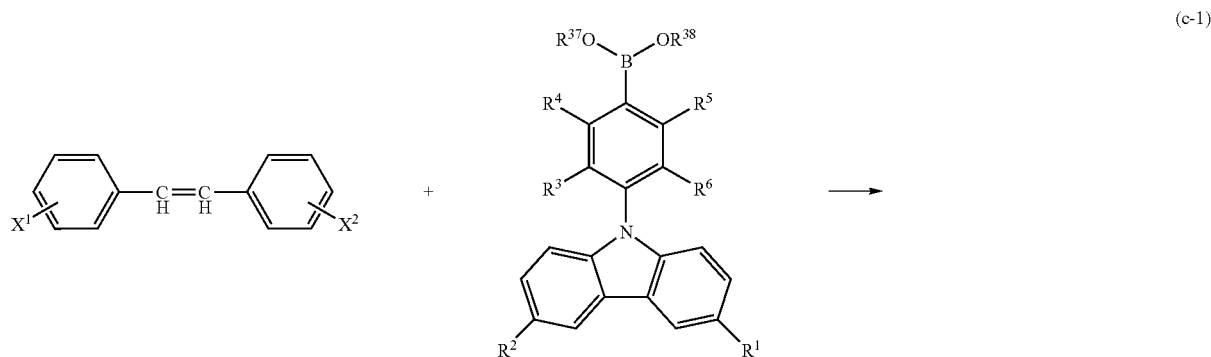

(c-1)

-continued

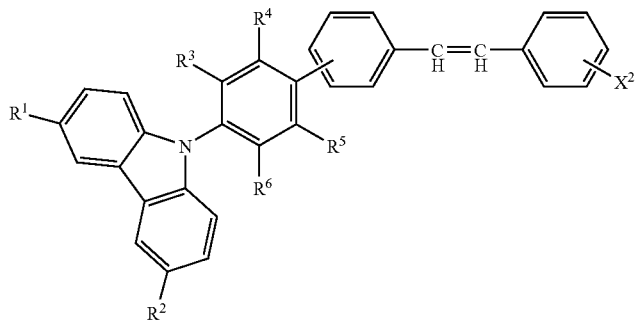

COMPOUND A

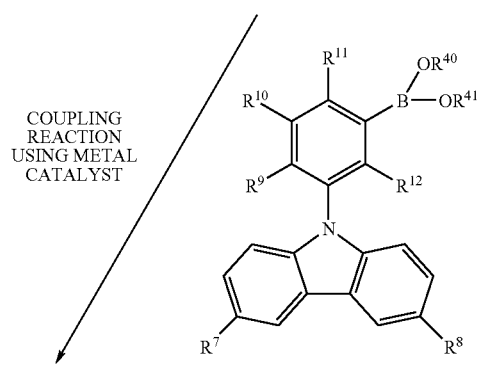

COUPLING REACTION USING METAL CATALYST

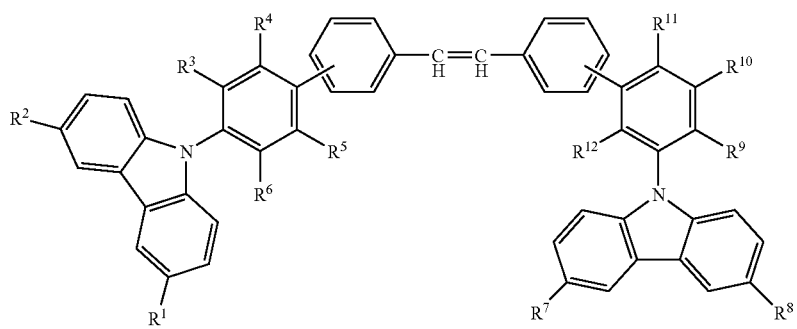

Note that, the foregoing synthesis scheme (c-1) shows the case, in which as the first boronic acid derivative of phenylcarbazole or phenylcarbazole derivative substituted by organoboron, a substance having a phenyl group with the para-position substituted by a boronic acid or organoboron is used; and as the second boronic acid derivative of phenylcarbazole or phenylcarbazole derivative substituted by organoboron, a substance which has a phenyl group with the meta-position substituted by a boronic acid or organoboron is used; however, the positions to be substituted are not limited to the para-position and the meta-position. The position to be substituted may be any one of the para-position, the meta-position, and the ortho-position. Needless to say, as the first boronic acid derivative of phenylcarbazole or phenylcarbazole derivative substituted by organoboron, a substance which has a phenyl group with the meta-position substituted by a boronic acid or organoboron can be used and as the second boronic acid derivative of phenylcarbazole or phenylcarbazole derivative substituted by organoboron, a substance which has a phenyl group with the para-position substituted by a boronic acid or organoboron can be used. Further, a boronic acid derivative of phenylcarbazole having carbazole with the 3-position substituted by a boronic acid or organoboron, or a phenylcarbazole derivative having carbazole with the 3-position substituted by organoboron may be used as a reactant. With using the boronic acid derivative of phenylcarbazole or the phenylcarbazole derivative substituted by organoboron as described above, a stilbene derivative represented, not by the general formula (G11), but by any one of the following general formulae (G12) to (G16) can be obtained.

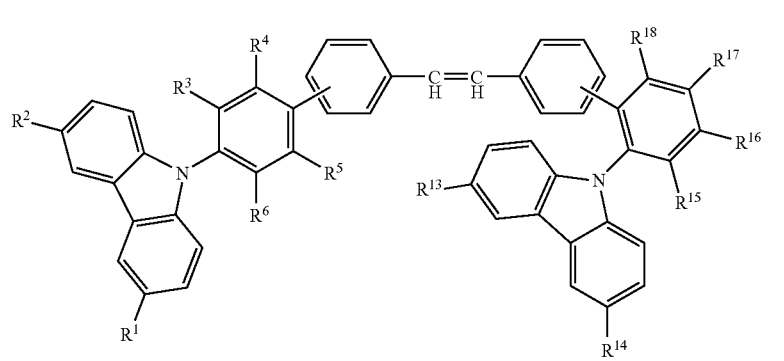
(G12)
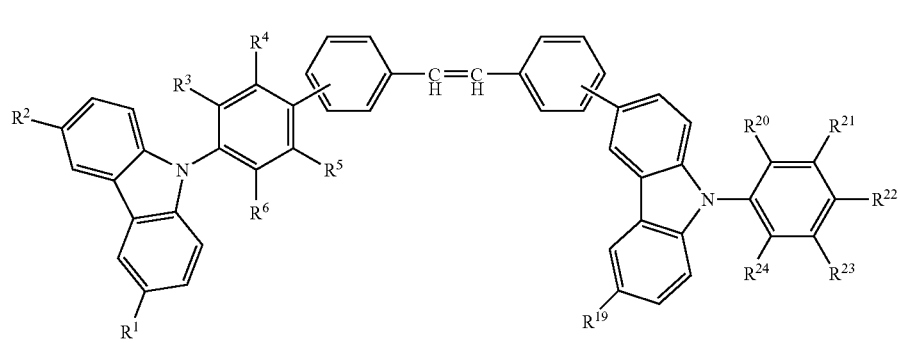
(G13)
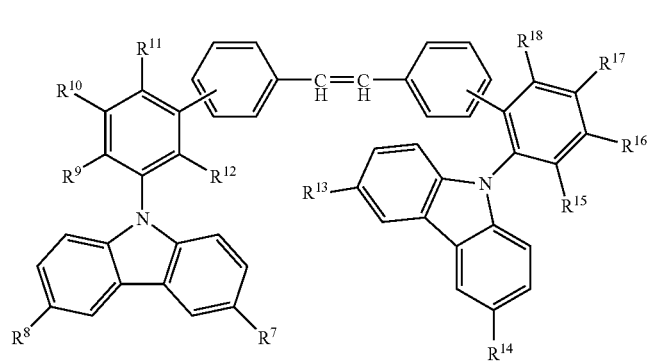
(G14)
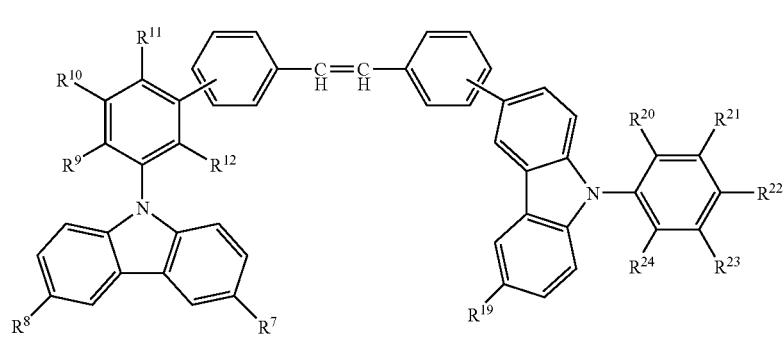
(G15)

-continued

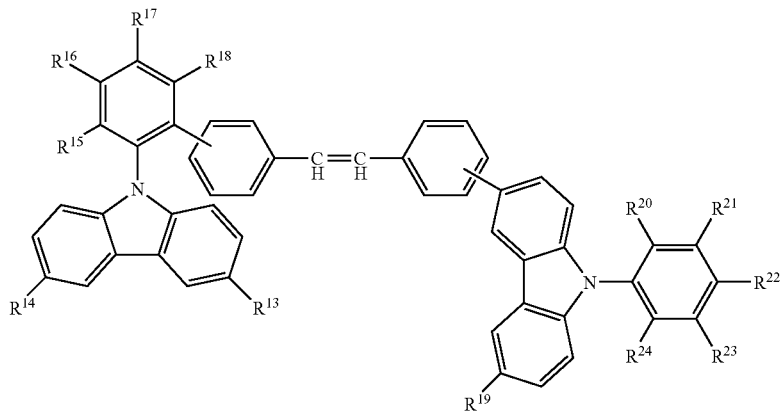

(G16)

In the foregoing synthesis scheme (c-1), the same substance may be used as the first and the second boronic acid derivatives of phenylcarbazole or phenylcarbazole derivatives substituted by organoboron, so that the stilbene derivative of the present invention described in Embodiment Mode 2 may be synthesized.

The stilbene derivatives as described above can exhibit blue light emission with excellent color purity. Accordingly, the stilbene derivatives are highly useful as light emitting materials. In addition, the stilbene derivatives have excellent resistance to repetition of oxidation reactions.

Embodiment Mode 4

In this embodiment mode, a synthesis method of a stilbene derivative of the present invention represented by the foregoing general formula (G2) is described. Note that a synthesis method of the stilbene derivative of the present invention is not limited to the one described in this embodiment mode, and another synthesis method may be employed for the synthesis.

A synthesis method of a stilbene derivative of the present invention represented by a general formula (G17) is described below.

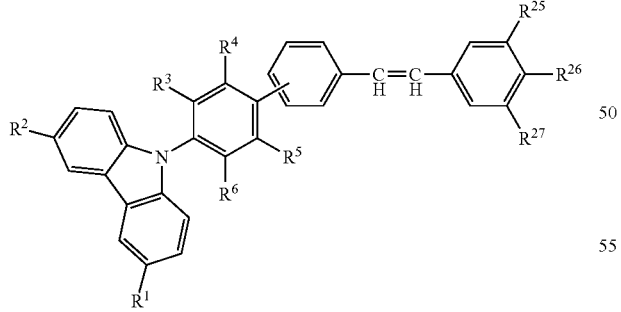

(G17)

Note that, in the general formula (G17), each of $R^1$ to $R^6$ and $R^{25}$ to $R^{27}$ represents any one of hydrogen and an alkyl group having 1 to 4 carbon atoms.

As represented in a following synthesis scheme (d-1), the stilbene derivative of the present invention represented by the general formula (G17) can be obtained by a coupling reaction of a dihalogen compound of stilbene and a boronic acid derivative of phenylcarbazole or a phenylcarbazole derivative substituted by organoboron, in the presence of a base using a metal catalyst. Note that, as the metal catalyst in the coupling, a palladium catalyst such as palladium acetate(II), tetrakis (triphenylphosphine)palladium(0), or bis(tricyclohexylphosphine)palladium(II)dichloride, is preferable. As the base, an inorganic base such as potassium carbonate or sodium carbonate, an organic base such as a metal alkoxide like sodium-tert-butoxide or potassium-tert-butoxide, or the like can be used.

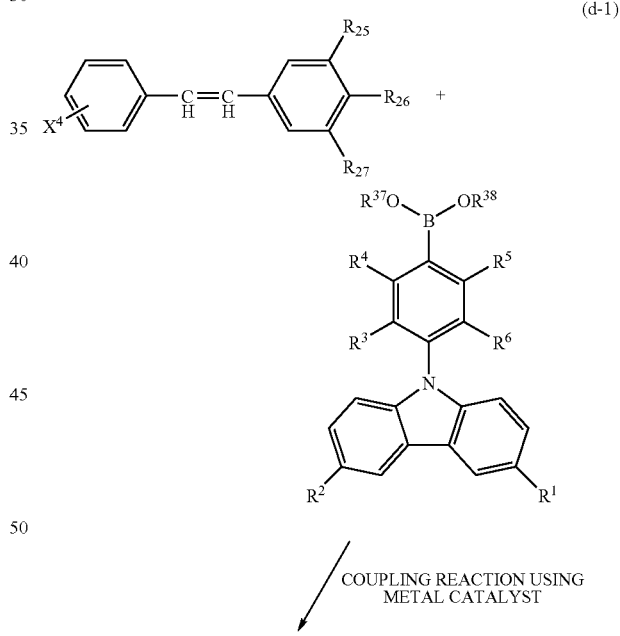

(d-1)

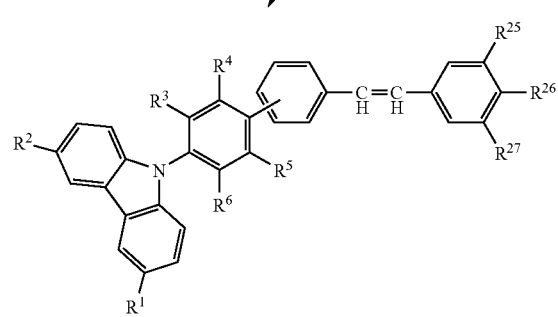

Note that in the synthesis scheme (d-1), each of $R^1$ to $R^6$ and $R^{25}$ to $R^{27}$ represents any one of hydrogen and an alkyl group having 1 to 4 carbon atoms, and each of $R^{37}$ and $R^{38}$ represents any one of hydrogen and an alkyl group having 1 to 10 carbon atoms. Note that $R^{37}$ and $R^{38}$ may be connected to each other and form a ring. In addition, $X^4$ represents a halogen group, preferably, bromine or iodine, which has high reactivity.

The stilbene derivatives obtained as described above can exhibit blue light emission with excellent color purity. Accordingly, the stilbene derivatives are highly useful as light emitting materials. In addition, the stilbene derivatives have excellent resistance to repetition of oxidation reactions.

Note that the dihalogen compound of stilbene, which is a reactant used in the synthesis scheme (d-1), can be obtained by a method such as one represented by following synthesis schemes.

As shown in the synthesis scheme (e-1), the halogen compound of stilbene can be obtained by so-called Wittig reaction in which halogenated benzyltriphenylphosphonium salt (α3) and a benzaldehyde derivative (β2) react in the presence of a base. The halogen compound of stilbene can also be obtained by Horner-Emmons reaction in which phosphonate ester (α4) is used instead of the triphenylphosphonium salt (α3) in the synthesis scheme (e-1), as shown in a synthesis scheme (e-2). Note that, in each of the synthesis schemes (e-1) and (e-2), each of $R^{25}$ to $R^{27}$ represents any one of hydrogen and an alkyl group having 1 to 4 carbon atoms, $R^{39}$ represents an alkyl group having 1 to 10 carbon atoms, and each of $X^4$ and $X^5$ represents a halogen group, preferably, bromine or iodine.

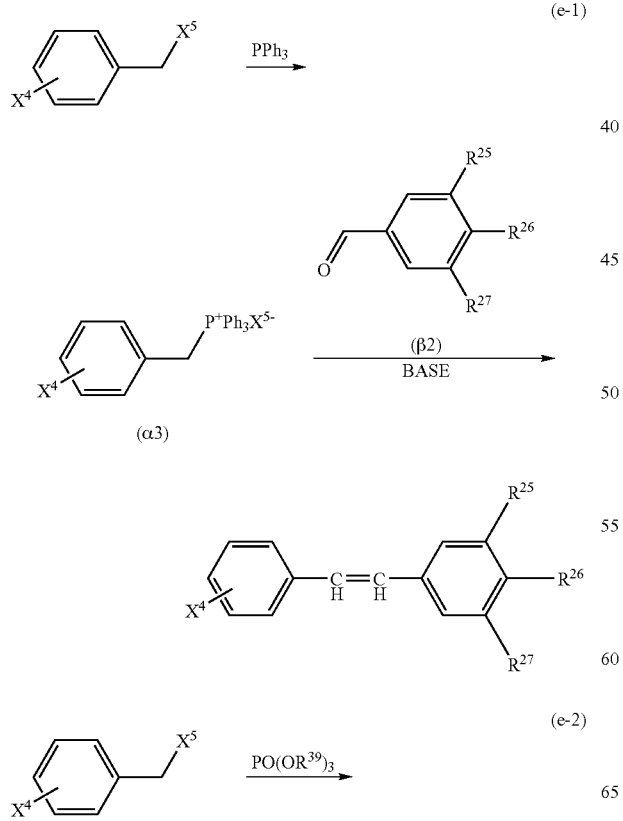

(e-1)

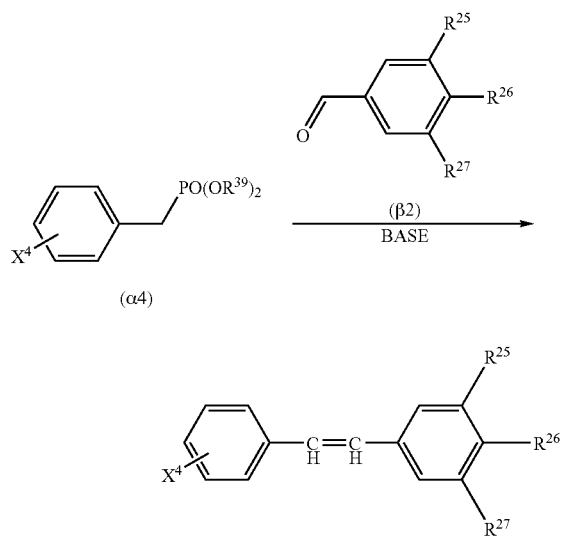

Alternatively, as shown in a following synthesis scheme (e-3), the halogen compound of stilbene can be obtained by so-called Wittig reaction in which benzyltriphenylphosphonium salt (α5) and a halogenated benzaldehyde derivative (β3) react in the presence of a base. Further alternatively, the halogen compound of stilbene can also be obtained by Horner-Emmons reaction in which phosphonate ester (α6) is used instead of the triphenylphosphonium salt (α5) in the synthesis scheme (e-3), as shown in a synthesis scheme (e-4). Note that, in each of the synthesis schemes (e-3) and (e-4), each of $R^{25}$ to $R^{27}$ represents any one of hydrogen and an alkyl group having 1 to 4 carbon atoms, $R^{39}$ represents any alkyl group having 1 to 10 carbon atoms, and each of $X^4$ and $X^5$ represents a halogen group, preferably, bromine or iodine.

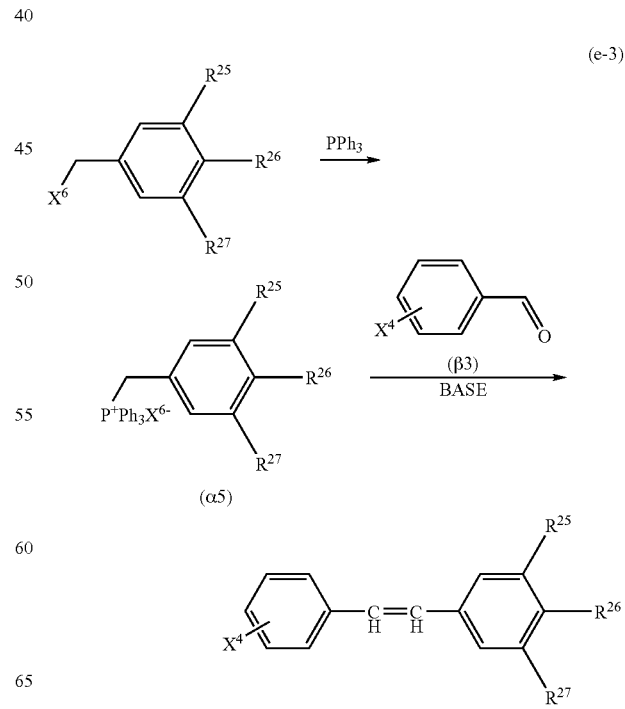

(e-3)

-continued (e-4)

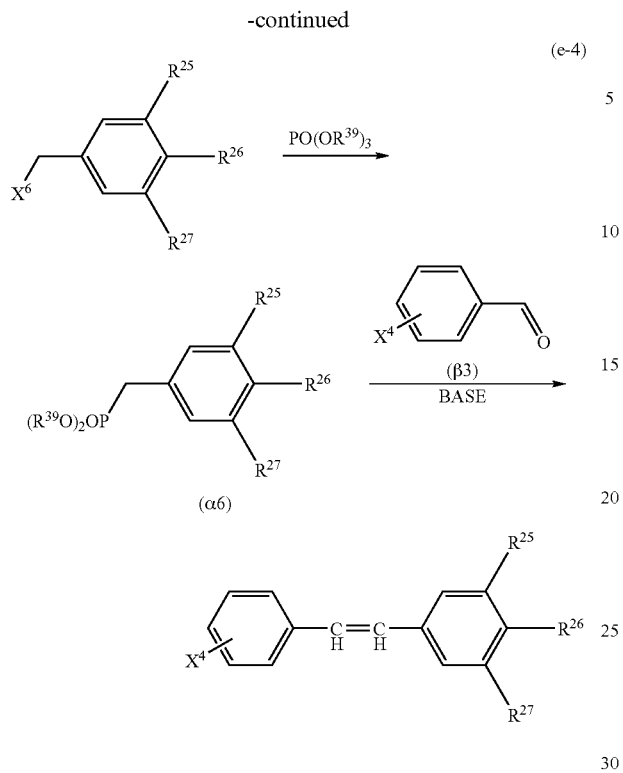

Note that, the synthesis scheme (d-1) shows the case, in which as the boronic acid derivative of phenylcarbazole or the phenylcarbazole derivative substituted by organoboron, a substance which has a phenyl group with the para-position substituted by a boronic acid or organoboron is used; however, the position to be substituted is not limited thereto. For example, a boronic acid derivative of phenylcarbazole with the meta-position or ortho-position in a phenyl group or the 3-position in carbazole substituted by a boronic acid or a phenylcarbazole derivative with the meta-position or ortho-position in a phenyl group or the 3-position in carbazole substituted by organoboron can be used. With using the foregoing boronic acid derivative of phenylcarbazole or the phenylcarbazole derivative substituted by organoboron, a stilbene derivative represented by any one of following general formulae (G18) to (G20) can be obtained.

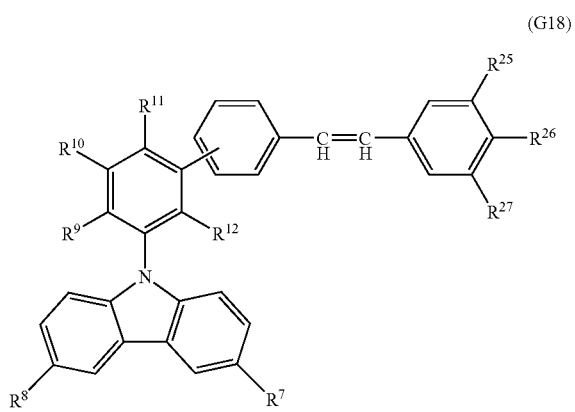

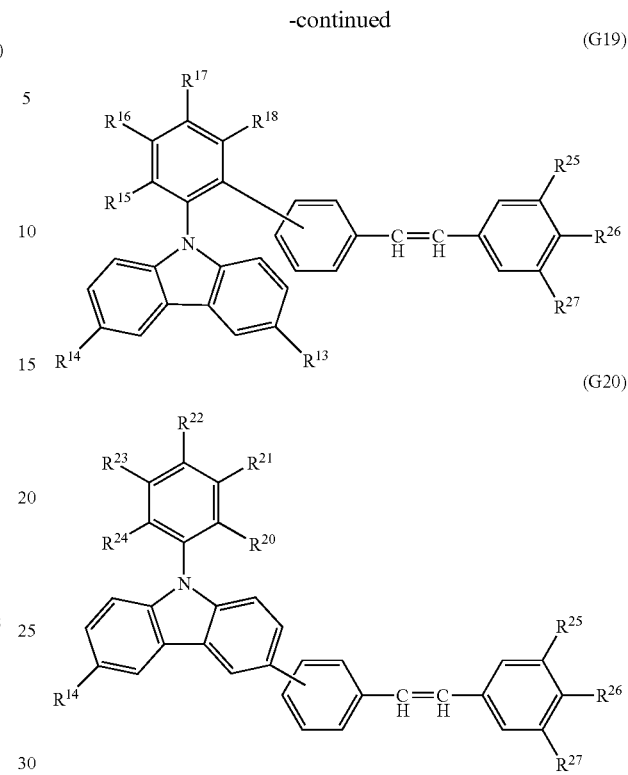

Note that, in any one of the general formulae (G18) to (G20), each of $R^7$ to $R^{27}$ represents any one of hydrogen and an alkyl group having 1 to 4 carbon atoms.

The stilbene derivatives as described above can exhibit blue light emission with excellent color purity. Accordingly, the stilbene derivatives are highly useful as light emitting materials. In addition, the stilbene derivatives have excellent resistance to repetition of oxidation reactions.

Embodiment Mode 5

A mode of a light emitting element using a stilbene derivative of the present invention is described with reference to FIG. 1.

FIG. 1 shows a light emitting element including a light emitting layer 113 between a first electrode 101 and a second electrode 102. The light emitting layer 113 contains the stilbene derivative of the present invention.

In addition to the light emitting layer 113, a hole injecting layer 111, a hole transporting layer 112, an electron transporting layer 114, an electron injecting layer 115, and the like are provided between the first electrode 101 and the second electrode 102. These layers are stacked in a manner such that holes are injected form the first electrode 101 side and electrons are injected from the second electrode 102 side when voltage is applied so that electric potential of the first electrode 101 is higher than that of the second electrode 102.

In such a light emitting element, the holes injected from the first electrode 101 side and the electrons injected from the second electrode 102 side are recombined with each other in the light emitting layer 113 and excite the stilbene derivative of the present invention contained therein. The stilbene derivative in the excited state emits light while returning to the ground state. Thus, the stilbene derivative of the present invention serves as a light emitting substance.

Although the light emitting layer 113 may be a layer formed of only the stilbene derivative of the present invention, the light emitting layer 113 is preferably formed in a manner such that the light emitting substance is dispersed in a layer formed of a substance (host) having a larger energy gap than the light emitting substance, in the case where concentration quenching occurs. Concentration quenching can be prevented by dispersing the stilbene derivative of the present invention in the light emitting layer 113. Note that, an energy gap refers to an energy difference between the Lowest Unoccupied Molecular Orbital (LUMO) level and the Highest Occupied Molecular Orbital (HOMO) level.

As the substance used for dispersing the stilbene derivative of the present invention, a low molecular compound such as 4,4',4''-tri(N-carbazolyl)triphenylamine (abbr.: TCTA), 1,1-bis[4-(diphenylamino)phenyl]cyclohexane (abbr.: TPAC), 9,9-bis[4-(diphenylamino)phenyl]fluorene (abbr.: TPAF), 4,4'-di(N-carbazolyl)biphenyl (abbr.: CBP), 1,3-bis[5-(p-tert-butylphenyl)-1,3,4-oxadiazol-2-yl]benzene (abbr.: OXD-7), 2,2'2''-(1,3,5-benzenetriyl)tris(1-phenyl-1H-benzimidazole) (abbr.: TBPI), 3-(4-tert-butylphenyl)-4-phenyl-5-(biphenyl-4-yl)-1,2,4-triazole (abbr.: TAZ), or 9,9',9''-[1,3,5-triazine-2,4,6-triyl]tricarbazole (abbr.: TCzTRZ); or a high molecular compound such as poly(N-vinylcarbazole) (abbr.: PVK), poly(4-vinyltriphenylamine) (abbr.: PVTPA), or poly (2,5-pyridinediyl) (abbr.: PPy) can be used. Note that one or more of the foregoing substances are selected and mixed so that the stilbene derivative of the present invention may be in a dispersed state. A layer in which a plurality of any of the foregoing compounds are mixed can be formed by a co-evaporation method. Here, co-evaporation refers to an evaporation method in which raw materials are vaporized from each of evaporation sources provided in one processing chamber, and the vaporized raw materials are mixed in a gas phase so as to be deposited over an object.

Since the stilbene derivative of the present invention has a relatively large energy gap, the stilbene derivative can be used as a substance used for dispersing a light emitting substance. In that case, the light emitting substance is not necessarily the stilbene derivative of the present invention, and a substance capable of emitting light in a desired wavelength may be used. For example, in order to obtain reddish light, any of the following substances exhibiting an emission spectrum with a peak in 600 nm to 650 nm can be used: 4-dicyanomethylene-2-isopropyl-6-[2-(1,1,7,7-tetramethyljulolidin-9-yl)ethenyl]-4H-pyran (abbr.: DCJTI). 4-dicyanomethylene-2-methyl-6-[2-(1,1,7,7-tetramethyljulolidin-9-yl)ethenyl]-4H-pyran (abbr.: DCJT), 4-(dicyanomethylene)-2-tert-butyl-6-[2-(1,1,7,7-tetramethyljulolidin-9-yl)ethenyl]-4H-pyran (abbr.: DCJTB), periflanthene, 2,5-dicyano-1,4-bis[2-(10-methoxy-1,1,7,7-tetramethyljulolidin-9-yl)ethenyl]benzene, or the like. In order to obtain greenish light emission, any of the following substances exhibiting an emission spectrum with a peak in 500 nm to 550 nm can be used: N,N'-dimethylquinacridon (abbr.: DMQd), coumarin 6, coumarin 545T, tris(8-quinolinolato)aluminum (abbr.: Alq₃), N,N'-diphenylquinacridon (DPQd), or the like. In order to obtain bluish light emission, any of the following substances exhibiting an emission spectrum with a peak in 420 nm 500 nm can be used: N,N''-(2-tert-butyl-9,10-anthracenediyldi-4,1-phenylene)bis[N,N',N'-triphenyl-1,4-benzenediamine] (abbr.: DPABPA), 2,5,8,11-tetra(tert-butyl)perylene (abbr.: TBP), perylene, 1,3,6,8-tetraphenylpyrene, or the like.

Although an anode material for forming the first electrode 101 is not particularly limited, a metal, an alloy, a conductive compound, a mixture thereof, or the like having a high work function (work function: 4.0 eV or higher) is preferably used. As specific examples of such an anode material, in addition to indium tin oxide (abbr: ITO), indium tin oxide containing silicon oxide (abbr: ITSO), and indium zinc oxide (abbr: IZO) which is formed using a target in which indium oxide includes zinc oxide (ZnO) at 2 to 20 wt %; gold (Au), platinum (Pt), nickel (Ni), tungsten (W), chromium (Cr), molybdenum (Mo), iron (Fe), cobalt (Co), copper (Cu), palladium (Pd), nitride of a metal material (for example, titanium nitride), or the like can be given.

As a substance for forming the second electrode 102, a metal, an alloy, a conductive compound, a mixture thereof, or the like having a small work function (work function: 3.8 eV or lower) can be used. As a specific example of such a cathode material, an element which belongs to Group 1 or 2 of the Periodic Table, that is, an alkali metal such as lithium (Li) or cesium (Cs), an alkaline earth metal such as magnesium (Mg), calcium (Ca), or strontium (Sr), or an alloy thereof (Mg:Ag, Al:Li) can be given. When an electron generating layer described later is provided between the second electrode 102 and the light emitting layer 113 so as to be stacked with the second electrode, various conductive materials including the material which has been given as the material for the first electrode 101 such as Al, Ag, ITO, or ITSO can be used for the second electrode 102 regardless of the magnitude of the work function.

The first electrode 101 and the second electrode 102 are formed of any of the foregoing anode materials and cathode materials, by an evaporation method, a sputtering method, or the like. Note that the film thickness is preferably 10 to 500 nm.

As shown in FIG. 1, the hole transporting layer 112 may be provided between the first electrode 101 and the light emitting layer 113. Here, the hole transporting layer is a layer having a function of transporting holes injected form the first electrode 101 side to the light emitting layer 113. By providing the hole transporting layer 112, the distance between the first electrode 101 and the light emitting layer 113 can be increased; accordingly, quenching of emitted light due to a metal contained in the first electrode 101 can be prevented. The hole transporting layer is preferably formed of a substance having a high hole transporting property. In particular, a substance having a hole mobility of equal to or higher than $1 \times 10^{-6}$ cm²/Vs is preferable. Note that a substance having a high hole transporting property refers to a substance having higher mobility of holes than of electrons. As specific examples of a substance which can be used for forming the hole transporting layer 112, the following can be given: 4,4'-bis[N-(1-naphthyl)-N-phenylamino]biphenyl (abbr.: NPB), 4,4'-bis[N-(3-methylphenyl)-N-phenylamino]biphenyl (abbr.: TPD), 4,4',4''-tris(N,N-diphenylamino)triphenylamine (abbr.: TDATA), 4,4',4''-tris[N-(3-methylphenyl)-N-phenylamino]triphenylamine (abbr.: MTDATA), 4,4'-bis{N-[4-(N,N-di-m-tolylamino)phenyl]-N-phenylamino)biphenyl (abbr.: DNTPB), 1,3,5-tris[N,N-di(m-tolyl)amino]benzene (abbr.: m-MTDAB), 4,4',4''-tris(N-carbazolyl)triphenylamine (abbr.: TCTA), phthalocyanine (abbr.: H₂Pc), copper phthalocyanine (abbr.: CuPc), or vanadyl phthalocyanine (abbr.: VOPc). The hole transporting layer 112 can be formed to have a multilayer structure formed by combining two or more of layers formed of any of the foregoing substances.

Note that since the stilbene derivative of the present invention has resistance to oxidation, the stilbene derivative can also be used as a material forming the hole transporting layer 112. In that case, the stilbene derivative of the present invention is not necessarily used for the light emitting layer.

As shown in FIG. 1, the electron transporting layer 114 may be provided between the second electrode 102 and the light emitting layer 113. Here, the electron transporting layer is a layer having a function of transporting electrons injected form the second electrode 102 to the light emitting layer 113. By providing electron transporting layer 114, the distance between the second electrode 102 and the light emitting layer 113 can be increased; accordingly, quenching of emitted light due to a metal contained in the second electrode 102 can be prevented. The electron transporting layer is preferably formed of a substance having a high electron transporting property. In particular, a substance having an electron mobility of equal to or higher than $1 \times 10^{-6}$ cm$^2$/Vs are preferable. Note that a substance having a high electron transporting property refers to a substance having higher mobility of electrons than holes. As specific examples of a substance which can be used for forming the electron transporting layer 114, the following can be given: a metal complex such as tris(8-quinolinolato)aluminum (abbr.: Alq$_3$), tris(4-methyl-8-quinolinolato)aluminum (abbr.: Almq$_3$), bis(10-hydroxybenzo[h]-quinolinato)beryllium (abbr.: BeBq$_2$), bis(2-methyl-8-quinolinolato)-4-phenylphenolato-aluminum (abbr.: BAlq), bis[2-(2-hydroxyphenyl)benzoxazolato]zinc (abbr.: Zn(BOX)$_2$), and bis[2-(2-hydroxyphenyl)benzothiazolato]zinc (abbr.: Zn(BTZ)$_2$); 2-(4-biphenylyl)-5-(4-tert-butylphenyl)-1,3,4-oxadiazole (abbr.: PBD), 1,3-bis[5-(p-tert-butylphenyl)-1,3,4-oxadiazol-2-yl]benzene (abbr.: OXD-7), 3-(4-tert-butylphenyl)-4-phenyl-5-(4-biphenylyl)-1,2,4-triazole (abbr.: TAZ), 3-(4-tert-butylphenyl)-4-(4-ethylphenyl)-5-(4-biphenylyl)-1,2,4-triazole (abbr.: p-EtTAZ), bathophenanthroline (abbr.: BPhen), bathocuproin (abbr.: BCP), 4,4-bis(5-methylbenzoxazol-2-yl)stilbene (abbr.: BzOs), and the like. The electron transporting layer 114 can be formed to have a multilayer structure formed by combining two or more of layers formed of any of the foregoing substances.

Note that, the hole transporting layer 112 and the electron transporting layer 114 may be formed using a bipolar substance, instead of the substances given above. A bipolar substance refers to a substance in which a value of a ratio of one carrier mobility to the other carrier mobility is less than or equal to 100, preferably, less than or equal to 10 when carrier mobility of one of electrons and holes is compared with that of the other. As a bipolar substance, for example, 2,3-bis(4-diphenylaminophenyl)quinoxaline (abbr.: TPAQn), or 2,3-bis{4-[N-(1-naphthyl)-N-phenylamino]phenyl}-dibenzo[fh]quinoxaline (abbr.: NPADiBzQn) can be given. Among bipolar substances, a substance with hole or electron mobility of greater than or equal to $1 \times 10^{-6}$ cm$^2$/Vs is preferably used. Further, the hole transporting layer 112 and the electron transporting layer 114 may be formed of the same bipolar substance.

As shown in FIG. 1, the hole injecting layer 111 may be provided between the first electrode 101 and the hole transporting layer 112. The hole injecting layer 111 is a layer having a function of assisting injection of holes from the first electrode 101 to the hole transporting layer 112. By providing the hole injecting layer 111, the difference in ionization potential between the first electrode 101 and the hole transporting layer 112 is relieved, so that holes are easily injected. The hole injecting layer 111 is preferably formed of a substance having smaller ionization potential than a substance which forms the hole transporting layer 112 and having larger ionization potential than a substance which forms the first electrode 101, or a substance in which an energy band is bent when the substance being provided as a thin film with a thickness of 1 to 2 nm between the hole transporting layer 112 and the first electrode 101. As specific examples of a substance which can be used for forming the hole injecting layer 111, a phthalocyanine-based compound such as phthalocyanine (abbr.: H$_2$Pc) or copper phthalocyanine (CuPc), a high molecular compound such as poly(ethylenedioxythiophene)/poly(styrenesulfonic acid) water solution (PEDOT/PSS), or the like can be given. That is, the hole injecting layer 111 can be formed by selecting a substance so that ionization potential of the hole injecting layer 111 is relatively lower than that of the hole transporting layer 112.

As shown in FIG. 1, the electron injecting layer 115 may be provided between the second electrode 102 and the electron transporting layer 114. Here, the electron injecting layer 115 is a layer having a function of assisting injection of electrons from the second electrode 102 to the electron transporting layer 114. By providing the electron injecting layer 115, the difference in electron affinity between the second electrode 102 and the electron transporting layer 114 can be relived, so that electrons are easily injected. The electron injecting layer 115 is preferably formed of a substance having larger electron affinity than a substance which forms the electron transporting layer 114 and having smaller electron affinity than a substance which forms the second electrode 102, or a substance in which an energy band is bent when the substance being provided as a thin film with a thickness of 1 to 2 nm between the electron transporting layer 114 and the second electrode 102. As specific examples of a substance which can be used for forming the electron injecting layer 115, inorganic materials such as alkali metal, alkaline earth metal, alkali metal fluoride, alkaline earth metal fluoride, alkali metal oxide, or alkaline earth metal oxide can be given. In addition to the inorganic material, a substance which can be used to form the electron transporting layer 114 such as BPhen, BCP, p-EtTAZ, TAZ, or BzOs can be selected appropriately and be used as a substance for forming the electron injecting layer 115. That is, the electron injecting layer 115 can be formed by selecting a substance so that electron affinity of the electron injecting layer 115 is relatively higher than that of the electron transporting layer 114.

In the foregoing light emitting element of the present invention, each of the hole injecting layer 111, the hole transporting layer 112, the light emitting layer 113, the electron transporting layer 114, and the electron injecting layer 115 may be formed by any of a vapor deposition method, an ink jetting method, a coating method, or the like.

Further, a hole generating layer may be provided instead of the hole injecting layer 111 and an electron generating layer may be provided instead of the electron injecting layer 115.

Here, the hole generating layer is a layer for generating holes. The hole generating layer can be formed by mixing at least one substance selected from substances having higher mobility of holes than electrons and bipolar substances, with a substance which has an electron accepting property with respect to those substances. As a substance having higher mobility of holes than electrons, a substance similar to a substance which can be used for forming the hole transporting layer 112 can be used. As a bipolar substance, any of the foregoing bipolar substances such as TPAQn can be used. In particular, a substance including a triphenylamine in its skeleton is preferably used among substances having higher mobility of holes than electrons and bipolar substances. When the substance including triphenylamine in its skeleton is used, holes are easily generated. As a substance having an electron accepting property, metal oxide such as molybdenum oxide, vanadium oxide, ruthenium oxide, or rhenium oxide is preferably used. In such a hole generating layer, increase in film thickness does not cause increase in driving voltage; therefore, an optical design which utilizes a microcavity effect and a light interference effect is possible by adjusting the thickness of the hole generating layer. Therefore, a light emitting element with high quality having favorable color purity and a little color change and the like with viewing angle can be formed. In addition, a film thickness can be set so as to prevent short circuit of the first electrode 101 and the second electrode 102 due to affection of unevenness or minute residue remaining on the surface of the electrode 101 generated in the formation.

The electron generating layer is a layer for generating electrons. The electron generating layer can be formed by mixing at least one substance selected from substances having higher mobility of electrons than holes and bipolar substances, with a substance which has an electron accepting property with respect to those substances. As a substance having higher mobility of electrons than holes, a substance similar to a substance which can be used for forming the electron transporting layer 114 can be used. As a bipolar substance, any of the foregoing bipolar substances, such as TPAQn can be used. As a substance having an electron donating property, a substance selected from an alkali metal and an alkaline earth metal, specifically, lithium (Li), calcium (Ca), sodium (Na), potassium (K), magnesium (Mg), and the like can be used. Further, at least one substance selected from alkali metal oxide, alkaline earth metal oxide, alkali metal nitride, alkaline earth metal nitride, and the like, specifically, lithium oxide ($Li_2O$), calcium oxide (CaO), sodium oxide ($Na_2O$), potassium oxide ($K_2O$), and magnesium oxide (MgO) can be used. Furthermore, fluoride such as alkali metal fluoride and alkaline earth metal fluoride, specifically, lithium fluoride (LiF), cesium fluoride (CsF), calcium fluoride ($CaF_2$), or the like can be used.

Note that, in the following description, the hole generating layer is included in the hole injecting layer 111 and the electron generating layer is included in the electron injecting layer 115.

Since the light emitting element described above uses a stilbene derivative of the present invention, the light emitting element can exhibit blue light emission with excellent color purity. In addition, the stilbene derivative of the present invention has excellent resistance to repetition of oxidation reactions; accordingly, reliability of the light emitting element can be improved.

Embodiment Mode 6

A light emitting element of the present invention may include a plurality of light emitting layers. For example, white light emission can be obtained by providing a plurality of light emitting layers and mixing light emission from the light emitting layers. In this embodiment mode, such a light emitting element is described with reference to FIGS. 2 and 3.

Figure 2:
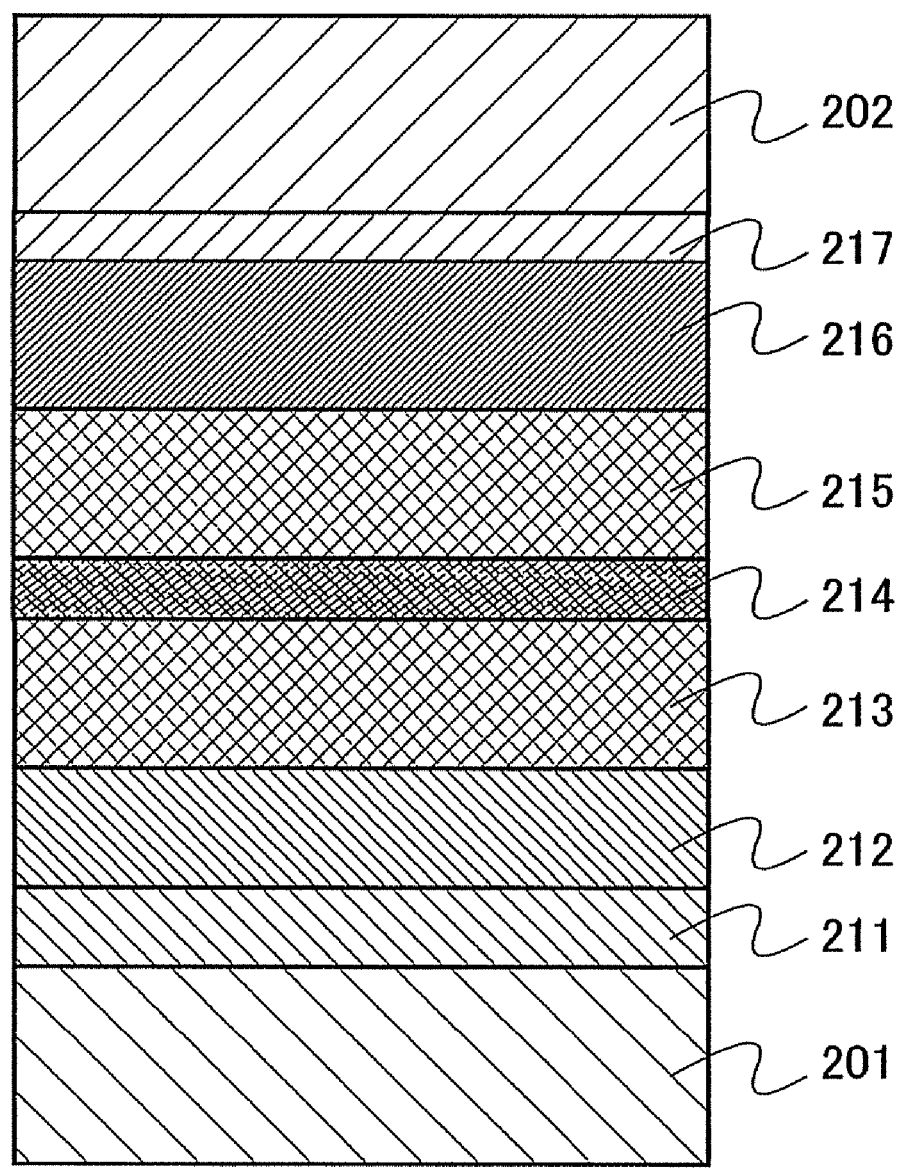
FIG. 2 shows an element structure of a light emitting element of the present invention.

In FIG. 2, a first light emitting layer 213 and a second light emitting layer 215 are provided between a first electrode 201 and a second electrode 202. A spacing layer 214 is preferably provided between the first light emitting layer 213 and the second light emitting layer 215.

When voltage is applied so that electric potential of the second electrode 202 is higher than that of the first electrode 201, current flows between the first electrode 201 and the second electrode 202; so that holes and electrons are recombined with each other in the first light emitting layer 213, the second light emitting layer 215, or the spacing layer 214. Excitation energy generated by recombination in the spacing layer 214 is transferred from the spacing layer 214 to the first light emitting layer 213 and the second light emitting layer 215, so that a first light emitting substance contained in the first light emitting layer 213 and a second light emitting substance contained in the second light emitting layer 215 are excited. The excited first and second light emitting substances emit light while returning to the ground state. Thus obtained light emission colors from the first light emitting layer 213 and the second light emitting layer 215 are emitted outside through either or both the first electrode 201 and the second electrode 202. Light emitted outside from each of the light emitting layers is mixed visually with each other and is recognized as white light; accordingly, white light emission can be obtained.

As the first light emitting layer 213, a layer formed of a stilbene derivative of the present invention or a layer formed in a manner such that the stilbene derivative of the present invention is dispersed in a layer formed of a substance (first host) having a larger energy gap than the stilbene derivative can be used. The second light emitting layer 215 may use a light emitting substance which exhibits a complementary color of the emission color of the first light emitting layer 213. For example, rubrene, or 5,12-bis(1,1-biphenyl-4-yl)-6,11-diphenyltetracene (abbr.: BPT) which exhibit yellow light emission can be used as the light emitting substance. Note that, as also the second light emitting layer 215, a layer which is formed of the light emitting substance or a layer in which the light emitting substance is dispersed in a layer formed of a substance (second host) having a larger energy gap than the light emitting substance may be used. As the first host, substances given in Embodiment Mode 5 can be used. Among the substances, a compound having an electron transporting property, such as OXD-7, TPBI, TAZ, or TCzTRZ are preferable. As the second host, $Alq_3$, $Almq_3$, NPB, TPD, or the like can be used and a compound having a hole transporting property such as NPB or TPB are preferable.

The spacing layer 214 is preferably formed to have functions of transferring energy generated by recombination in the first light emitting layer 213, the second light emitting layer 215, and the spacing layer 214 to both the first light emitting layer 213 and the second light emitting layer 215 and preventing the energy from being transferred to only one of the first light emitting layer 213 and the second light emitting layer 215. Specifically, the spacing layer 214 can be formed of TPAQn, NPB, CBP, TCTA, bis[2-(2-hydroxyphenyl)pyridinato]zinic (abbr.: $Znpp_2$), bis[2-(2-hydroxyphenyl)benzoxazolato]zinc (abbr.: ZnBOX), or the like. By thus providing the spacing layer 214, a problem such that white light emission can not be obtained because of increase in light emission intensity of only one of the first light emitting layer 213 and the second light emitting layer 215 can be prevented.

In addition, as shown in FIG. 2, an electron transporting layer 212 or an electron injecting layer 211 may be provided between the first light emitting layer 213 and the first electrode 201. Further, a hole transporting layer 216 or a hole injecting layer 217 may be provided between the second light emitting layer 215 and the second electrode 202. Note that as substances for forming those layers, any of the substances given in Embodiment Mode 5 can be used.

Although a light emitting element provided with two light emitting layers as in FIG. 2 is described in this embodiment mode, the number of light emitting layers is not limited to two and, for example, may be three. Light emitted from each of the light emitting layers may be mixed in order to make visible white light emission.

Figure 3:
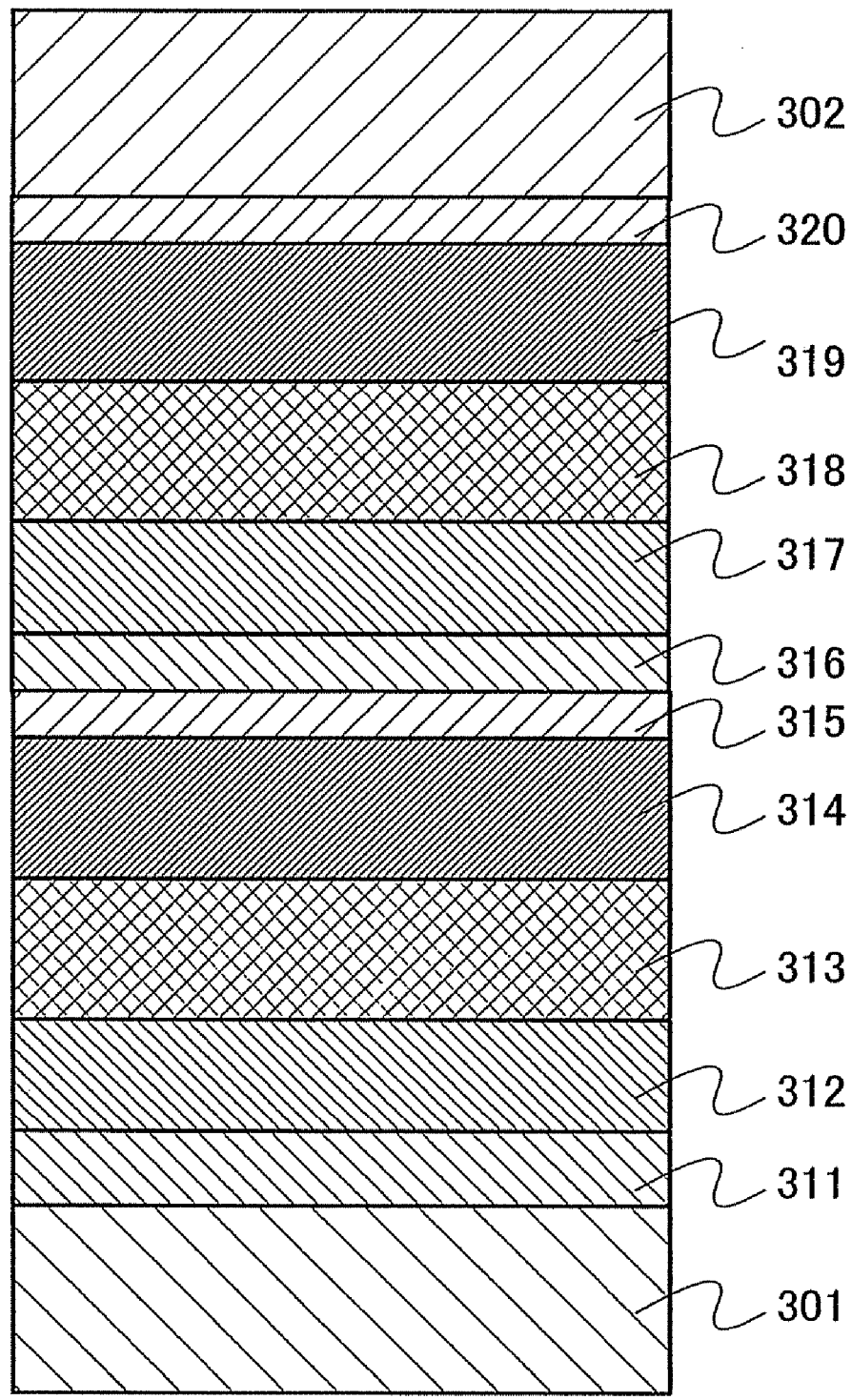
FIG. 3 shows an element structure of a light emitting element of the present invention.

Instead of the light emitting element described with reference to FIG. 2, a light emitting element as shown in FIG. 3 may be employed. In the light emitting element in FIG. 3, a first light emitting layer 313 and a second light emitting layer 318 are provided between a first electrode 301 and a second electrode 302, and a first layer 315 and a second layer 316 are provided between the first light emitting layer 313 and the second light emitting layer 318.

The first layer 315 is a layer for generating holes, whereas the second layer 316 is a layer for generating electrons. When voltage is applied so that electric potential of the second electrode 302 is higher than that of the first electrode 301, electrons injected from the first electrode 301 and holes injected from the first layer 315 are recombined in the first light emitting layer 313, so that a light emitting substance contained in the first light emitting layer 313 emits light. Further, holes injected from the second electrode 302 and electrons injected from the second layer 316 are recombined in the second light emitting layer 318, so that a light emitting substance contained in the second light emitting layer 318 emits light.

The first light emitting layer 313 and the second light emitting layer 318 can be formed of materials similar to the first light emitting layer 213 and the second light emitting layer 215 in FIG. 2, respectively. Light emitted from the first light emitting layer 313 and the second light emitting layer 318 is emitted through either or both the first electrode 301 and the second electrode 302. Light emitted from both of the light emitting layers is visually mixed with each other and is recognized as white light.

The first layer 315 is preferably a layer in which a substance which has a higher transporting property of holes than electrons contains a substance having an electron accepting property with respect to the substance. As a substance having a higher transporting property of holes than electrons, a substance similar to the foregoing substances used for forming the hole transporting layer may be used. As a substance having an electron accepting property with respect to the substance having a higher transporting property of holes than electrons, molybdenum oxide, vanadium oxide, 7,7,8,8-tetracyanoquinodimethane (abbr.: TCNQ), 2,3,5,6-tetrafluoro-7,7,8,8-tetracyanoquinodimethane (abbr.: $F_4$-TCNQ), or the like can be used.

The second layer 316 is preferably is a layer in which a substance which has a higher transporting property of electrons than holes contains a substance having an electron donating property with respect to the substance. As a substance having a higher transporting property of electrons than holes, a substance similar to the foregoing substances used for forming the electron transporting layer may be used. As a substance having an electron donating property to the substance having a higher transporting property of electrons than holes, an alkali metal such as lithium or cesium, an alkaline earth metal such as magnesium or calcium, a rare earth metal such as erbium or ytterbium, or the like can be used.

As shown in FIG. 3, an electron transporting layer 312 and an electron injecting layer 311 may be provided between the first light emitting layer 313 and the first electrode 301. Further, a hole transporting layer 314 may be provided between the first light emitting layer 313 and the first layer 315. In addition, a hole transporting layer 319 and a hole injecting layer 320 may be provided between the second light emitting layer 318 and the second electrode 302. In addition, an electron transporting layer 317 may be formed between the second light emitting layer 318 and the second layer 316.

Although a light emitting element provided with two light emitting layers as in FIG. 3 is described in this embodiment mode, the number of light emitting layers is not limited to two and, for example, may be three. Light emitted from each of the light emitting layers may be mixed in order to be recognized as white light.

Note that, although a structure of a light emitting element in which light is emitted only from the light emitting layer is shown in this embodiment mode, the light emitting element may be designed so that light is emitted also from another functional layer (such as the electron transporting layer or the hole transporting layer). For example, when a dopant is added to the electron transporting layer and the hole transporting layer, light can be emitted from the transporting layers. When light emission wavelength of a light emitting material for the light emitting layer and that of the transporting layers are different, light emission having a spectrum in which these wavelengths are overlapped with each other can be obtained. Therefore, when emission colors of the light emitting layer and the transport layers are complementary colors with each other, white light emission can be obtained.

Note that this embodiment mode can be appropriately combined with any of other embodiment modes and any of the following embodiments.

Embodiment Mode 7

In this embodiment mode, a light emitting device to which the present invention is applied is described with reference to FIGS. 4A and 4B. Note that FIG. 4A is a top view showing the light emitting device and FIG. 4B is a cross-sectional view along an A-A' line (a cross-sectional view taken along a line A-A') in FIG. 4A. In each of FIGS. 4A and 4B, corresponding portions are denoted by the same reference numerals. Reference numeral 400 denotes a substrate. Reference numeral 401 denotes a driver circuit portion (a source side driver circuit); 402, a pixel portion; and 403, a driver circuit portion (a gate side driver circuit), which are indicated by dashed lines. Reference numeral 404 denotes a sealing substrate and 405 denotes a sealant.

Note that 407 denotes a wire for transmitting a signal to be inputted to the source side driver circuit 401 or the gate side driver circuit 403 and receives a video signal, a clock signal, a start signal, a reset signal, or the like from an FPC (flexible printed circuit) 408 that is an external input terminal. Note that although only the FPC is shown here, the FPC may be provided with a printed wiring board (PWB). The light emitting device of the present invention includes not only a light emitting device itself but also a light emitting device with an FPC or a PWB attached thereto.

A cross-sectional structure is described with reference to FIG. 4B. The driver circuit portion and the pixel portion are formed over the substrate 400. Here, the source side driver circuit 401, which is a driver circuit portion, and the pixel portion 402 are shown.

Note that the source side driver circuit 401 is formed of a CMOS circuit in which an n-channel thin film transistor 421 and a p-channel thin film transistor 421 are combined. Alternatively, the driver circuit including a thin film transistor may be formed by a known CMOS circuit, PMOS circuit, or NMOS circuit. Although a driver integration type in which a driver circuit is formed over a substrate is described in this embodiment mode, it is not always necessary and the driver circuit can be formed outside the substrate.

The pixel portion 402 includes a plurality of pixels each including a switching thin film transistor 411, a thin film transistor 412 for controlling current, and a first electrode 413 electrically connected to a drain of the thin film transistor 412. Note that an insulator 414 is formed to cover an end of the first electrode 413.

For preferable formation of a layer 415 including a light emitting substance which is to be formed later, the insulator 414 is preferably formed so that either or both an upper end and a lower end thereof are curved with curvature. For example, when positive type photosensitive acrylic is used as a material for the insulator 414, the insulator 414 preferably has a curved surface with a curvature radius (0.2 µm to 3 µM) only as the upper end. As for the insulator 414, a photosensitive negative type which becomes insoluble in an etchant by light irradiation or a positive type which becomes soluble in an etchant by light irradiation can be used. Further, not only an organic material, but an inorganic material such as silicon oxide or silicon oxynitride can be used as a material for the insulator 414.

The layer 415 including a light emitting substance and a second electrode 416 are formed over the first electrode 413.

A light emitting element 417 including the first electrode 413, the layer 415 including a light emitting substance, and the second electrode 416 is a light emitting element having a stilbene derivative of the present invention. As long as the layer 415 including a light emitting substance includes a light emitting layer containing at least one of stilbene derivatives represented by the general formulae (G1) and (G2), a stacked-layer structure of another layer is not particularly limited. Note that each of the first electrode 413, the layer 415 including a light emitting substance, and the second electrode 416 can be formed of a material which is appropriately selected from those given in Embodiment Mode 5.

By attaching the sealing substrate 404 and the substrate 400 with the sealant 405, a structure is formed, in which the light emitting element 417 is provided in a space 406 surrounded by the substrate 400, the sealing substrate 404, and the sealant 405. Note that the space 406 may be filled with an inert gas (such as nitrogen and argon) and the space 406 may be filled with the sealant 405.

An epoxy-based resin is preferably used as the sealant 405. The material preferably allows as little moisture and oxygen as possible to penetrate. As a material for the sealing substrate 404, a plastic substrate formed of FRP (Fiberglass-Reinforced Plastics), PVF (polyvinyl fluoride), polyester, acrylic, or the like can be used as well as a glass substrate or a quartz substrate. In the foregoing manner, a light emitting device can be formed.

Note that, when both the first electrode 413 and the second electrode 416 are formed of a light transmitting substance, emitted light can be extracted from both the first electrode 413 side and the second electrode 416 side. When only the second electrode 416 is formed of a light transmitting substance, emitted light can be extracted only from the second electrode 416 side. In this case, it is preferable that the first electrode 413 which is formed of a material with high reflectance, or a film formed of a material with high reflectance (a reflection film) be provided under the first electrode 413. When only the first electrode 413 is formed of a light transmitting substance, emitted light can be extracted from the first electrode 413 side. In this case, the second electrode 416 is preferably formed of a material with high reflectance, or a reflection film is preferably provided over the second electrode 416.

In the light emitting element 417, the layer 415 including a light emitting substance may have such a stacked structure as to operate when voltage is applied so that electric potential of the second electrode 416 is higher than that of the first electrode 413. Alternatively, in the light emitting element 417, the layer 415 including a light emitting substance may have such a stacked structure as to operate when voltage is applied so that electric potential of the second electrode 416 is lower than that of the first electrode 413.

Since the light emitting device of the present invention uses a stilbene derivative of the present invention as a light emitting substance, the light emitting device can emit blue light with excellent color purity. Accordingly, a light emitting device capable of showing an image superior in color can be provided.

Note that although an active matrix light emitting device, in which drive of a light emitting element is controlled by a transistor, is described in this embodiment mode; a passive matrix light emitting device, in which a light emitting element is driven without particularly providing a driving element such as a thin film transistor in each pixel, may alternatively be employed.

Note that this embodiment mode can be appropriately combined with any of Embodiment Modes 1 to 6 and any of the following embodiments.

Embodiment Mode 8

Figure 5A:
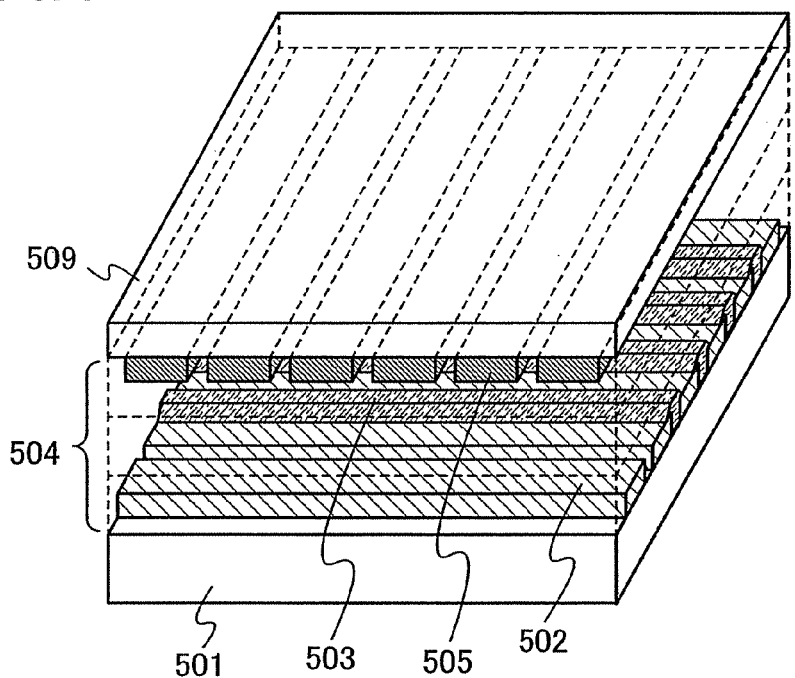
FIGS. 5A and 5B are views of a light emitting device using a light emitting element of the present invention.
Figure 5B:
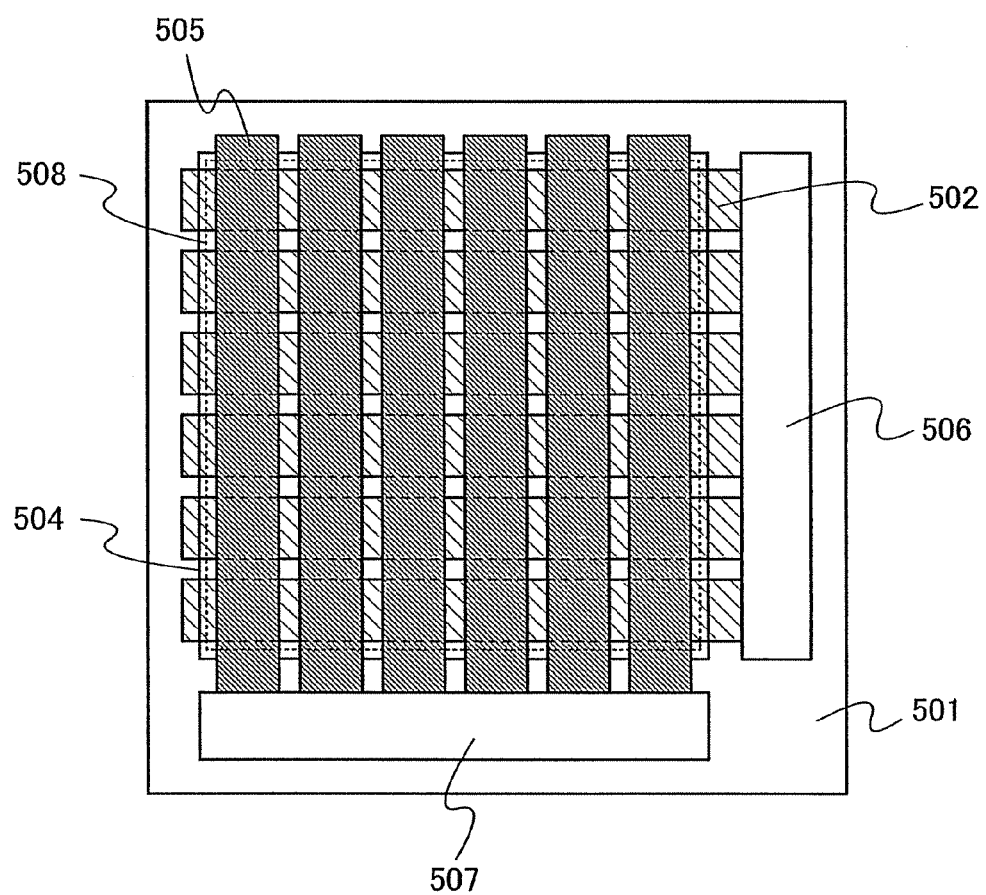

In this embodiment mode, a passive matrix light emitting device to which the present invention is applied is described with reference to FIGS. 5A and 5B. FIGS. 5A and 5B show a perspective view and a top view of the passive matrix light emitting device to which the present invention is applied, respectively. Note that FIG. 5A is a perspective view of a portion surrounded by a dashed line 508 in FIG. 5B. In FIGS. 5A and 5B, the same reference numerals denote the same portions. In FIG. 5A, a plurality of first electrodes 502 are formed in parallel with one another over a first substrate 501. Each edge portion of the first electrodes 502 is covered with a partition layer 503. The frontmost first electrode 502 also has an edge portion covered with the partition layer 503, which is not shown in FIG. 5A for a simpler description on a manner of an arrangement of the first electrodes 502 and the partition layers 503 over the first substrate 501. A plurality of second electrodes 505 are formed above the first electrodes 502 in parallel with one another so as to intersect with the first electrodes 502. A layer 504 including a light emitting substance is formed between the first electrodes 502 and the second electrodes 505. A portion in which the first electrode 502 and the second electrode 505 intersect forms a light emitting element of the present invention, in which the layer 504 including a light emitting substance is provided between the electrodes. As long as the layer 504 including a light emitting substance includes a light emitting layer containing at least one of stilbene derivatives represented by the general formulae (G1) and (G2), a stacked-layer structure of another layer is not particularly limited. Note that each of the first electrode 502, the layer 504 including a light emitting substance, and the second electrode 505 can be formed of a material which is appropriately selected from those given in Embodiment Mode 5. A second substrate 509 is provided over the second electrode 505.

As shown in FIG. 5B, the first electrode 502 is connected to a first driver circuit 506 and the second electrode 505 is connected to a second driver circuit 507. A light emitting element of the present invention selected according to a signal from the first driver circuit 506 and the second driver circuit 507 emits light. The emitted light is extracted outside through the first electrode 502 and/or the second electrode 505. Light emission from a plurality of the light emitting elements is combined with each other to display an image. Note that, in FIG. 5B, the partition layer 503 and the second substrate 509 are not shown for a simpler description on the arrangement of the first electrodes 502 and the second electrodes 505.

When both the first electrode 502 and the second electrode 505 are formed of a light transmitting substance, emitted light can be extracted through both the first electrode 502 and the second electrode 505. When only the second electrode 505 is formed of a light transmitting substance, emitted light can be extracted only from the second electrode 505 side. In this case, it is preferable that the first electrode 502 which is formed of a material with high reflectance, or a film formed of a material with high reflectance (a reflection film) be provided under the first electrode 502. When only the first electrode 502 is formed of a light transmitting substance, emitted light can be extracted only from the first electrode 502 side. In this case, the second electrode 505 is preferably formed of a material with high reflectance or a reflection film is preferably provided over the second electrode 505. The partition layers 503 can be formed of a material similar to those of the insulator 414 given in Embodiment Mode 7.

Since the light emitting device of the present invention uses a stilbene derivative of the present invention as a light emitting substance, the light emitting device can emit blue light with excellent color purity. Accordingly, a light emitting device capable of showing an image superior in color can be provided.

Note that this embodiment mode can be appropriately combined with any of Embodiment Modes 1 to 6 and any of the following embodiments.

Embodiment Mode 9

In this embodiment mode, various electronic appliances which are completed by using a light emitting device having a light emitting element of the present invention are described. Since the light emitting device of the present invention uses a stilbene derivative of the present invention as a light emitting substance, the light emitting device can emit blue light with excellent color purity. Accordingly, an electronic appliance capable of showing an image superior in color can be provided.

As an electronic appliance manufactured using a light emitting device of the present invention, the following can be given: a television, a camera such as a video camera or a digital camera, a goggle type display (a head mounted display), a navigation system, an audio reproducing device (such as a car audio and an audio component stereo), a notebook personal computer, a game machine, a portable information terminal (such as a mobile computer, a portable phone, a portable game machine, and an electronic book), an image reproducing device provided with a recording medium (specifically, a device for reproducing a recording medium such as a digital video disc (DVD), which has a display device for displaying the reproduced image) and the like. FIGS. 6A to 6E show specific examples of such electronic appliances. The electronic appliances using the light emitting device of the present invention is not limited to the specific examples.

Figure 6A:
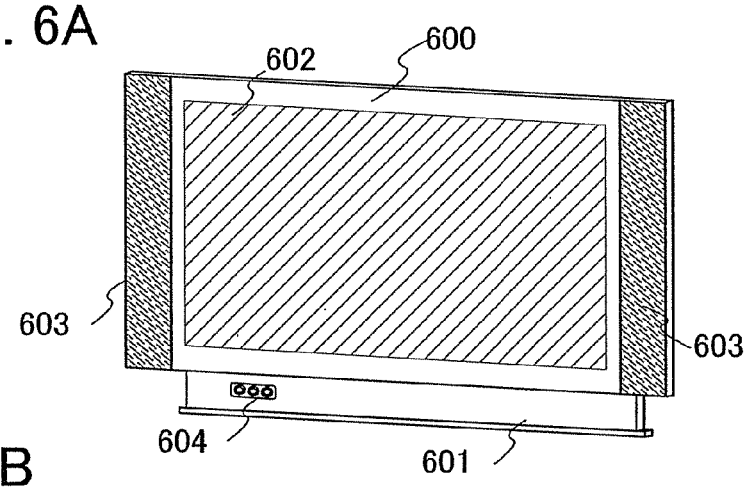
FIGS. 6A to 6E are views each showing an electronic appliance using the light emitting element of the present invention.

FIG. 6A shows a display device including a housing 600, a support base 601, a display portion 602, a speaker portion 603, a video input terminal 604, and the like. The display device is manufactured using a light emitting device of the present invention in the display portion 602. Note that the display device includes all devices for displaying information such as for a personal computer, for receiving TV broadcasting, and for displaying an advertisement.

A light emitting element of the present invention is provided in the display portion 602. A layer including a light emitting substance provided in the light emitting element has a light emitting layer which contains at least one of stilbene derivatives represented by the general formulae (G1) and (G2). Therefore, by using a light emitting element of the present invention, a display device capable of showing blue light with excellent color purity and an image superior in color can be provided.

Figure 6B:
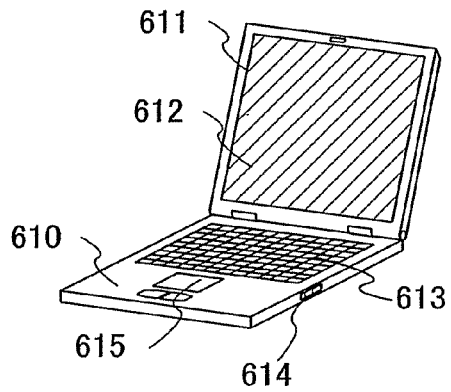

FIG. 6B shows a notebook personal computer including a main body 610, a housing 611, a display portion 612, a keyboard 613, an external connection port 614, a pointing device 615, and the like.

A light emitting element of the present invention is provided in the display portion 612. A layer including a light emitting substance provided in the light emitting element has a light emitting layer which contains at least one of stilbene derivatives represented by the general formulae (G1) and (G2). Therefore, by using a light emitting element of the present invention, a notebook personal computer capable of showing blue light with excellent color purity and an image superior in color can be provided.

Figure 6C:
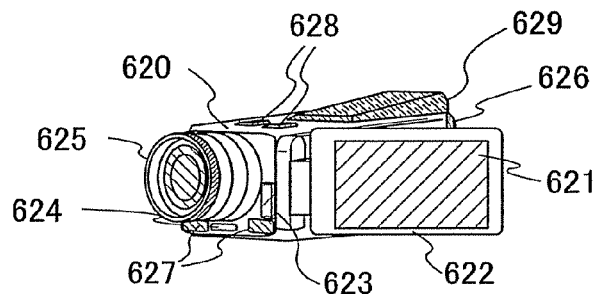

FIG. 6C shows a video camera including a main body 620, a display portion 621, a housing 622, an external connection port 623, a remote control receiving portion 624, an image receiving portion 625, a battery 626, an audio input portion 627, an operation key 628, an eyepiece portion 629, and the like.

A light emitting element of the present invention is provided in the display portion 621. A layer including a light emitting substance provided in the light emitting element has a light emitting layer which contains at least one of stilbene derivatives represented by the general formulae (G1) and (G2). Therefore, by using a light emitting element of the present invention, a video camera capable of showing blue light with excellent color purity and an image superior in color can be provided.

Figure 6D:
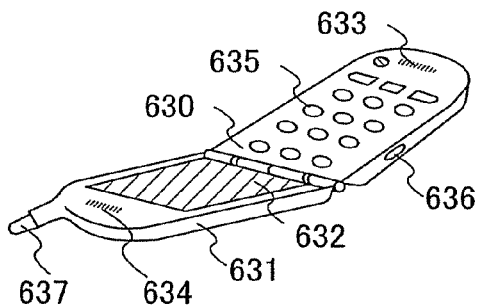

FIG. 6D shows a portable phone including a main body 630, a housing 631, a display portion 632, an audio input portion 633, an audio output portion 634, an operation key 635, an external connection port 636, an antenna 637, and the like.

A light emitting element of the present invention is provided in the display portion 632. A layer including a light emitting substance provided in the light emitting element has a light emitting layer which contains at least one of stilbene derivatives represented by the general formulae (G1) and (G2). Therefore, by using a light emitting element of the present invention, a portable phone capable of showing blue light with excellent color purity and an image superior in color can be provided.

Figure 6E:
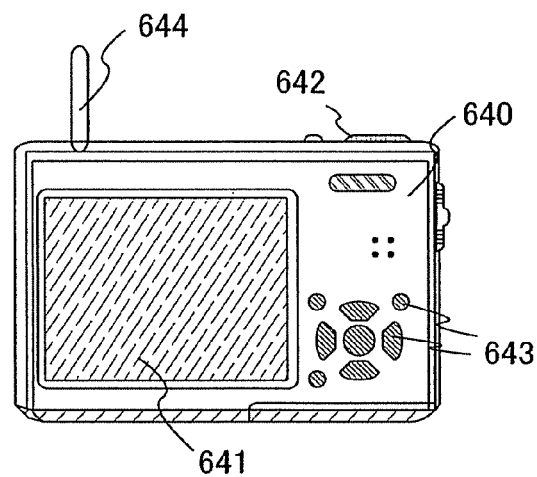

FIG. 6E shows a digital camera, including a main body 640, a display portion 641, a shutter button 642, an operation key 643, an antenna 644, an imaging portion, and the like. Note that FIG. 6E shows the digital camera seen from the display portion 641 side, and the imaging portion is not shown.

The digital camera of the present invention may receive signals such as an image signal or an audio signal via the antenna 644 and the display portion 641 may serve as a display medium such as a TV receive. Note that a speaker, an operation switch, and the like may be appropriately provided when the digital camera serves as a display medium.

A light emitting element of the present invention is provided in the display portion 641. A layer including a light emitting substance provided in the light emitting element has a light emitting layer which contains at least one of stilbene derivatives represented by the general formulae (G1) and (G2). Therefore, by using a light emitting element of the present invention, a digital camera capable of showing blue light with excellent color purity and an image superior in color can be provided.

As described above, the applicable range of the present invention is so wide that the present invention can be applied to display devices of various fields. Further, the electronic appliance of this embodiment mode can be appropriately combined with any of the structures described in Embodiment Modes 1 to 8 and any of the following embodiments.

Embodiment 1

A synthesis example of a stilbene derivative of the present invention is described. Note that the present invention is not limited to the synthesis example given below.

Synthesis Example 1

A synthesis method of (E)-4,4'-bis[4-(carbazol-9-yl)phenyl]stilbene (abbr.: CzP$_2$S), which is represented by the structural formula (13), is described.

First, 25.2 g (101 mmol) of 4-bromobenzyl bromide and 100 mL of acetone were put into a 200 mL conical flask, and 29.1 g (111 mmol) of triphenylphosphine was added thereto. The mixture was stirred for 23 hours at room temperature. After the reaction, a precipitate in the reaction mixture was collected by suction filtration to give 50.5 g of a white powdered solid of (4-bromobenzyl)triphenylphosphoniumbromide (yield: 97.6%). A synthesis scheme (f-1) of (4-bromobenzyl)triphenylphosphoniumbromide is shown below.

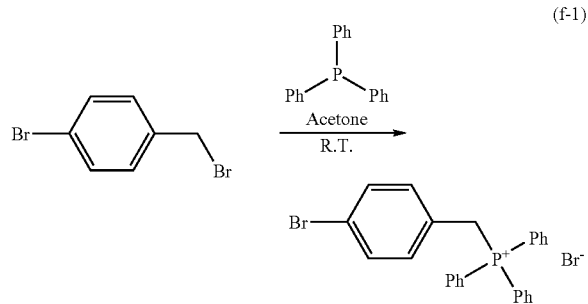

(f-1)

Next, 50.2 g (97.9 mmol) of (4-bromobenzyl)triphenylphosphoniumbromide, which is obtained above, and 21.7 g (118 mmol) of 4-bromobenzaldehyde were put into a 500 mL three-neck flask, and then the air in the flask was replaced with nitrogen. Then, 200 mL of tetrahydrofuran (THF) was added thereto. Then, a suspension in which 13.2 g (118 mmol) of potassium tert-butoxide was dissolved in 100 mL of THF was dropped to this mixture. After the dropping, the reaction mixture was stirred for 24 hours at room temperature. After the reaction, water was added to the reaction mixture, and a precipitate was collected by suction filtration to give 14.0 g of a white powdered solid of (E)-4-4'-dibromostilbene (yield: 42.1%). Further, it is possible to obtain (Z)-4,4'dibromostilbene by the following method. From the filtrate which is obtained by the foregoing suction filtration, a product was extracted with ethyl acetate. The obtained extraction solution was dried with magnesium sulfate. Then, the mixture was suction filtrated, and the filtrate was concentrated. The obtained residue was purified by silica gel column chromatography (developing solution: toluene). Then, the obtained solution was concentrated to give 14.8 g of a light yellow solid of (Z)-4,4'dibromostilbene (yield: 45%). A synthesis scheme (f-2) of 4,4'dibromostilbene is shown below. Note that (E)-4-4'-dibromostilbene is used in this embodiment.

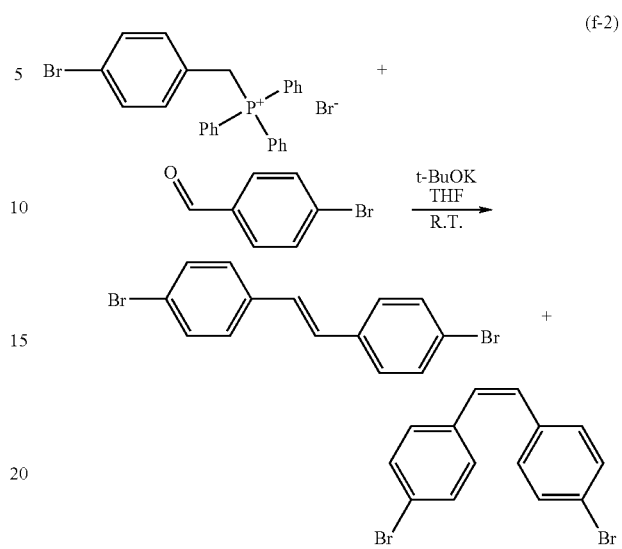

(f-2)

Then, 21.8 g (67.5 mmol) of 9-(4-bromophenyl)carbazole was put into a 500 mL three-necked flask, and the air in the flask was replaced with nitrogen. Then, 200 mL of tetrahydrofuran (THF) was added thereto. The temperature in the flask was set to be −78° C. and then, 48.9 mL (74.3 mmol) of n-butyllithium (1.52 mol/L, hexane solution) was dropped to the mixture and was stirred for 2 hours at the same temperature. Then, 17.4 mL (155 mmol) of trimethyl borate was added thereto. The mixture was stirred for one hour at the same temperature, then, was stirred for 24 hours while raising the temperature to room temperature. After the reaction, 200 mL of hydrochloric acid (1.0 mol/L) was added to the reaction mixture, and then stirred for one hour at room temperature. After that, the organic layer in the reaction mixture was washed with water and the product was extracted with ethyl acetate from the water which was used for the washing. The obtained extraction solution and the organic layer, which was washed with water, were mixed. The mixture was further washed with a saturated aqueous solution of sodium chloride, and then dried with magnesium sulfate. After the drying, the mixture was suction filtrated, and the filtrate was concentrated. The obtained residue was recrystallized with a mixed solvent of chloroform and hexane to give 12.8 g of a white powdered solid of 4-(carbazol-9-yl)phenylboronic acid (yield: 65.9%). A synthesis scheme (f-3) of 4-(carbazol-9-yl)phenylboronic acid is shown below.

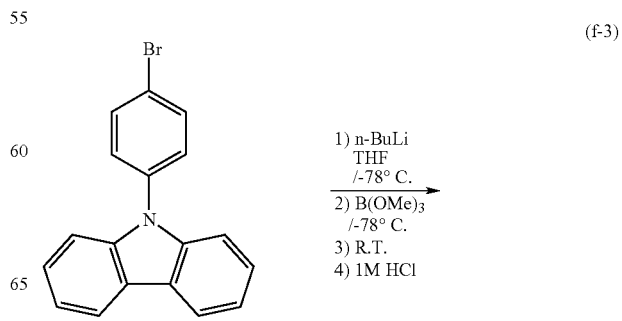

(f-3)

-continued

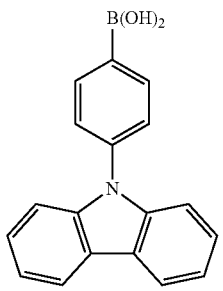

Then, 2.0 g (5.9 mmol) of (E)-4-4'-dibromostilbene and 3.7 g (13 mmol) of 4-(carbazol-9-yl)phenylboronic, which were obtained as described above, and 0.013 g (0.059 mmol) of palladium acetate (II) and 0.12 g (0.41 mmol) of tris(ortho-tolyl)phosphine were put into a 100 mL three-necked flask, and the air in the flask was replaced with nitrogen. Then, 30 mL of ethylene glycol dimethyl ether (DME) and 9 mL (17 mmol) of potassium carbonate solution (2.0 mol/L) were added to the mixture. The mixture was refluxed for 6 hours at 90° C. After the reaction, a precipitate in the reaction mixture was collected by suction filtration. The obtained solid was washed with toluene to give 2.3 g of a light yellow powdered solid (yield: 59%). Note that the light yellow powdered solid was identified as (E)-4,4'-bis[4-(carbazol-9-yl)phenyl]stilbene (abbr.: $CzP_2S$) by a nuclear magnetic resonance (NMR) method. A synthesis scheme (f-4) of (E)-4,4'-bis[4-(carbazol-9-yl)phenyl]stilbene is shown below.

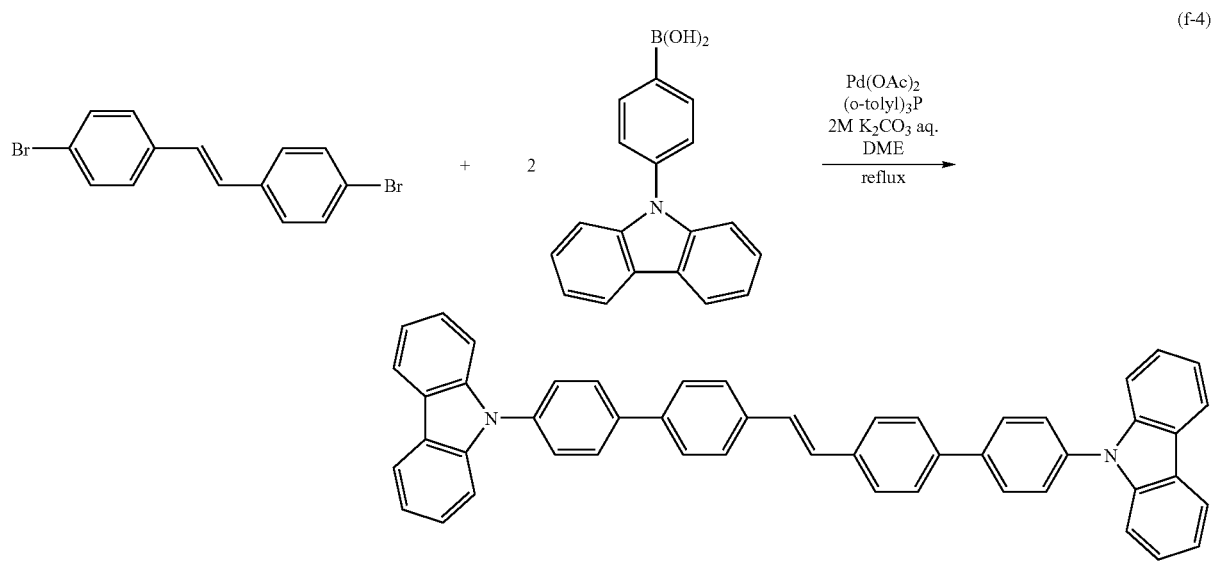

(f-4)

Figure 7A:
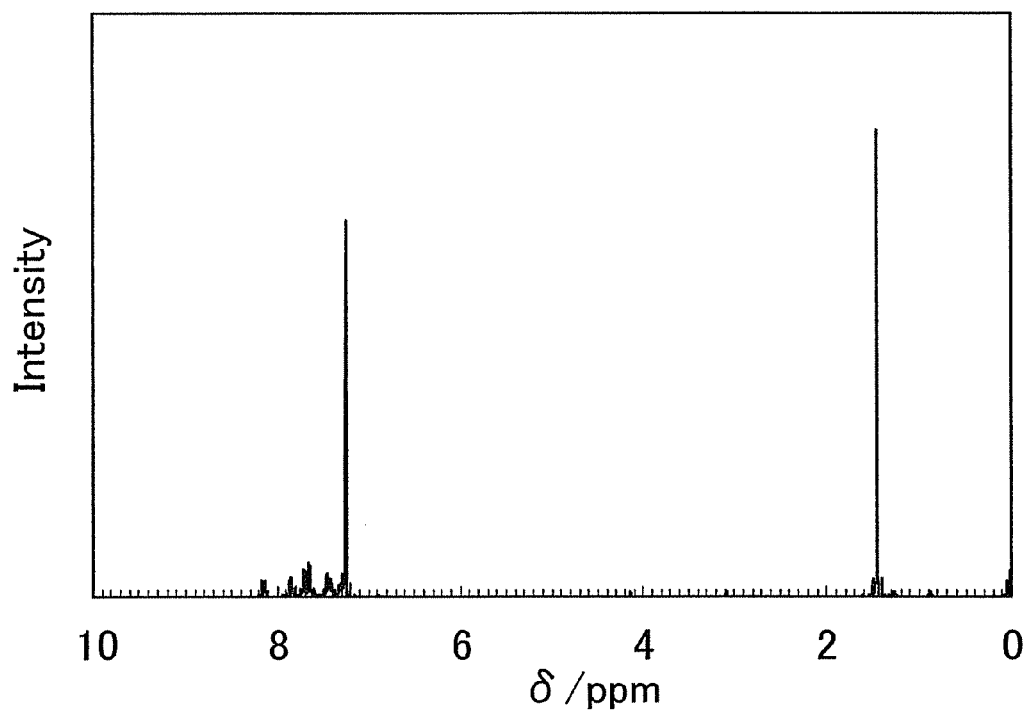
FIGS. 7A and 7B are $^1$H NMR charts of a stilbene derivative (CzP$_2$S) obtained in Synthesis Example 1.
Figure 7B:
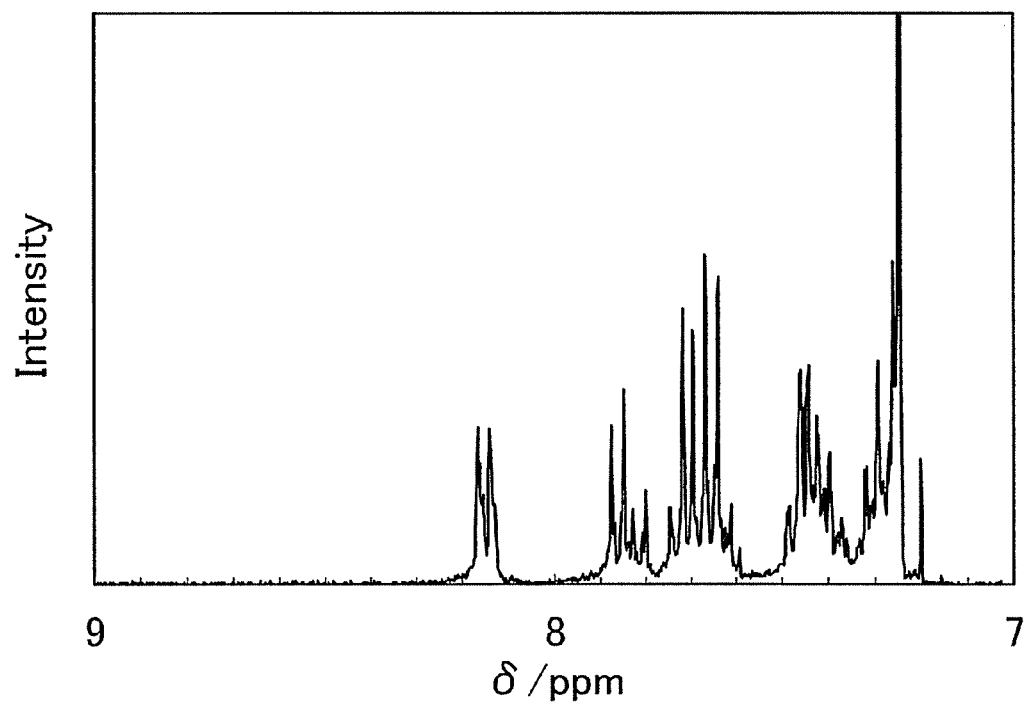

$^1$H NMR of the compound is shown below. A $^1$H NMR chart is shown in each of FIGS. 7A and 7B. The range of 7.0 ppm to 9.0 ppm in FIG. 7A is expanded and shown FIG. 7B.

$^1$H NMR (CDCl$_3$, 300 MHz): δ=7.26-7.33 (m, 7H), 7.36-7.48 (m, 9H), 7.59-7.75 (1 m, 10H), 7.80-7.88 (m, 4H), 8.14-8.17 (m, 4H).

2.3 g of the obtained (E)-4,4'-bis[4-(carbazol-9-yl)phenyl] stilbene (abbr.: $CzP_2S$) was heated to 360° C. and was purified by sublimation under a condition where a pressure was 7.8 Pa and an argon flow rate was 3.0 mL/min, so that 1.61 g was recovered and the recovery rate was 70%.

Figure 8:
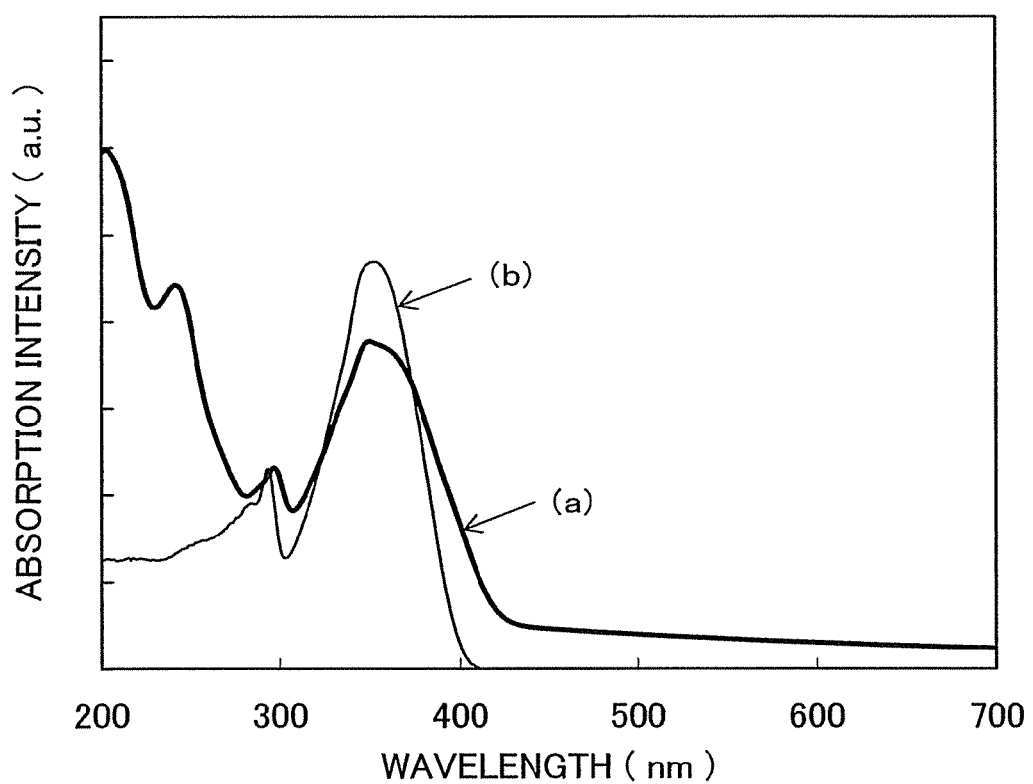
FIG. 8 is a graph showing an absorption spectrum of CzP$_2$S.

An absorption spectrum of $CzP_2S$ is shown in FIG. 8. The ultraviolet-visible spectrophotometer (manufactured by JASCO Corporation, V-550) was used for the measurement. In FIG. 8, the horizontal axis indicates a wavelength (nm) and the vertical axis indicates absorption intensity (arbitrary unit (a.u.)). Note that, in FIG. 8, (a) indicates the absorption spectrum in a state where $CzP_2S$ is a thin film whereas (b) indicates the absorption spectrum in a state where $CzP_2S$ is dissolved in a toluene solution. Note that each of the samples was formed by putting the solution in a quartz cell and by forming the film on a quartz substrate by evaporation. Absorption spectra of the samples, from each of which an absorption spectrum of quartz was subtracted, are shown. An energy gap of $CzP_2S$ was found to be 3.09 eV, using a tauc plot, according to the absorption spectrum in the thin film state ((a) in FIG. 8).

Figure 9:
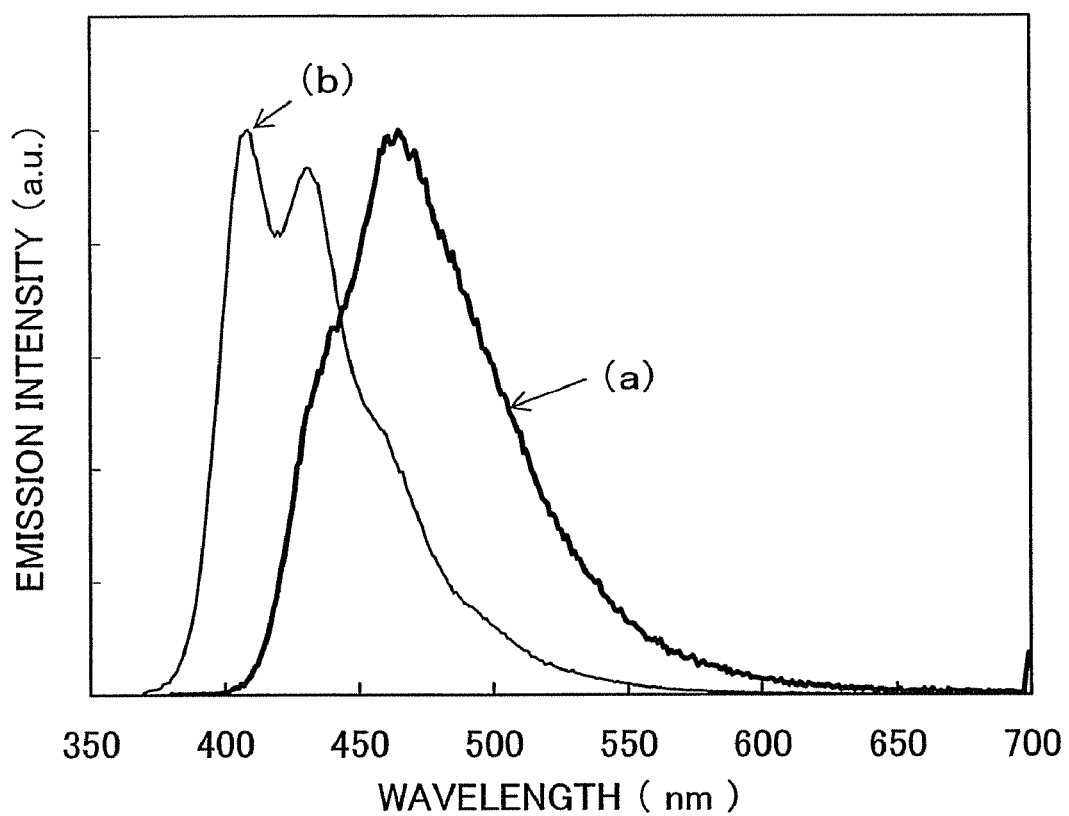
FIG. 9 is a graph showing an emission spectrum of CzP$_2$S.

An emission spectrum of $CzP_2S$ is shown in FIG. 9. In FIG. 9, the horizontal axis indicates a wavelength (nm) and the vertical axis indicates emission intensity (arbitrary unit). In FIG. 9, (a) indicates the emission spectrum in a state where $CzP_2S$ is a thin film (excitation wavelength: 350 nm), whereas (b) indicates the emission spectrum in a state where $CzP_2S$ is dissolved in a toluene solution (excitation wavelength: 352 nm). It is found according to FIG. 9 that light emission from $CzP_2S$ has a peak at 465 nm in the thin film state and has peaks at 408 nm and 431 nm in the toluene solution. These light emission was recognized as blue light emission.

A film of the obtained $CzP_2S$ was formed by an evaporation method. An ionization potential of the compound in the thin film state was measured with a photoelectron spectrometer (manufactured by Riken Keiki Co., Ltd., AC-2) and was found to be 5.36 eV. Accordingly, the HOMO level was found to be −5.36 eV. In addition, the LUMO level, which was obtained by using the energy gap (3.09 eV), was found to be −2.27 eV.

Thermogravimetry-Differential Thermal Analysis (TG-DTA) of the obtained $CzP_2S$ was carried out. The measurement was conducted using a thermo-gravimetric/differential thermal analyzer (manufactured by Seiko Instruments Inc., TG/DTA-320). The temperature at which the weight was reduced to be less than or equal to 95% of the weight at the beginning of the measurement was 479.4° C. In addition, the melting point of CzP$_2$S was 348° C. in a measurement using a melting point apparatus (manufactured by As One Corporation, ATM-01).

An oxidation reaction property of CzP$_2$S was measured by a cyclic voltammetry (CV) measurement. Note that an electrochemical analyzer (manufactured by BAS Inc., ALS model 600A) was used for the measurement.

The solution for the CV measurement was prepared by dissolving supporting electrolyte of tetra-n-butylammonium perchlorate (n-Bu$_4$NClO$_4$) in a solvent of dehydrated dimethylformamide (DMF) so as to make a solution with a concentration of 100 mmol/L, and by further dissolving CzP$_2$S, the material to be measured, to a concentration of 1 mmol/L. A platinum electrode (manufactured by BAS Inc., PTE platinum electrode) was used as an indicator electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-5 Reference electrode for nonaqueous solvent) was used as a reference electrode.

The oxidation reaction property was measured as follows. The electric potential of the indicator electrode with respect to the reference electrode was changed from −0.20 to 1.20 V, and then, from 1.20 to −0.20 V. A scan for the change was set as 1 cycle, and 100 cycles were measured. The CV measurement was carried out with a scan speed of 0.1 V/s.

Figure 10:
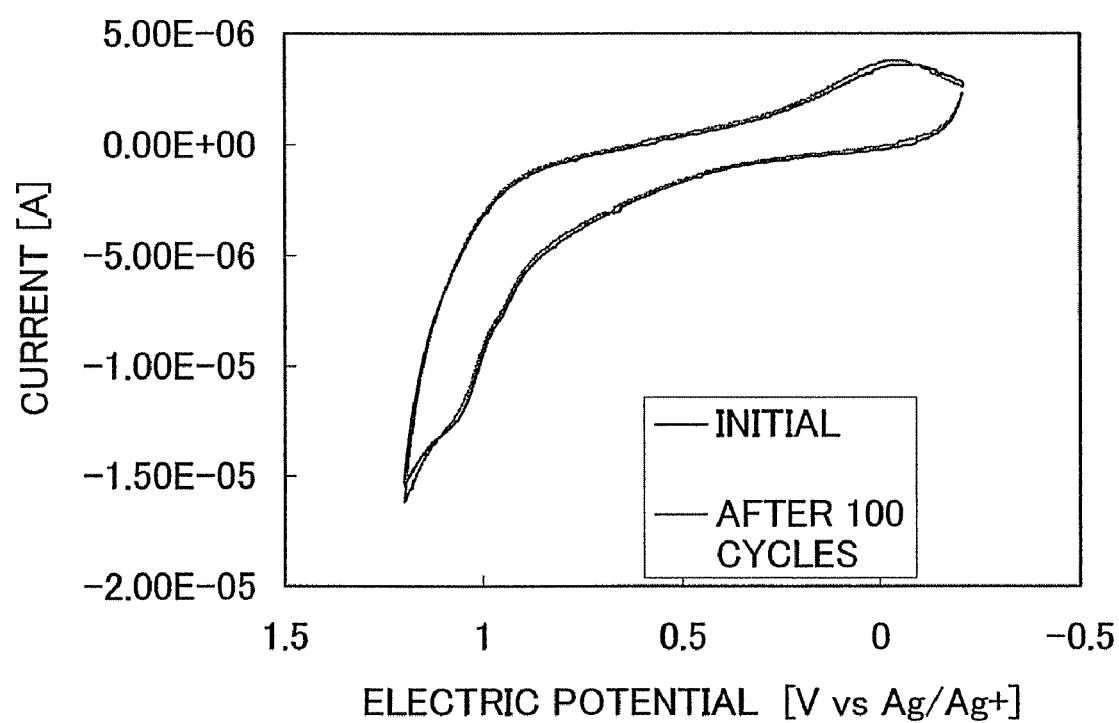
FIG. 10 is a graph showing a measurement result of cyclic voltammetry (CV) on CzP$_2$S.

FIG. 10 shows the result of the measurement of the oxidation reaction property of CzP$_2$S. In FIG. 10, the horizontal axis indicates electric potential (V) of the indicator electrode with respect to the reference electrode and the vertical axis indicates a current value (A) flowing between the reference electrode and the auxiliary electrode.

FIG. 10 shows that the electric potential is approximately 0.90 to 1.00V and approximately 1.00 to 1.10 (vs. Ag/Ag$^+$ electrode) when current which indicates oxidation in the cyclic voltammetry becomes maximum (hereinafter, referred to as oxidation peak potential). In addition, although the scan was repeated for 100 cycles, the peak position and the peak intensity of the CV curve hardly changed. Therefore, it is found that a stilbene derivative of the present invention is quite stable with respect to oxidation reaction.

As described above, the stilbene derivative of the present invention can exhibit blue light emission with excellent color purity. Accordingly, the stilbene derivative is highly useful as a light emitting material. In addition, the stilbene derivative has excellent resistance to repetition of oxidation reactions.

Embodiment 2

In this embodiment, a synthesis example of a stilbene derivative of the present invention which is different from that in Embodiment 1 is described. Note that the present invention is not limited to the synthesis example given below.

Synthesis Example 2

A synthesis method of (E)-4,4'-bis(9-phenylcarbazol-3-yl)]stilbene (abbr.: PCz$_2$S), which is represented by the structural formula (22), is described. Note that a description on (E)-4-4'-dibromostilbene, which is required for the synthesis of PCz$_2$S, is omitted here because it is given in Embodiment 1.

First, a synthesis method of 9-phenylcarbazol-3-boronic acid is described. 19.6 g (60.7 mmol) of 3-bromo-9-phenylcarbazole was put into a 500 mL three-necked flask, and the air in the flask was replaced with nitrogen. Then, 100 mL of tetrahydrofuran (abbr.: THF) was added thereto. The temperature in the flask was set to be −78° C. and then, 66.8 mL (42.3 mmol) of n-butyllithium hexane solution (1.58 mol/L) was dropped to the solution and was stirred for 3 hours at the same temperature. Then, 13.5 mL (140 mmol) of trimethyl borate was added thereto. The solution was stirred for one hour at the same temperature, then, was stirred for 24 hours while raising the temperature to room temperature. After the reaction, 200 mL of hydrochloric acid (2.0 mol/L) was added to the reaction mixture, and then stirred for one hour at room temperature. After that, the organic layer in the reaction mixture was washed with water and the product was extracted with ethyl acetate from the water which was used for the washing. The obtained extraction solution and the organic layer, which was washed with water, were mixed. The mixture was further washed with a saturated aqueous solution of sodium chloride, and then dried with magnesium sulfate. After the drying, the mixture was suction filtrated, and the filtrate was concentrated. The obtained residue was recrystallized with a mixed solvent of chloroform and hexane to give 10.2 g of a white powdered solid of 9-phenylcarbazol-3-boronic acid (yield: 58%). A synthesis scheme (g-1) of 9-phenylcarbazol-3-boronic acid is shown below.

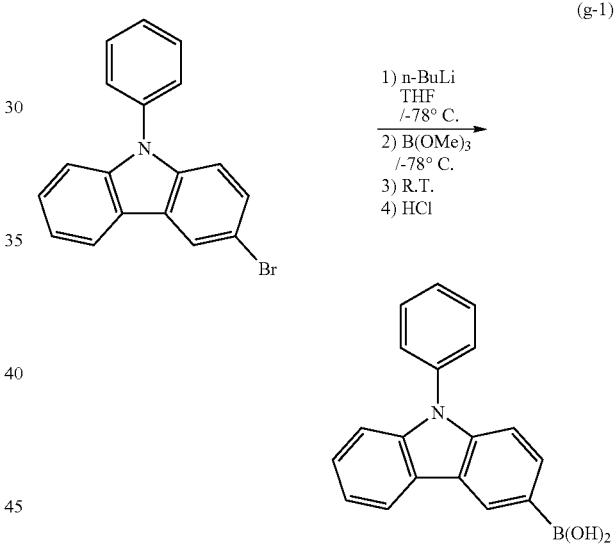

1.0 g (3.0 mmol) of (E)-4,4'-dibromostilbene obtained by the synthesis scheme (f-2) in Embodiment 1, 1.9 g (6.6 mmol) of 9-phenylcarbazol-3-boronic acid, which was obtained as described above, 0.014 g (0.066 mmol) of palladium acetate (II), and 0.14 g (0.45 mmol) of tris(ortho-tolyl)phosphine were put into a 100 mL three-necked flask, and the air in the flask was replaced with nitrogen. Then, 20 mL of ethylene glycol dimethyl ether (DME) and 10 mL (20 mmol) of potassium carbonate solution (2.0 mol/L) were added to the mixture. The mixture was refluxed for 18 hours at 90° C. After the reaction, a precipitate in the reaction mixture was collected by suction filtration. The obtained solid was dissolved in toluene and suction filtrated with florisil, celite, and alumina, and the filtrate was concentrated. The obtained solid was recrystallized with a mixed solvent of chloroform and hexane to give 0.77 g of a light yellow powdered solid (yield: 39%). The light yellow powdered solid was identified as (E)-4,4'-bis(9-phenylcarbazol-3-yl)stilbene (abbr.: PCz$_2$S) by a nuclear magnetic resonance (NMR) method. A synthesis scheme (g-2) of (E)-4,4'-bis(9-phenylcarbazol-3-yl)]stilbene is shown below.

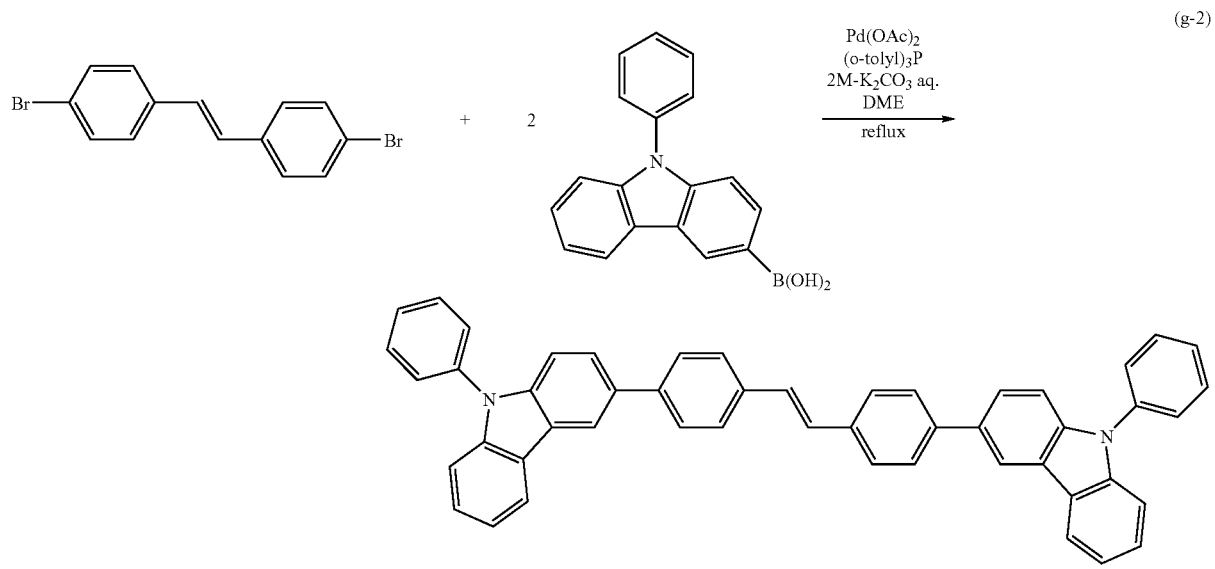

(g-2)

Figure 11A:
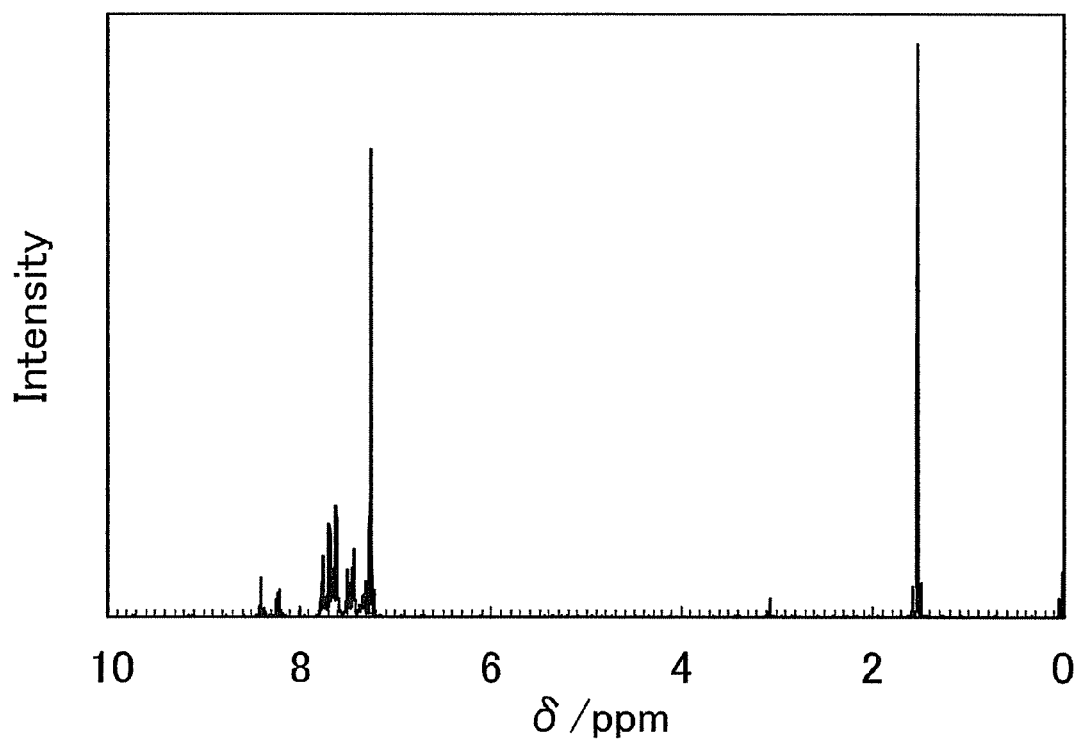
FIGS. 11A and 11B are $^1$H NMR charts of a stilbene derivative (PCz$_2$S) obtained in Synthesis Example 2.
Figure 11B:
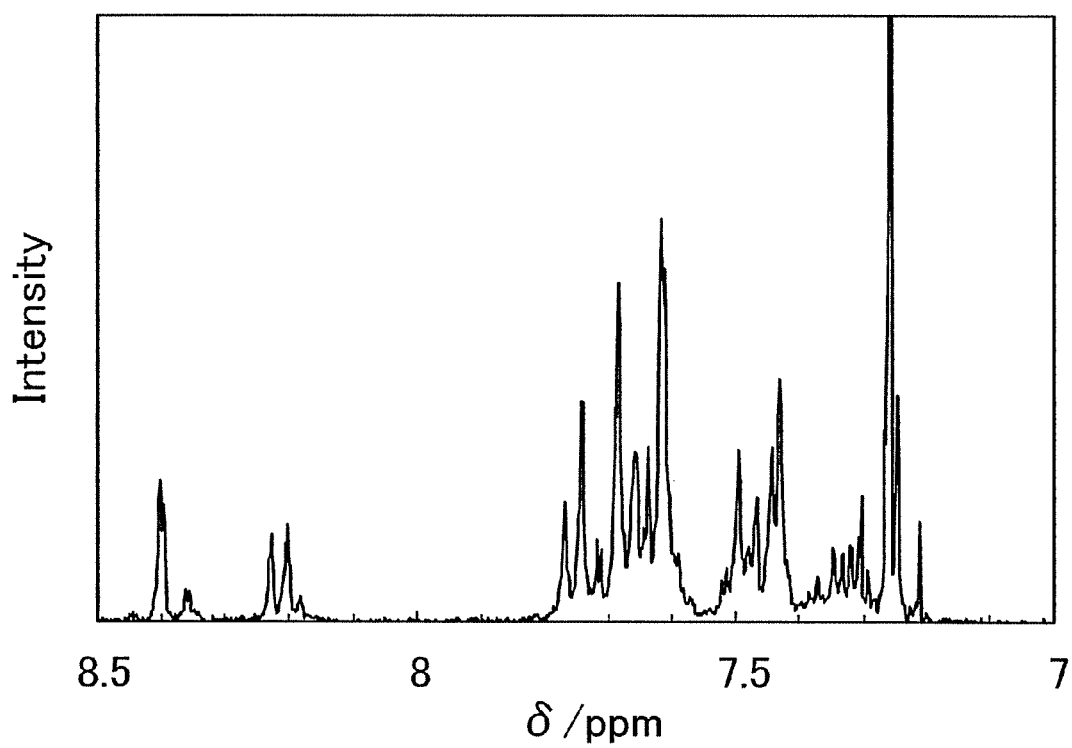

$^1$H NMR of the compound is shown below. A $^1$H NMR chart is shown in each of FIGS. 11A and 11B. The range of 7.0 ppm to 8.5 ppm in FIG. 11A is expanded and shown in FIG. 11B.

$^1$H NMR (CDCl$_3$, 300 MHz): δ=7.25-7.35 (m, 4H), 7.43-7.49 (m, 8H), 7.61-7.77 (m, 18H), 8.20-8.40 (m, 4H).

0.77 g of the obtained (E)-4,4'-bis(9-phenylcarbazol-3-yl)stilbene (abbr.: PCz$_2$S) was heated to 380° C. and was purified by sublimation under a condition where a pressure was 7.8 Pa and an argon flow rate was 3.0 mL/min, so that 0.32 g was recovered and the recovery rate was 42%.

Figure 12:
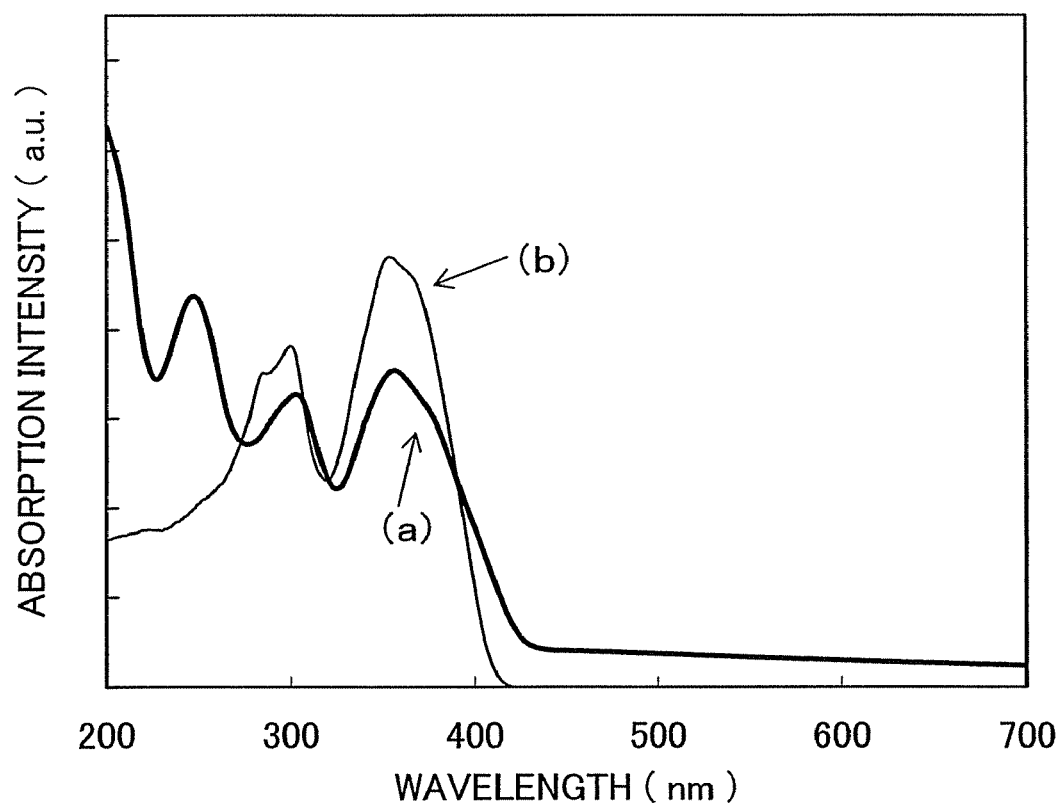
FIG. 12 is a graph showing an absorption spectrum of PCz$_2$S.

An absorption spectrum of PCz$_2$S is shown in FIG. 12. The ultraviolet-visible spectrophotometer (manufactured by JASCO Corporation, V-550) was used for the measurement. In FIG. 12, the horizontal axis indicates a wavelength (nm) and the vertical axis indicates absorption intensity (arbitrary unit). Note that, in FIG. 12, (a) indicates the absorption spectrum in a state where PCz$_2$S is a thin film, whereas (b) indicates the absorption spectrum in a state where PCz$_2$S is dissolved in a toluene solution. Note that each of the samples was formed by putting the solution in a quartz cell or by forming the film on a quartz substrate by evaporation. Absorption spectra of the samples, from each of which an absorption spectrum of quartz was subtracted, are shown. An energy gap of PCz$_2$S was found to be 3.05 eV, using a tauc plot, according to the absorption spectrum in the thin film state ((a) in FIG. 12).

Figure 13:
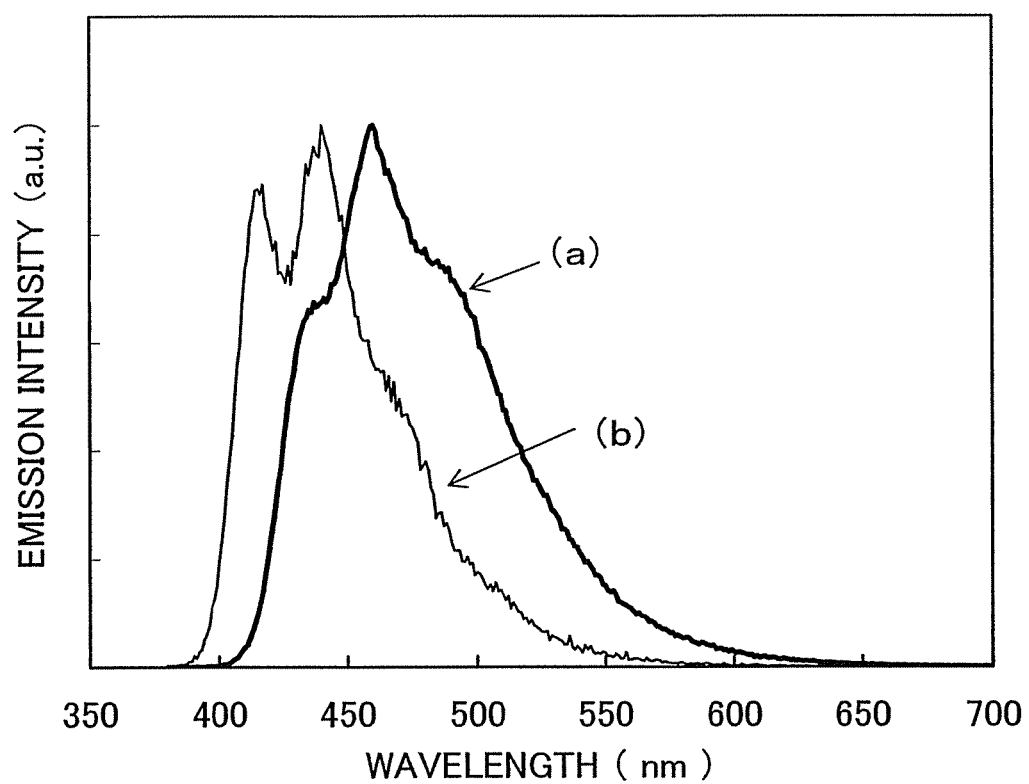
FIG. 13 is a graph showing an emission spectrum of PCz$_2$S.

An emission spectrum of PCz$_2$S is shown in FIG. 13. In FIG. 13, the horizontal axis indicates a wavelength (nm) and the vertical axis indicates emission intensity (arbitrary unit). In FIG. 13, (a) indicates the emission spectrum in a state where PCz$_2$S is a thin film (excitation wavelength: 357 nm), whereas (b) indicates the emission spectrum in a state where PCz$_2$S is dissolved in a toluene solution (excitation wavelength: 377 nm). It is found according to FIG. 13 that light emission from PCz$_2$S has a peak at 460 nm in the thin film state and has peaks at 417 nm and 440 nm in the toluene solution. These light emission was recognized as blue light emission.

A film of the obtained PCz$_2$S was formed by an evaporation method. An ionization potential of the compound in the thin film state was measured with a photoelectron spectrometer (manufactured by Riken Keiki Co., Ltd., AC-2) and was found to be 5.55 eV. Accordingly, the HOMO level was found to be −5.55 eV. In addition, the LUMO level, which was obtained by using the energy gap (3.05 eV), was found to be −2.50 eV.

Thermogravimetry-Differential Thermal Analysis (TG-DTA) of the obtained PCz$_2$S was carried out. The measurement was conducted using a thermo-gravimetric/differential thermal analyzer (manufactured by Seiko Instruments Inc., TG/DTA-320). The temperature at which the weight was reduced to be less than or equal to 95% of the weight at the beginning of the measurement was 484.5° C. Accordingly, it is found that PCz$_2$S has excellent heat resistance.

An oxidation reaction property of PCz$_2$S was measured by a cyclic voltammetry (CV) measurement. Note that an electrochemical analyzer (manufactured by BAS Inc., ALS model 600A) was used for the measurement.

The solution for the CV measurement was prepared by dissolving supporting electrolyte of tetra-n-butylammonium perchlorate (n-Bu$_4$NClO$_4$) in a solvent of dehydrated dimethylformamide (DMF) so as to make a solution with a concentration of 100 mmol/L, and by further dissolving PCz$_2$S, the material to be measured, to a concentration of 1 mmol/L. A platinum electrode (manufactured by BAS Inc., PTE platinum electrode) was used as an indicator electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-5 Reference electrode for nonaqueous solvent) was used as a reference electrode.

The oxidation reaction property was measured as follows. The electric potential of the indicator electrode with respect to the reference electrode was changed from −0.25 to 0.90 V, and then, from 0.90 to −0.25 V. A scan for the change was set as 1 cycle, and 100 cycles were measured. The CV measurement was carried out with a scan speed of 0.10 V/s.

Figure 14:
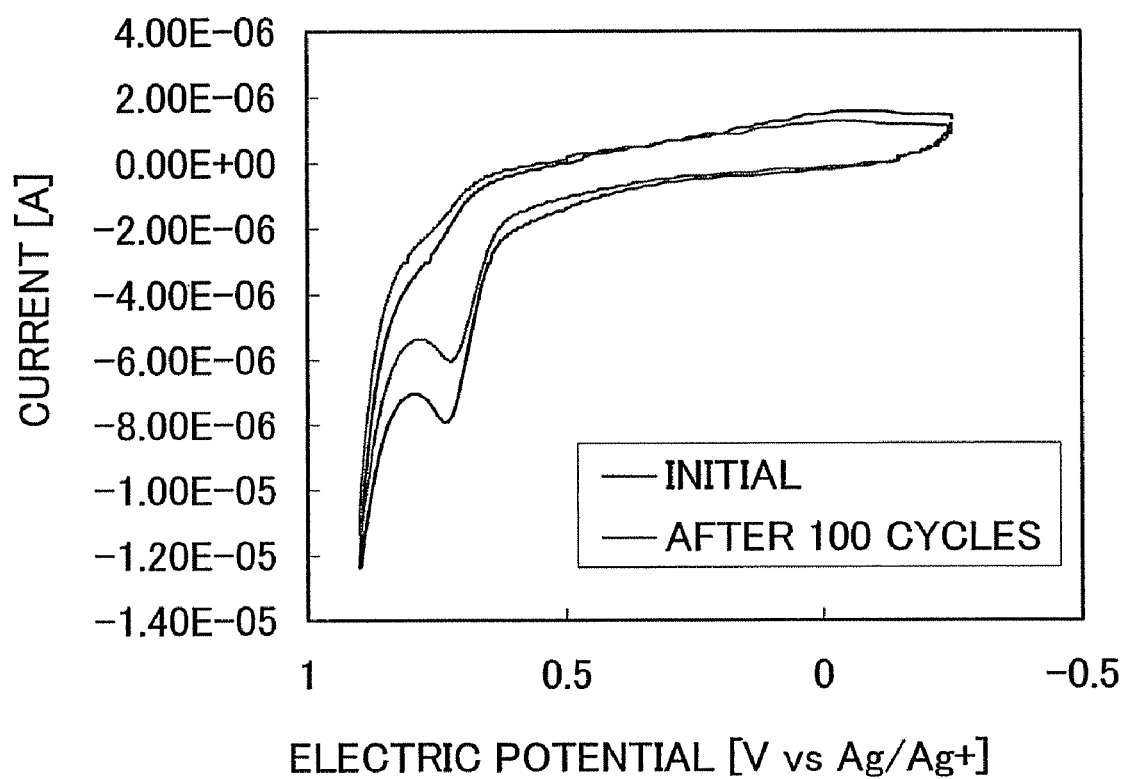
FIG. 14 is a graph showing a measurement result of cyclic voltammetry (CV) on PCz$_2$S.

FIG. 14 shows the result of the measurement of the oxidation reaction property of PCz$_2$S. In FIG. 14, the horizontal axis indicates electric potential (V) of the indicator electrode with respect to the reference electrode and the vertical axis indicates a current value (A) flowing between the reference electrode and the auxiliary electrode.

FIG. 14 shows that an oxidation peak electric potential is approximately 0.73 V (vs. Ag/Ag$^+$ electrode). In addition, although the scan was repeated for 100 cycles, the peak position and the peak intensity of the CV curve hardly changed. Therefore, it is found that a stilbene derivative of the present invention is quite stable with respect to oxidation reaction.

As described above, the stilbene derivative of the present invention can exhibit blue light emission with excellent color purity. Accordingly, the stilbene derivative is highly useful as a light emitting material. In addition, the stilbene derivative has excellent resistance to repetition of oxidation reactions.

Embodiment 3

In this embodiment, a synthesis example of a stilbene derivative of the present invention which is different from those in Embodiments 1 and 2 is described. Note that the present invention is not limited to the synthesis example given below.

Synthesis Example 3

A synthesis method of (E)-4-(9-phenylcarbazol-3-yl)stilbene (abbr.: PCzS), which is represented by the structural formula (12), is described. Note that a description on (4-bromobenzyl)triphenylphosphoniumbromide, which is required for the synthesis of PCzS, is omitted here because it is given in Embodiment 1.

First, a synthesis method of 4-bromostilbene is described. 25.3 g (49.5 mmol) of (4-bromobenzyl)triphenylphosphoniumbromide and 5.25 g (49.5 mmol) of benzaldehyde were put into a 500 mL three-necked flask and the air in the flask was replaced with nitrogen. 250 mL of tetrahydrofuran (THF) was added to the mixture. Then, a suspension in which 6.10 g (54.4 mmol) of potassium tert-butoxide was dissolved in 60 mL of THF was dropped to this mixture. After the dropping, the reaction mixture was stirred for 24 hours at room temperature. After the reaction, the reaction mixture was washed with water and the product was extracted with ethyl acetate from the water which was used for the washing. The obtained extraction solution and the organic layer, which was washed with water, were mixed and dried with magnesium sulfate. After the drying, the mixture was suction filtrated, and the filtrate was concentrated. The obtained residue was purified by silica gel column chromatography (developing solution: toluene). The obtained compound was washed with methanol and the solid was collected by suction filtration to give 3.75 g or a white powdered solid of (E)-4-bromostilbene (yield: 29.2%). A synthesis scheme (h-1) of 4-bromostilbene is shown below. Note that (Z)-4-bromostilbene was also observed in this reaction, but only (E)-4-bromostilbene was isolated and purified.

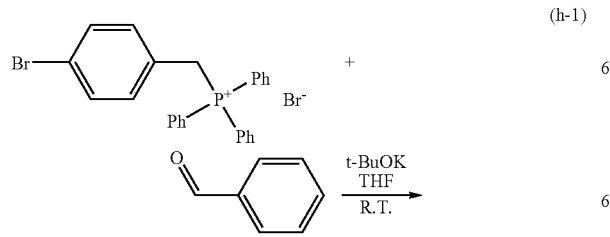

(h-1)

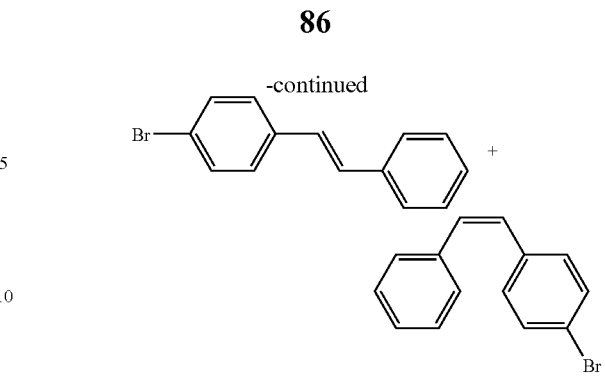

-continued 1.0 g (3.9 mmol) of (E)-4-bromostilbene, which was obtained as described above, 1.2 g (4.2 mmol) of 9-phenylcarbazol-3-boronic acid, which was obtained in the synthesis scheme (g-1) in Embodiment 2, 0.0087 g (0.039 mmol) of palladium acetate (II), and 0.081 g (0.27 mmol) of tris(ortho-tolyl)phosphine were put into a 100 mL three-necked flask, and the air in the flask was replaced with nitrogen. Then, 20 mL of ethylene glycol dimethyl ether (DME) and 6 mL (12 mmol) of potassium carbonate solution (2.0 mol/L) were added to the mixture. The mixture was refluxed for 14 hours at 80° C. After the reaction, a precipitate in the reaction mixture was collected by suction filtration. The collected solid was purified by silica gel column chromatography (developing solution: toluene). The obtained solution was concentrated. The obtained compound was recrystallized with a mixed solvent of chloroform and hexane to give 0.46 g of a light yellow powdered solid (yield: 28%). Note that the light yellow powdered solid was identified as (E)-4-(9-phenylcarbazol-3-yl)stilbene (abbr.: PCzS) by a nuclear magnetic resonance (NMR) method. A synthesis scheme (h-2) of (E)-4-(9-phenylcarbazol-3-yl)stilbene is shown below.

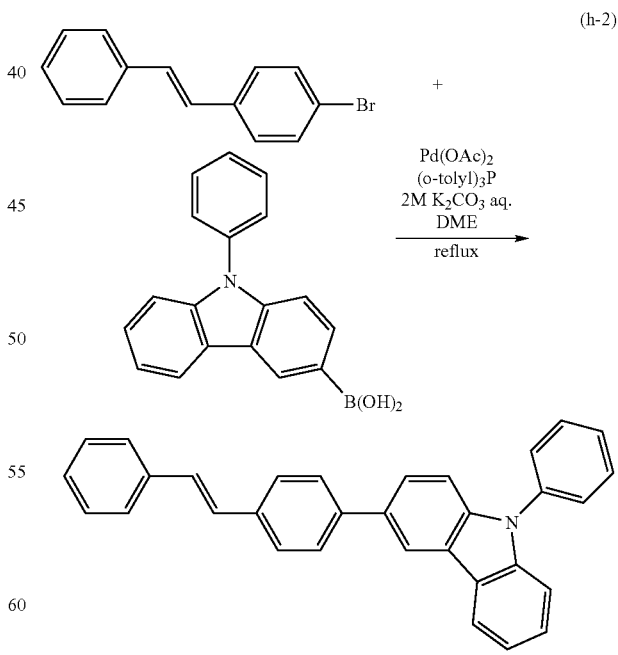

(h-2)

Figure 15A:
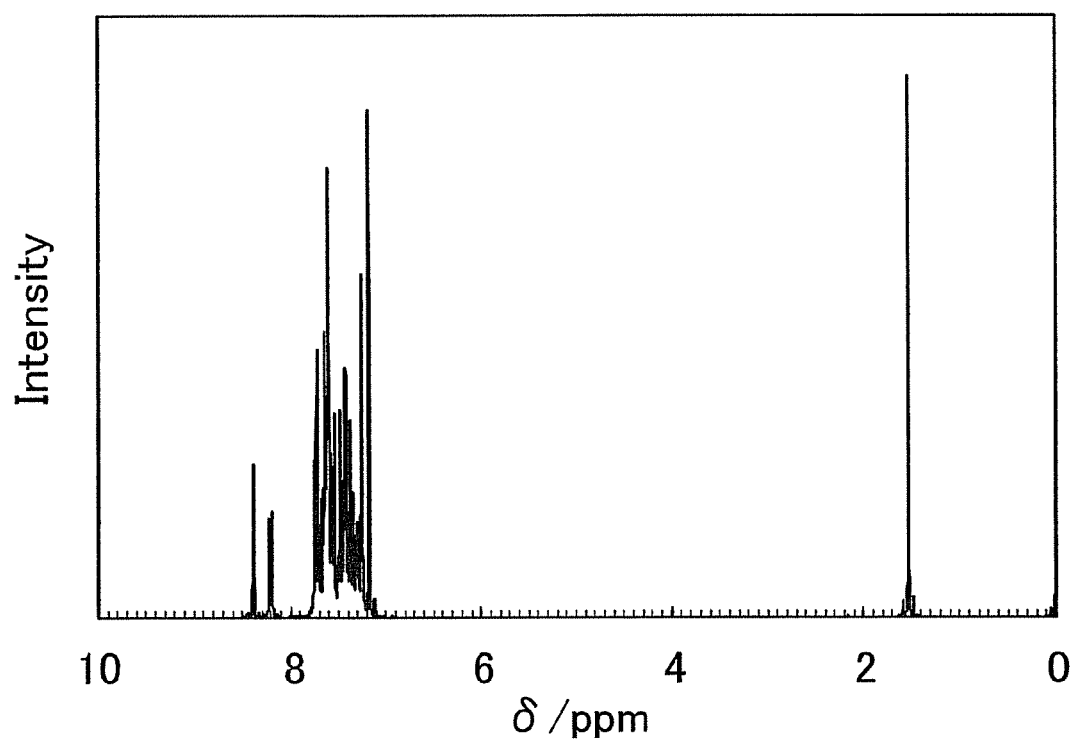
FIGS. 15A and 15B are $^1$H NMR charts of a stilbene derivative (PCzS) obtained in Synthesis Example 3.
Figure 15B:
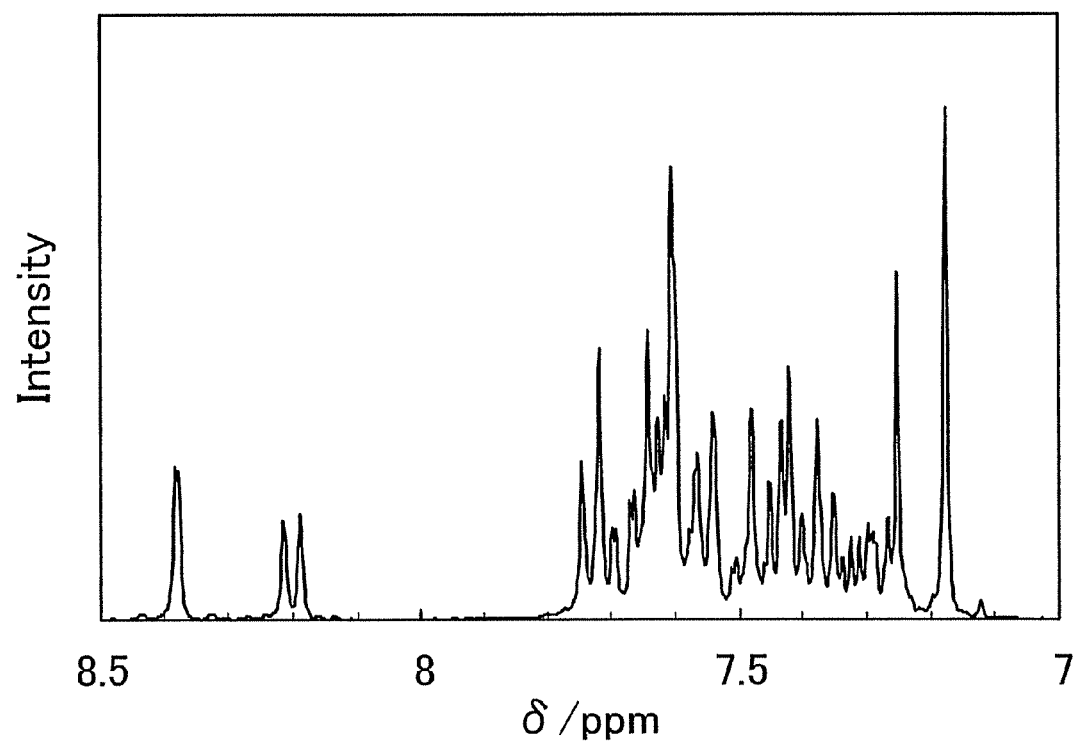

Then, $^1$H NMR of the compound is shown below. A $^1$H NMR chart is shown in each of FIGS. 15A and 15B. The range of 7.0 ppm to 8.5 ppm in FIG. 15A is expanded and shown in FIG. 15B.

¹H NMR (CDCl$_3$, 300 MHz): δ=7.25-7.75 (m, 21H), 8.20 (d, J=7.8 Hz, 1H), 8.38 (s, 1H).

0.46 g of the obtained (E)-4-(9-phenylcarbazol-3-yl)stilbene (abbr.: PCzS) was heated to 230° C. and was purified by sublimation under a condition where a pressure of 7.8 Pa and an argon flow rate was 3.0 mL/min, so that, 0.35 g was recovered and the recovery rate was 76%.

Figure 16:
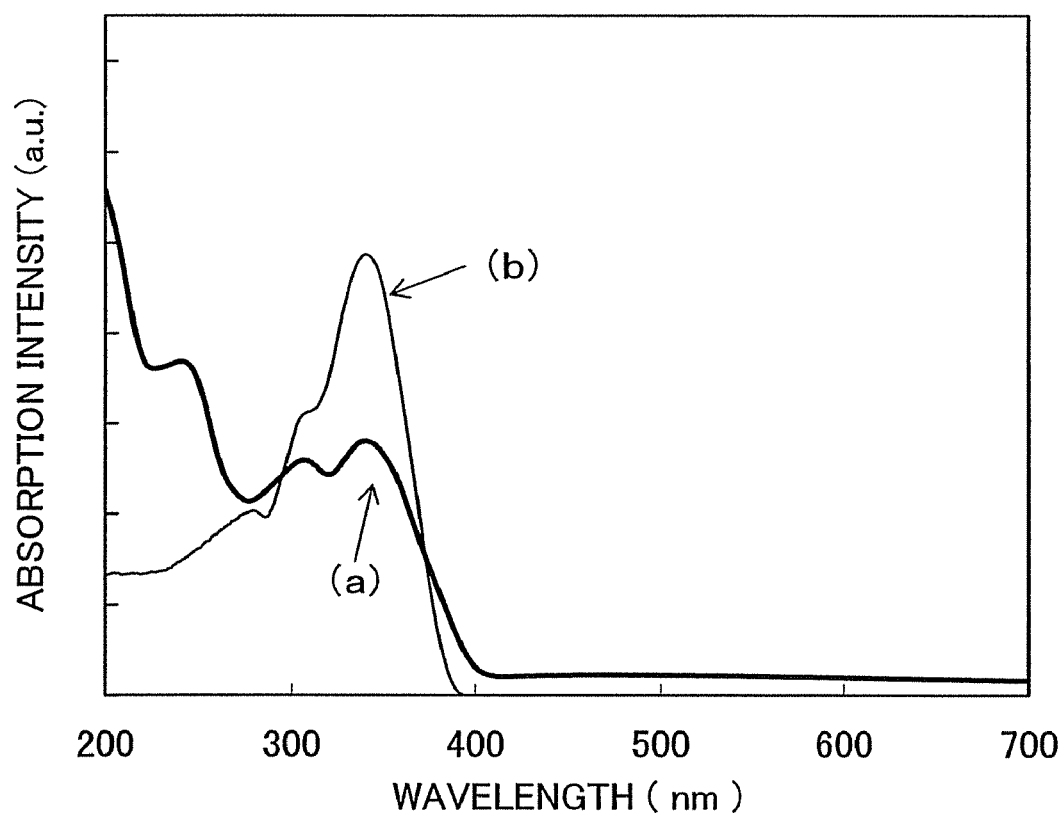
FIG. 16 is a graph showing an absorption spectrum of PCzS.

An absorption spectrum of PCzS is shown in FIG. 16. The ultraviolet-visible spectrophotometer (manufactured by JASCO Corporation, V-550) was used for the measurement. In FIG. 16, the horizontal axis indicates a wavelength (nm) and the vertical axis indicates absorption intensity (arbitrary unit). Note that, in FIG. 16, (a) indicates the absorption spectrum in a state where PCzS is a thin film, whereas (b) indicates the absorption spectrum in a state where PCzS is dissolved in a toluene solution. Note that each of the samples was formed by putting the solution in a quartz cell or by forming the film on a quartz substrate by evaporation. Absorption spectra of the samples, from each of which an absorption spectrum of quartz was subtracted, are shown. An energy gap of PCzS was found to be 3.26 eV, using a tauc plot, according to the absorption spectrum in the thin film state ((a) in FIG. 16).

Figure 17:
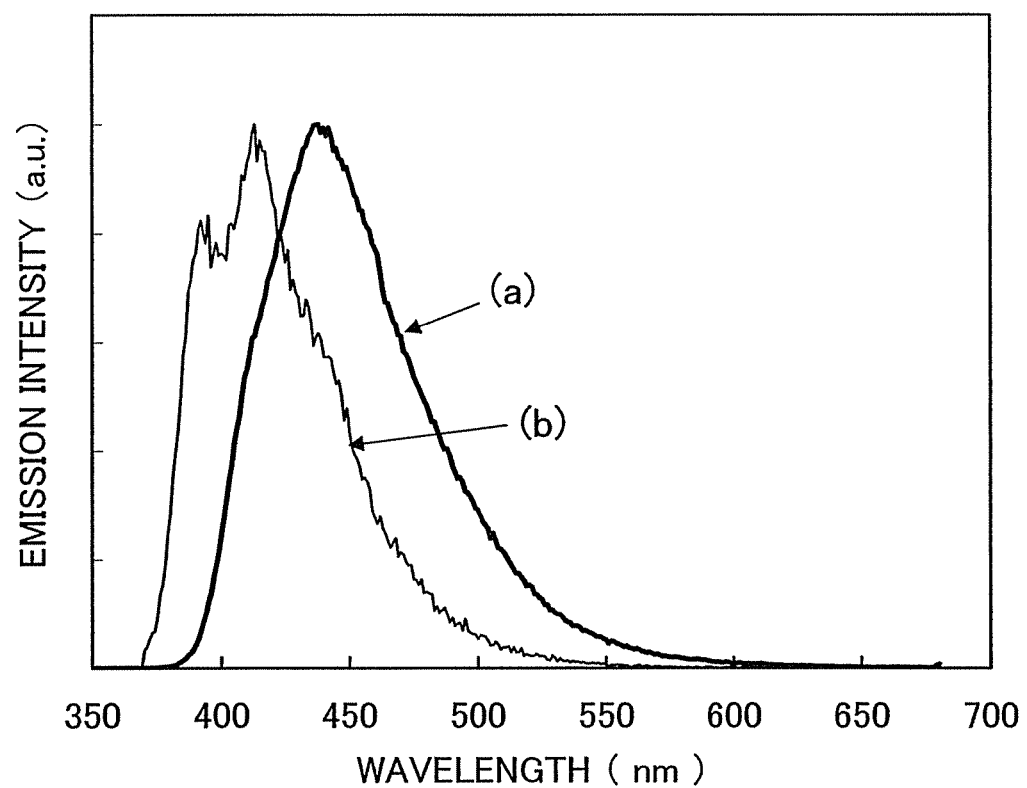
FIG. 17 is a graph showing an emission spectrum of PCzS.

An Emission spectrum of PCzS is shown in FIG. 17. In FIG. 17, the horizontal axis indicates a wavelength (nm) and the vertical axis indicates emission intensity (arbitrary unit). In FIG. 17, (a) indicates the emission spectrum in a state where PCzS is a thin film (excitation wavelength: 341 nm), whereas (b) indicates the emission spectrum in a state where PCzS is dissolved in a toluene solution (excitation wavelength: 357 nm). According to FIG. 17, it is found that light emission from PCzS has a peak at 438 nm in the thin film state and has peaks at 392 nm and 413 nm in the toluene solution. These light emission was recognized as blue light emission.

A film of the obtained PCzS was formed by an evaporation method. An ionization potential of the compound in the thin film state was measured with a photoelectron spectrometer (manufactured by Riken Keiki Co., Ltd., AC-2) and was found to be 5.63 eV Accordingly, the HOMO level was found to be −5.63 eV. In addition, the LUMO level, which was obtained by using the energy gap (3.26 eV), was found to be −2.37 eV.

Thermogravimetry-Differential Thermal Analysis (TG-DTA) of the obtained PCzS was carried out. The measurement was conducted using a thermo-gravimetric/differential thermal analyzer (manufactured by Seiko Instruments Inc., TG/DTA-320). The temperature at which the weight was reduced to be less than or equal to 95% of the weight at the beginning of the measurement was 319.7° C. Accordingly, it is found that PCzS has excellent heat resistance.

An oxidation reaction property of PCzS was measured by a cyclic voltammetry (CV) measurement. Note that an electrochemical analyzer (manufactured by BAS Inc., ALS model 600A) was used for the measurement.

The solution for the CV measurement was prepared by dissolving supporting electrolyte of tetra-n-butylammonium perchlorate (n-Bu$_4$NClO$_4$) in a solvent of dehydrated dimethylformamide (DMF) so as to make a solution with a concentration of 100 mmol/L, and by further dissolving PCzS, the material to be measured, to a concentration of 1 mmol/L. A platinum electrode (manufactured by BAS Inc., PTE platinum electrode) was used as an indicator electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-5 Reference electrode for nonaqueous solvent) was used as a reference electrode.

The oxidation reaction property was measured as follows. The electric potential of the indicator electrode with respect to the reference electrode was changed from −0.25 to 1.00 V, and then, from 1.00 to −0.25 V. A scan for the change was set as 1 cycle, and 100 cycles were measured. The CV measurement was carried out with a scan speed of 0.10 V/s.

Figure 18:
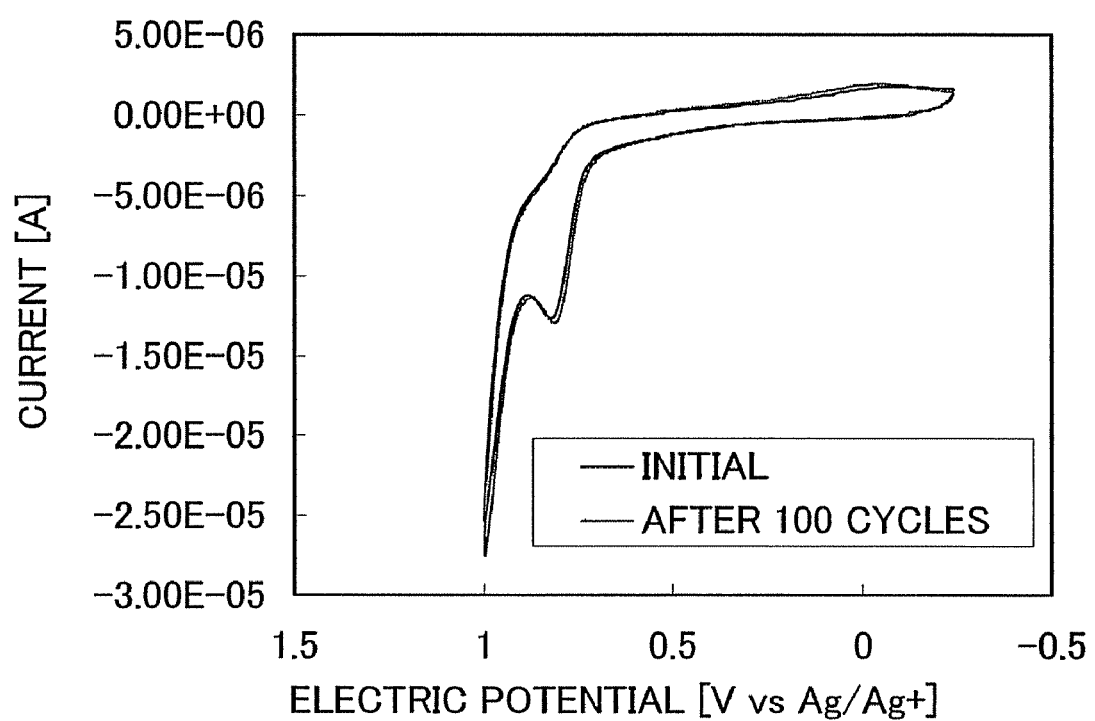
FIG. 18 is a graph showing a measurement result of cyclic voltammetry (CV) on PCzS.

FIG. 18 shows the result of the measurement of the oxidation reaction property of PCzS. In FIG. 18, the horizontal axis indicates electric potential (V) of the indicator electrode with respect to the reference electrode and the vertical axis indicates current (A) flowing between the reference electrode and the auxiliary electrode.

FIG. 18 shows that an oxidation peak electric potential is approximately 0.81 V (vs. Ag/Ag$^+$ electrode). In addition, although the scan was repeated for 100 cycles, the peak position and the peak intensity of the CV curve hardly changed. Therefore, it is found that a stilbene derivative of the present invention is quite stable with respect to oxidation reaction.

As described above, the stilbene derivative of the present invention can exhibit blue light emission with excellent color purity. Accordingly, the stilbene derivative is highly useful as a light emitting material. In addition, the stilbene derivative has excellent resistance to repetition of oxidation reactions.

Embodiment 4

In this embodiment, a synthesis example of a stilbene derivative of the present invention which is different from those in Embodiments 1 to 3 is described. Note that the present invention is not limited to the synthesis example given below.

Synthesis Example 4

A synthesis method of (E)-4-(carbazol-9-yl)stilbene (abbr.: CzPS), which is represented by the structural formula (3), is described. Note that a description on 4-(carbazol-9-yl)phenylboronic acid and (E)-4-bromostilbene which are required for the synthesis of CzPS, is omitted here because it is given in Embodiment 1 and Embodiment 3, respectively.

1.0 g (3.9 mmol) of (E)-4-dibromostilbene, which was obtained in the synthesis scheme (h-1) in Embodiment 3, 1.1 g (3.9 mmol) of 4-(carbazol-9-yl)phenylboronic acid, which was obtained in the synthesis scheme (f-3), in Embodiment 1, and 0.294 g (0.97 mmol) of tris(ortho-tolyl)phosphine were put into a 100 mL three-necked flask, and the air in the flask was replaced with nitrogen. Then, 20 mL of toluene, 10 mL of ethanol, and 7 mL (14 mmol) of potassium carbonate solution (2.0 mol/L) were added thereto. The mixture was degassed while being stirred under reduced pressure in the flask. Then, 0.043 g (0.19 mmol) of palladium acetate (II) was added thereto. The mixture was refluxed for 4 hours. After the reaction, a precipitate in the reaction mixture was collected by suction filtration. The collected solid was dissolved in toluene and suction filtrated with florisil, celite, and alumina. The filtrate was concentrated to obtain a solid. The obtained solid was recrystallized with a mixed solvent of toluene and hexane to give 0.96 g of white needle-like crystals (yield: 59%). The white needle-like crystal was identified as (E)-4-(carbazol-9-yl)stilbene (abbr.: CzPS) by a nuclear magnetic resonance (NMR) method. A synthesis scheme (i-1) of (E)-4-(carbazol-9-yl)stilbene is shown below.

(i-1)

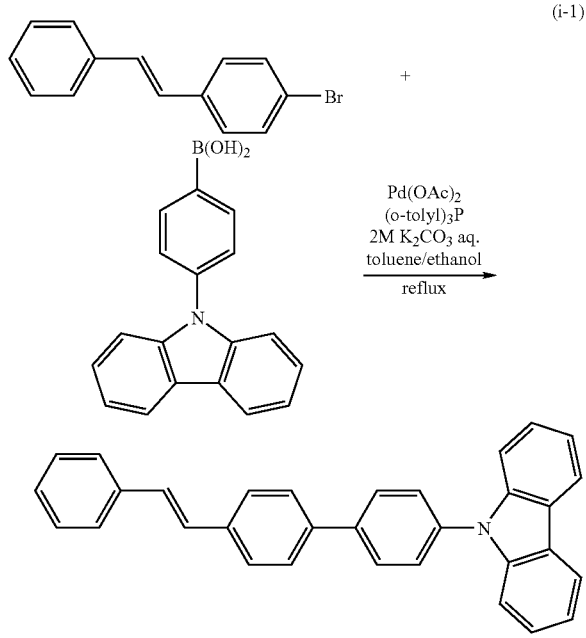

Figure 28A:
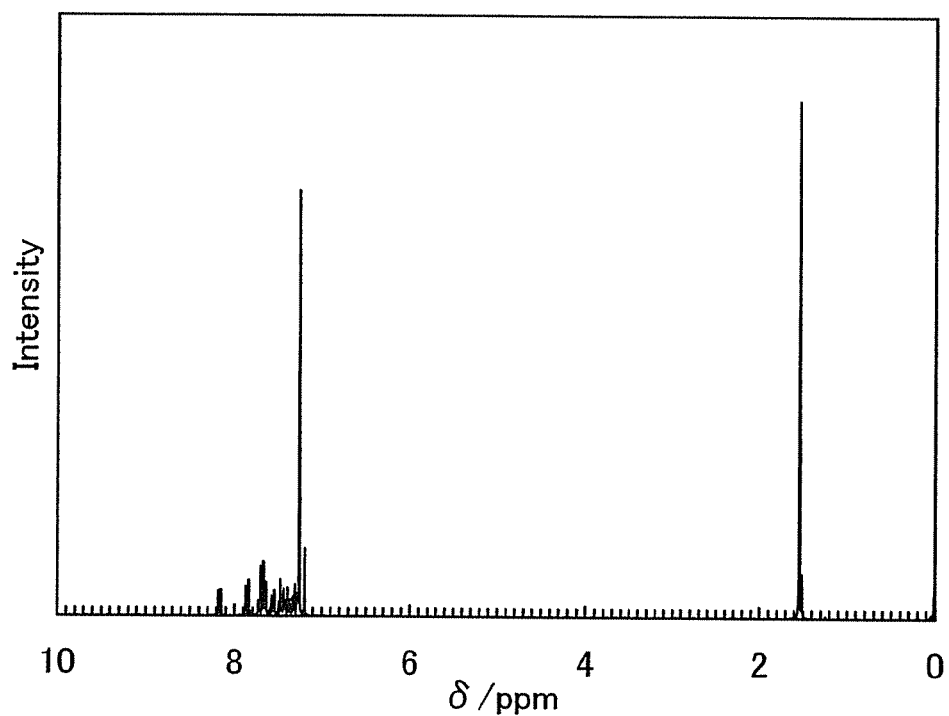
FIGS. 28A and 28B are $^1$H NMR charts of a stilbene derivative (CzPS) obtained in Synthesis Example 4.
Figure 28B:
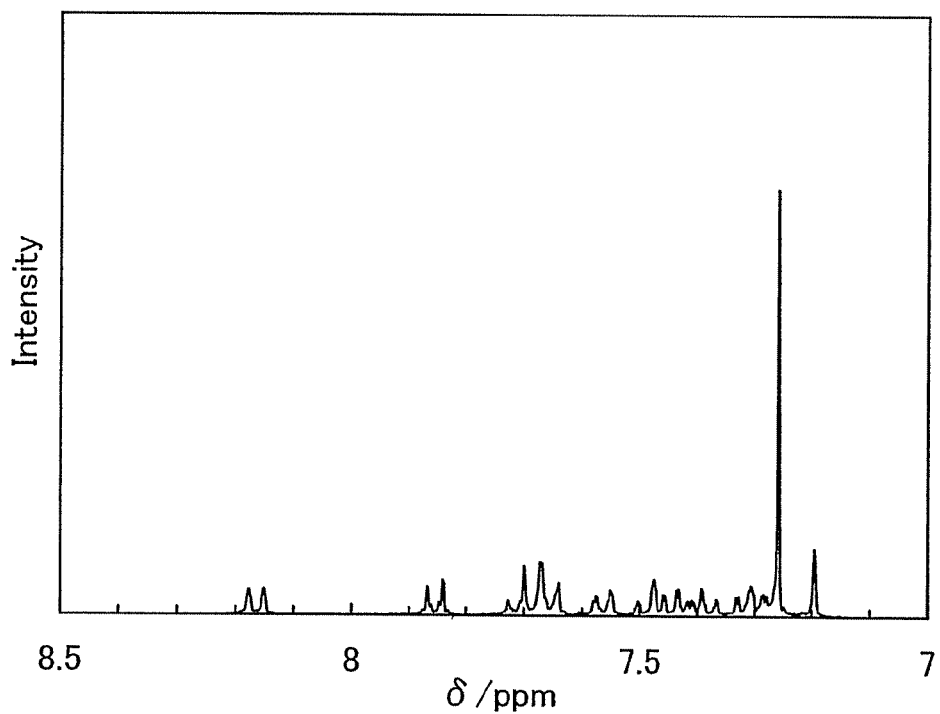

Then, ¹H NMR of the compound is shown below. A ¹H NMR chart is shown in each of FIGS. 28A and 28B. The range of 7.0 ppm to 8.5 ppm in FIG. 28A is expanded and shown in FIG. 28B.

¹H NMR (CDCl$_3$, 300 MHz): δ=7.20 (s, 2H), 7.30 (t-d, J1=8.1 Hz, J2=1.2 Hz, 3H), 7.38 (d, J=7.8 Hz, 1H), 7.41-7.42 (m, 1H), 7.45 (d-d, J1=6.9 Hz, J2=0.9 Hz, 2H), 7.49 (d, J=8.4H z, 2H), 7.56 (d, J=7.2 Hz, 2H), 7.64-7.73 (m, 6H), 7.86 (d, J=8.4 Hz, 2H), 8.16 (d, J=7.8 Hz, 2H).

Figure 29:
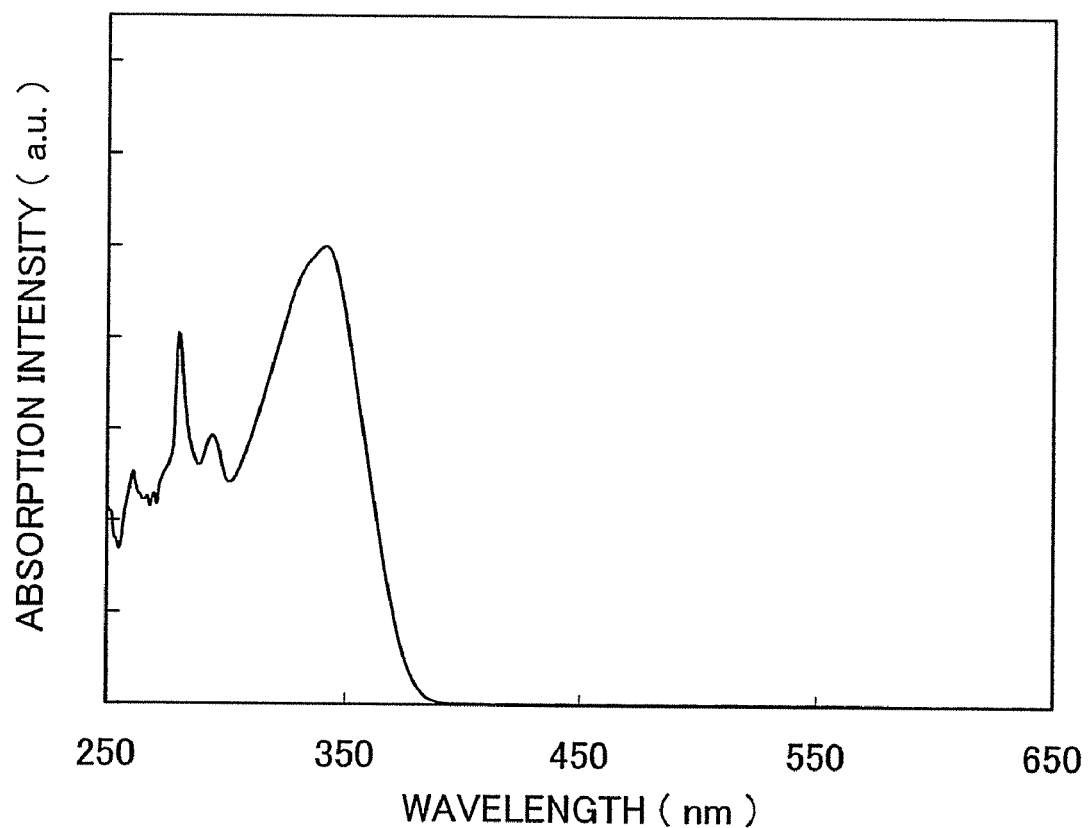
FIG. 29 is a graph showing an absorption spectrum of CzPS.

An absorption spectrum of CzPS is shown in FIG. 29. In FIG. 29, the horizontal axis indicates a wavelength (nm) and the vertical axis indicates absorption intensity (arbitrary unit (a.u.)). The ultraviolet-visible spectrophotometer (manufactured by JASCO Corporation, V-550) was used for the measurement. The absorption spectrum shown in FIG. 29 is the absorption spectrum in a state where CzPS is dissolved in a toluene solution. According to FIG. 29, CzPS has absorption peaks at 292 nm and 341 nm.

Figure 30:
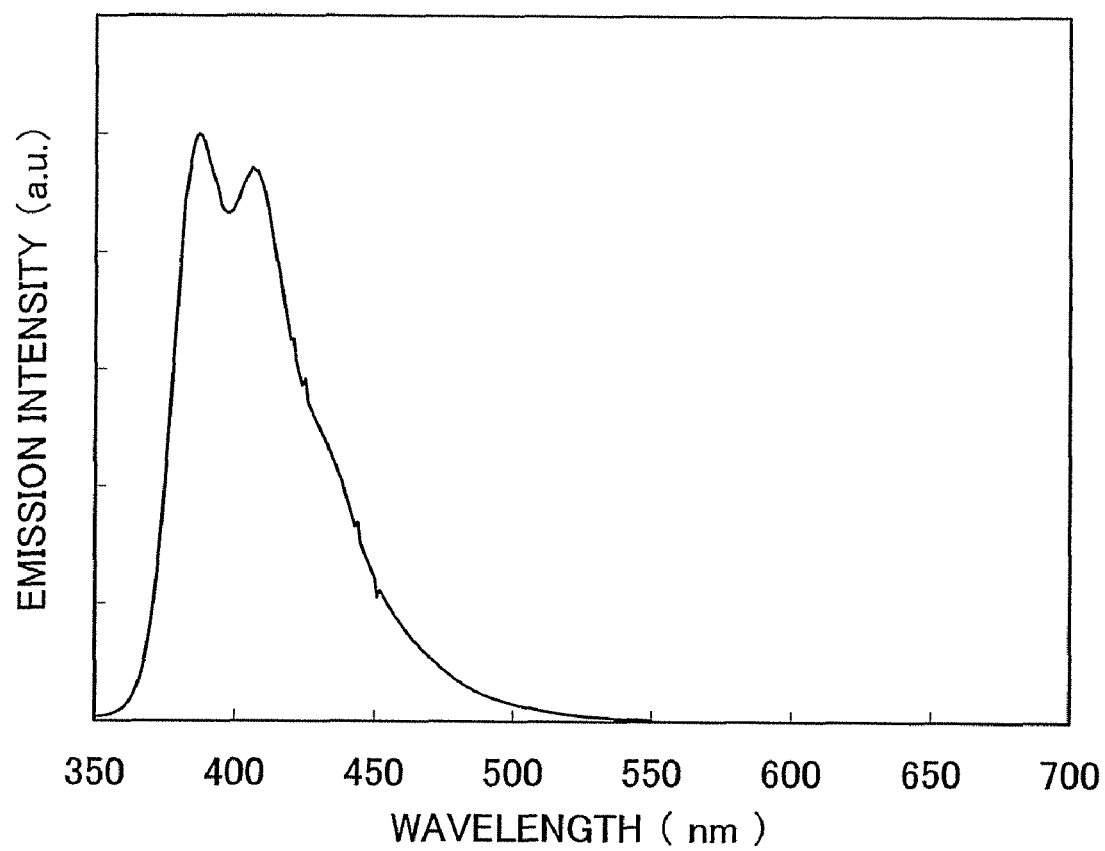
FIG. 30 is a graph showing an emission spectrum of CzPS.

An emission spectrum of CzPS is shown in FIG. 30. In FIG. 30, the horizontal axis indicates a wavelength (nm) and the vertical axis indicates emission intensity (arbitrary unit). The emission spectrum shown in FIG. 30 is the emission spectrum in the state where CzPS is dissolved in a toluene solution (excitation wavelength: 340 nm). According to FIG. 30, light emission from CzPS in a toluene solution has peaks at 387 nm and 408 nm. These light emission was recognized as blue light emission.

Thermogravimetry-Differential Thermal Analysis (TG-DTA) of the obtained CzPS was carried out. The measurement was conducted using a thermo-gravimetric/differential thermal analyzer (manufactured by Seiko Instruments Inc., TG/DTA-320). The temperature at which the weight was reduced to be less than or equal to 95% of the weight at the beginning of the measurement was 374° C.

As described above, the stilbene derivative of the present invention can exhibit blue light emission with excellent color purity. Accordingly, the stilbene derivative is highly useful as a light emitting material.

Embodiment 5

Figure 19:
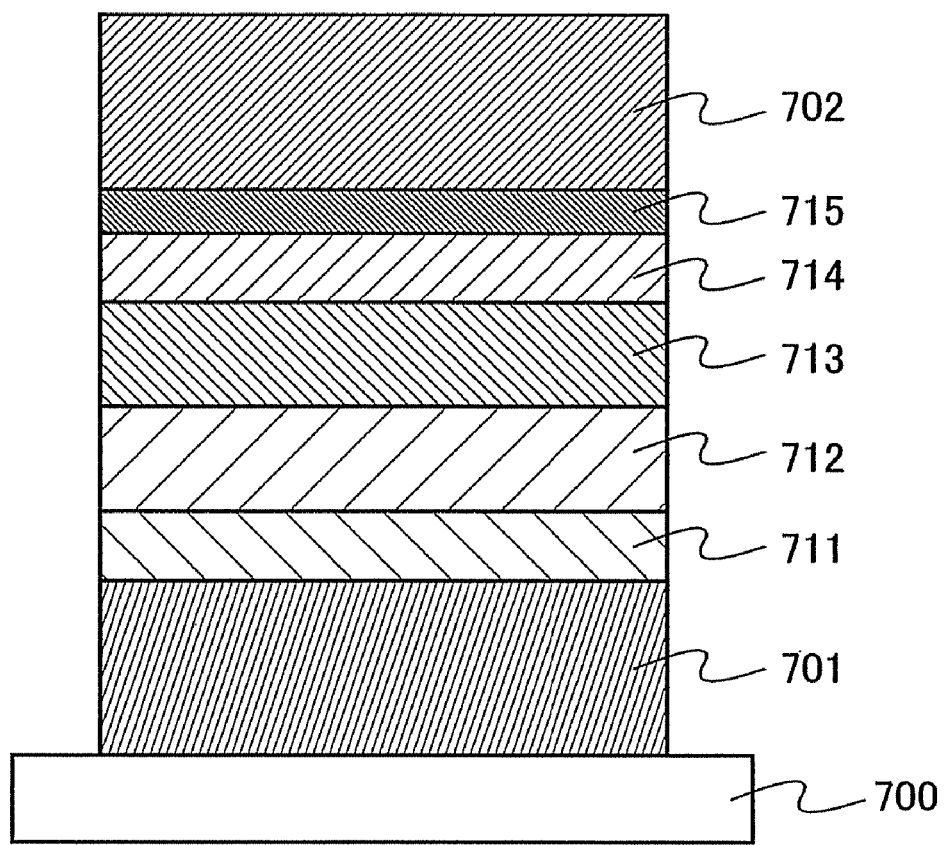
FIG. 19 shows an element structure of a light emitting element formed in Embodiments.

In this embodiment, a manufacturing method of a light emitting element in which (E)-4,4'-bis[4-(carbazol-9-yl)phenyl]stilbene (abbr.: CzP$_2$S), which is synthesized in Synthesis Example 1, is used in a light emitting layer, and operation characteristics of the light emitting element are described with reference to FIG. 19.

First, indium tin oxide containing silicon oxide (abbr.: ITSO) was deposited over a glass substrate 700 by a sputtering method to be a first electrode 701.

Then, the glass substrate 700, over which the first electrode 701 was formed, was fixed to a substrate holder in a vacuum evaporation apparatus in a manner such that the surface on which the first electrode 701 was formed faced downward. Then, a hole injecting layer 711 was formed by depositing NPB and molybdenum trioxide by co-evaporation to have a thickness of 50 nm on the first electrode 701. Note that a mass ratio of NPB to molybdenum trioxide was set to be 4:1 (=NPB:molybdenum trioxide).

Then, a hole transporting layer 712 was formed by depositing NPB on the hole injecting layer 711 by an evaporation method to have a thickness of 10 nm.

Then, a light emitting layer 713 was formed by depositing CBP and CzP$_2$S by co-evaporation on the hole transporting layer 712 to have a thickness of 30 nm. Note that a mass ratio of CBP to CZP$_2$S was set to be 1:0.05 (=CBP:CzP$_2$S). Thus, CzP$_2$S was in a state of being dispersed in a layer formed of CBP.

An electron transporting layer 714 was formed by depositing BCP on the light emitting layer 713 to have a thickness of 10 nm. Note that an evaporation method was employed for the film formation.

An electron injecting layer 715 was formed by depositing Alq$_3$ and Li by co-evaporation on the electron transporting layer 714 to have a thickness of 20 nm. Note that a mass ratio of Alq$_3$ to Li was set to be 1:0.01 (=Alq$_3$:Li).

A second electrode 702 was formed by depositing aluminum by an evaporation method on the electron injecting layer 715.

In the foregoing manner, the light emitting element was formed by stacking the hole injecting layer 711, the hole transporting layer 712, the light emitting layer 713, the electron transporting layer 714, and the electron injecting layer 715, between the first electrode 701 and the second electrode 702. Note that NPB, CBP, BCP, and Alq$_3$, which were used for the layers, are shown below as the structural formulae (107), (108), (109), and (110), respectively.

(107)

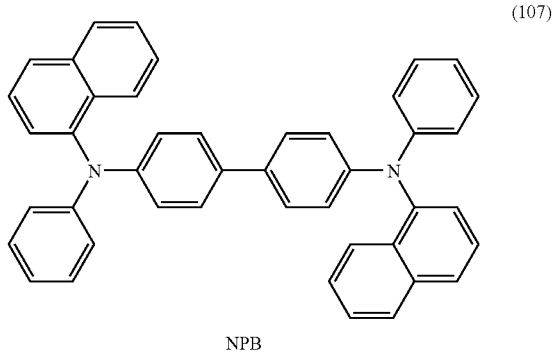

NPB

-continued

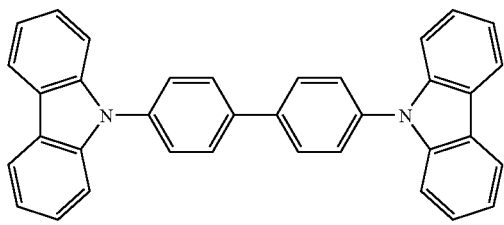

CBP (108)

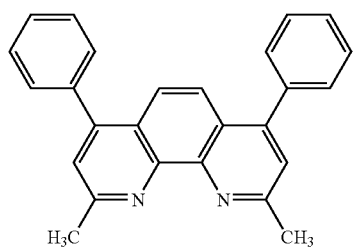

BCP (109)

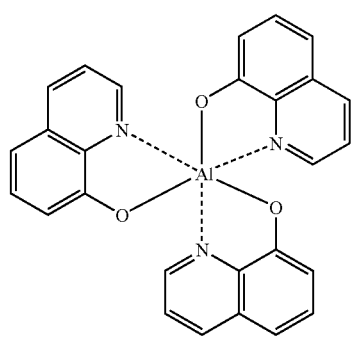

Alq₃ (110)

Figure 20A:
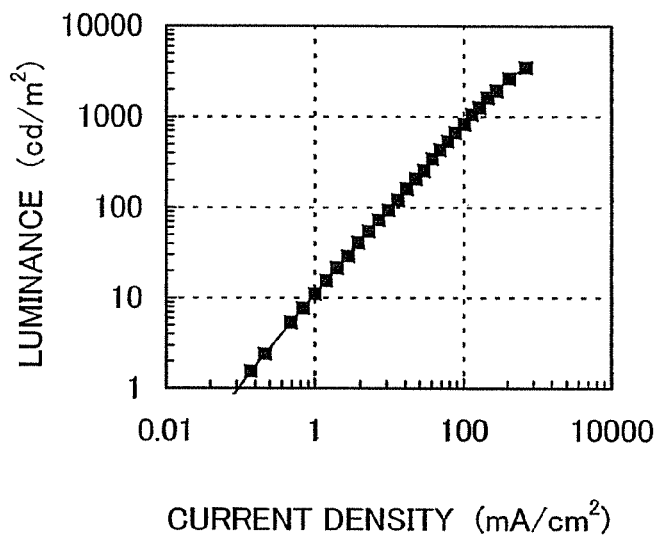
FIGS. 20A to 20C are graphs showing operation characteristics of a light emitting element formed in Embodiment 5.
Figure 20B:
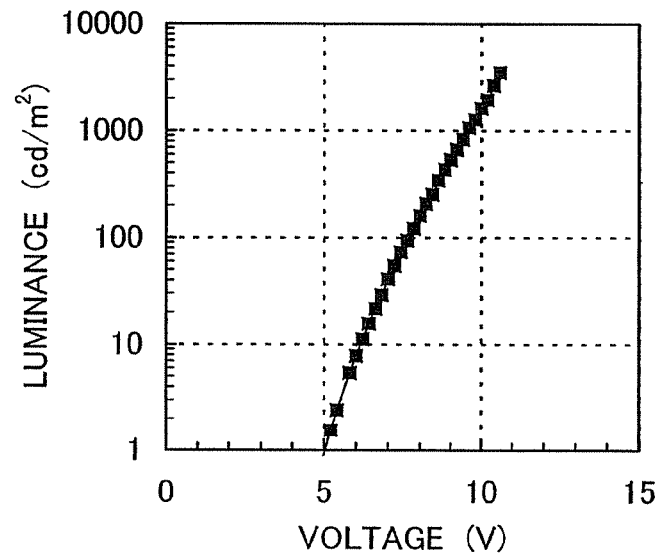
Figure 20C:
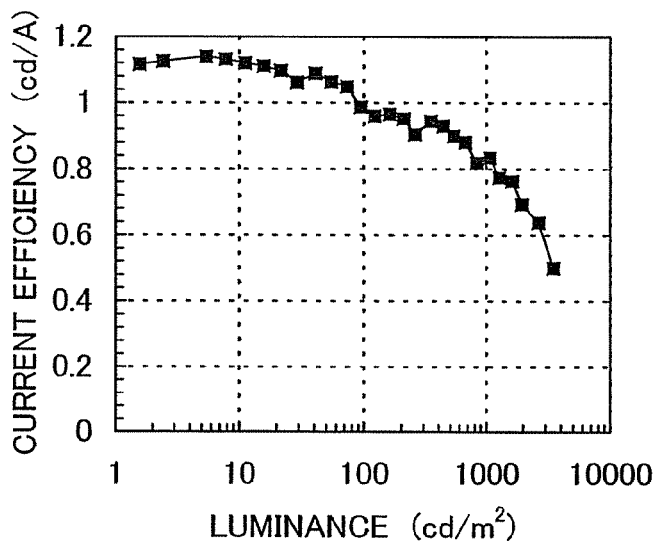

The obtained light emitting element was sealed under a nitrogen atmosphere using a sealant, without being exposed to the atmosphere. Voltage was applied to the light emitting element formed in this embodiment so that electric potential of the first electrode 701 was higher than that of the second electrode 702, and operation characteristics of the light emitting element was measured. Note that the measurement was conducted at room temperature (in the condition kept at 25° C.). The results are shown in FIGS. 20A to 20C. FIG. 20A shows current density-luminance characteristics, FIG. 20B shows voltage-luminance characteristics, and FIG. 20C shows luminance-current efficiency characteristics. In FIG. 20A, the horizontal axis indicates a current density (mA/cm²), and the vertical axis indicates luminance (cd/m²). In FIG. 20B, the horizontal axis indicates voltage (V), and the vertical axis indicates luminance (cd/m²). In FIG. 20C, the horizontal axis indicates luminance (cd/m²), and the vertical axis indicates current efficiency (cd/A).

According to the results, the light emitting element formed in this embodiment emitted light with luminance of 540 cd/m² when a voltage of 9.0V was applied, and current density at that time was 59.6 mA/cm². In addition, current efficiency at that time was 0.90 cd/A.

Figure 21:
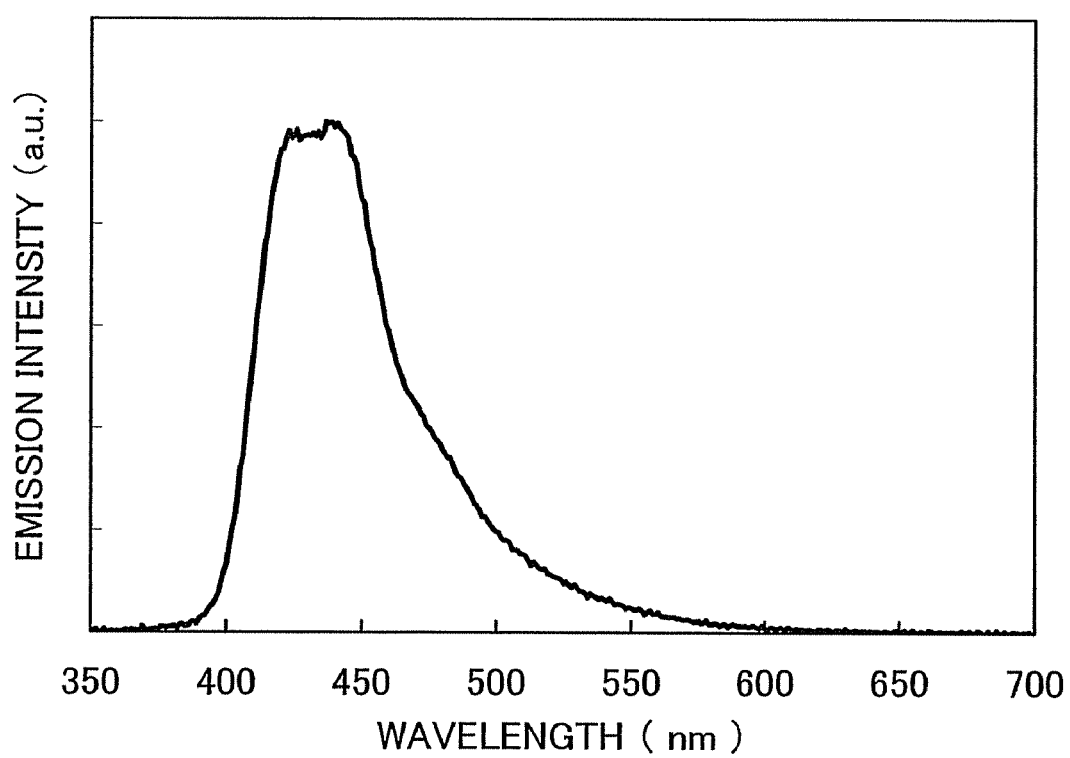
FIG. 21 is a graph showing an emission spectrum of the light emitting element formed in Embodiment 5.

An emission spectrum of the light emitting element formed in this embodiment is shown in FIG. 21. In FIG. 21, the horizontal axis indicates a wavelength (nm) and the vertical axis indicates intensity (arbitrary unit). According to FIG. 21, it is found that the light emitting element formed in this embodiment has a light emission peak at 437 nm and exhibits blue light emission.

Further, a CIE chromaticity coordinate of light emission obtained when a voltage of 9.0 V was applied was (x, y)=(0.15, 0.07). Since chromaticity coordinate of blue in NTSC standard is (x, y)=(0.14, 0.08), it is found that the light emitting element in this embodiment exhibits blue light with excellent color purity close to NTSC standard.

Embodiment 6

In this embodiment, a manufacturing method of a light emitting element in which (E)-4,4'-bis[4-(carbazol-9-yl)phenyl]stilbene (abbr.: CzP₂S), which is synthesized in Synthesis Example 1, is used in a light emitting layer, and operation characteristics of the light emitting element are described with reference to FIG. 19. Note that a structure of the light emitting layer is different from that in Embodiment 5.

First, ITSO was deposited over the glass substrate 700 by a sputtering method to be the first electrode 701.

Then, the glass substrate 700, over which the first electrode 701 was formed, was fixed to a substrate holder in a vacuum evaporation apparatus in a manner such that the surface on which the first electrode 701 was formed faced downward. Then, the hole injecting layer 711 was formed by depositing NPB and molybdenum trioxide by co-evaporation to have a thickness of 50 nm on the first electrode 701. Note that a mass ratio of NPB to molybdenum trioxide was set to be 4:1 (=NPB:molybdenum trioxide).

Then, the hole transporting layer 712 was formed by depositing NPB on the hole injecting layer 711 by an evaporation method to have a thickness of 10 nm.

Then, the light emitting layer 713 was formed by depositing CzP₂S by an evaporation method on the hole transporting layer 712 to have a thickness of 30 nm.

The electron transporting layer 714 was formed by depositing BCP on the light emitting layer 713 to have a thickness of 10 nm. Note that an evaporation method was employed for the film formation.

The electron injecting layer 715 was formed by depositing Alq₃ and Li by co-evaporation on the electron transporting layer 714 to have a thickness of 20 nm. Note that a mass ratio of Alq₃ to Li was set to be 1:0.01 (=Alq₃:Li).

The second electrode 702 was formed by depositing aluminum by an evaporation method on the electron injecting layer 715.

In the foregoing manner, the light emitting element was formed by stacking the hole injecting layer 711, the hole transporting layer 712, the light emitting layer 713, the electron transporting layer 714, and the electron injecting layer 715, between the first electrode 701 and the second electrode 702.

Figure 22A:
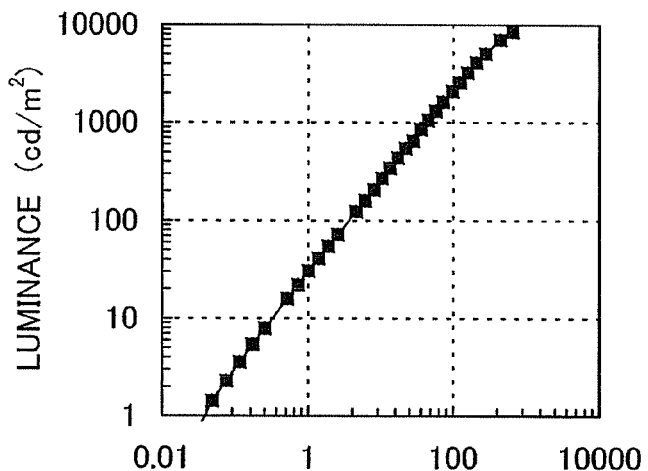
FIGS. 22A to 22C are graphs showing operation characteristics of a light emitting element formed in Embodiment 6.
Figure 22B:
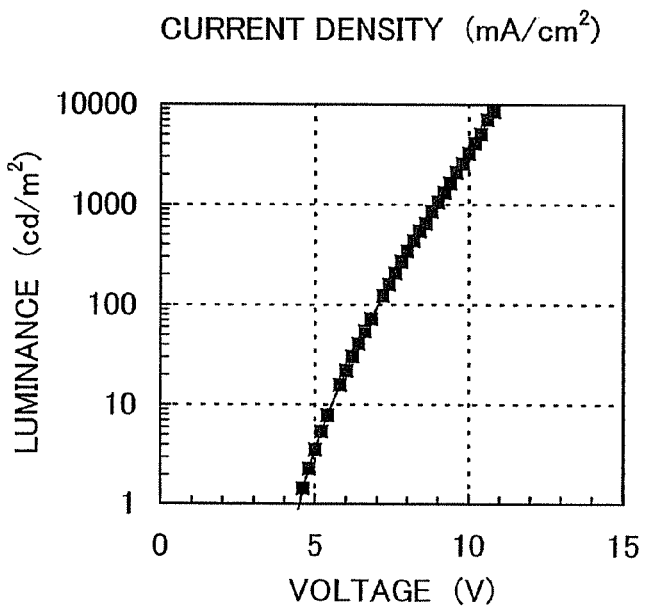
Figure 22C:
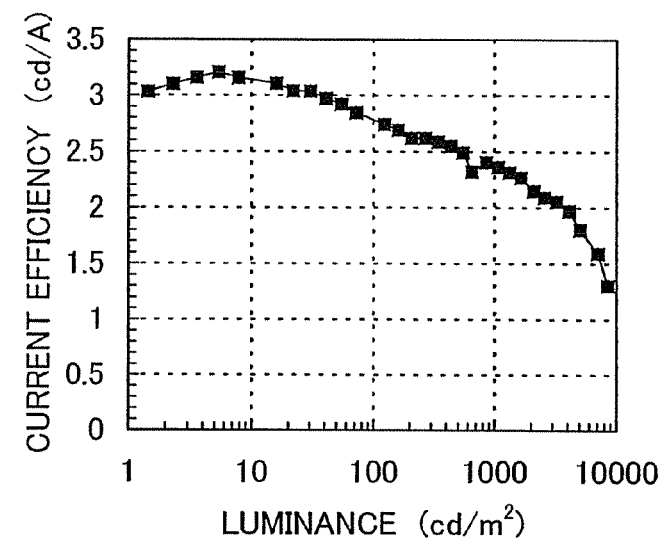

The obtained light emitting element was sealed under a nitrogen atmosphere using a sealant, without being exposed to the atmosphere. Voltage was applied to the light emitting element formed in this embodiment so that electric potential of the first electrode 701 was higher than that of the second electrode 702, and operation characteristics of the light emitting element was measured. Note that the measurement was conducted at room temperature (in the condition kept at 25° C.). The results are shown in FIGS. 22A to 22C. FIG. 22A shows current density-luminance characteristics, FIG. 22B shows voltage-luminance characteristics, and FIG. 22C shows luminance-current efficiency characteristics. In FIG. 22A, the horizontal axis indicates a current density (mA/ cm$^2$), and the vertical axis indicates luminance (cd/m$^2$). In FIG. 22B, the horizontal axis indicates voltage (V), and the vertical axis indicates luminance (cd/m$^2$). In FIG. 22C, the horizontal axis indicates luminance (cd/m$^2$), and the vertical axis indicates current efficiency (cd/A).

According to the results, the light emitting element formed in this embodiment emitted light with luminance of 550 cd/m$^2$ when a voltage of 8.4 V was applied, and current density at that time was 22.0 mA/cm$^2$. In addition, current efficiency at that time was 2.5 cd/A.

Figure 23:
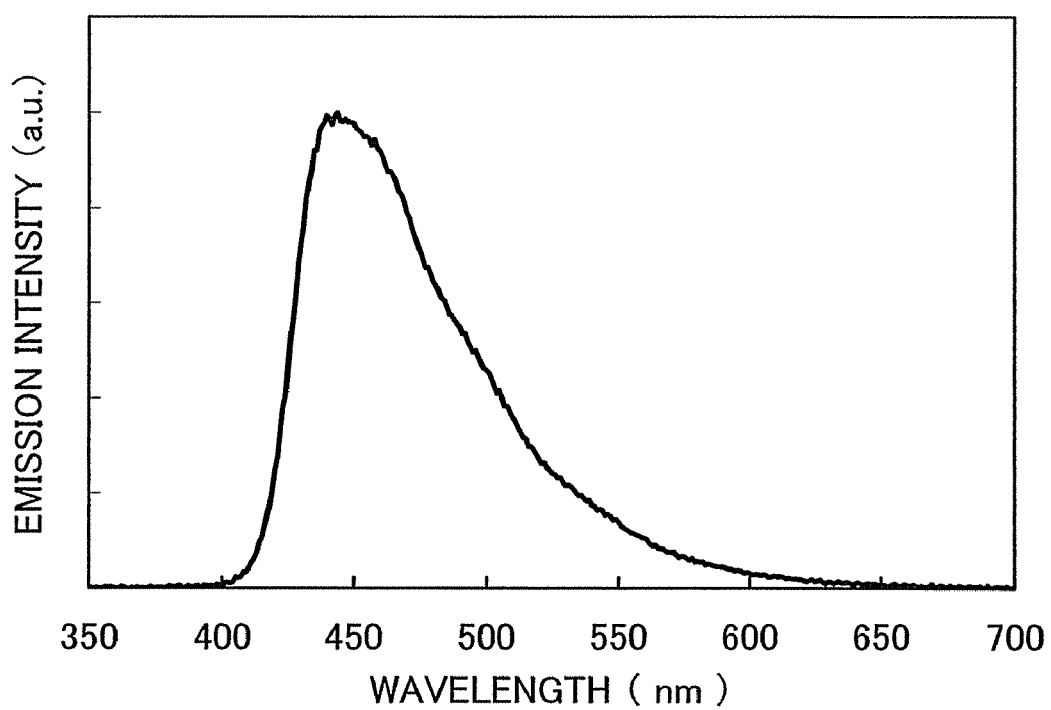
FIG. 23 is a graph showing an emission spectrum of the light emitting element formed in Embodiment 6.

An emission spectrum of the light emitting element formed in this embodiment is shown in FIG. 23. In FIG. 23, the horizontal axis indicates a wavelength (nm) and the vertical axis indicates intensity (arbitrary unit). According to FIG. 23, it is found that the light emitting element in this embodiment has a light emission peak at 444 nm and exhibits blue light emission.

Further, a CIE chromaticity coordinate of light emission obtained when a voltage of 8.4 V was applied was (x, y)= (0.16, 0.14). As described in this embodiment, it is found that, in the case where CzP$_2$S, which is a stilbene derivative of the present invention, is applied to a light emitting element, a light emitting element which exhibits blue light emission with excellent color purity can also be obtained even when a light emitting layer is formed of only CzP$_2$S.

Embodiment 7

In this embodiment, a manufacturing method of a light emitting element in which (E)-4,4'-bis(9-phenylcarbazol-3-yl)stilbene (abbr.: PCz$_2$S), which is synthesized in Synthesis Example 2, is used in a light emitting layer, and operation characteristics of the light emitting element are described with reference to FIG. 19.

First, ITSO was deposited over the glass substrate 700 by a sputtering method to be the first electrode 701.

Then, the glass substrate 700, over which the first electrode 701 was formed, was fixed to a substrate holder in a vacuum evaporation apparatus in a manner such that the surface on which the first electrode 701 was formed faced downward. Then, the hole injecting layer 711 was formed by depositing DNTPD and molybdenum trioxide by co-evaporation to have a thickness of 50 nm on the first electrode 701. Note that a mass ratio of DNTPD to molybdenum trioxide was set to be 4:2 (=DNTPD:molybdenum trioxide). Note that the structural formula (111) of DNTPD is shown below.

Then, the hole transporting layer 712 was formed by depositing NPB on the hole injecting layer 711 by an evaporation method to have a thickness of 10 mm.

Then, the light emitting layer 713 was formed by depositing CBP and PCz$_2$S by co-evaporation on the hole transporting layer 712 to have a thickness of 30 nm. Note that a mass ratio of CBP to PCz$_2$S was set to be 1:0.05 (=CBP:PCz$_2$S). Thus, PCz$_2$S was in a state of being dispersed in a layer formed of CBP.

The electron transporting layer 714 was formed by depositing BCP on the light emitting layer 713 to have a thickness of 10 nm. Note that an evaporation method was employed for the film formation.

The electron injecting layer 715 was formed by depositing Alq$_3$ and Li by co-evaporation on the electron transporting layer 714 to have a thickness of 20 nm. Note that a mass ratio of Alq$_3$ to Li was set to be 1:0.01 (=Alq$_3$:Li).

The second electrode 702 was formed by depositing aluminum by an evaporation method on the electron injecting layer 715.

In the foregoing manner, the light emitting element was formed by stacking the hole injecting layer 711, the hole transporting layer 712, the light emitting layer 713, the electron transporting layer 714, and the electron injecting layer 715, between the first electrode 701 and the second electrode 702.

Figure 24A:
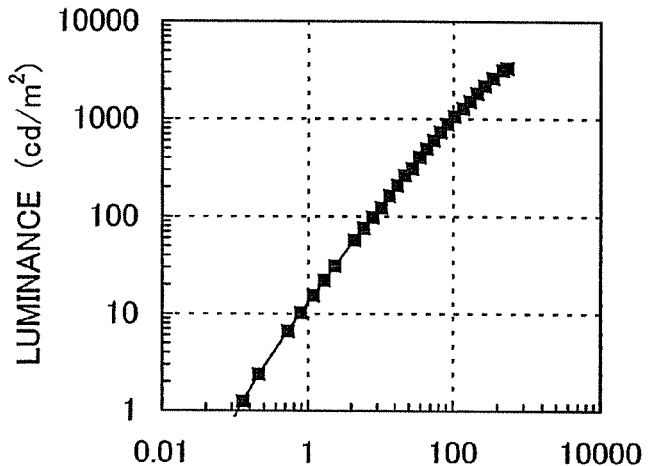
FIGS. 24A to 24C are graphs showing operation characteristics of a light emitting element formed in Embodiment 7.
Figure 24B:
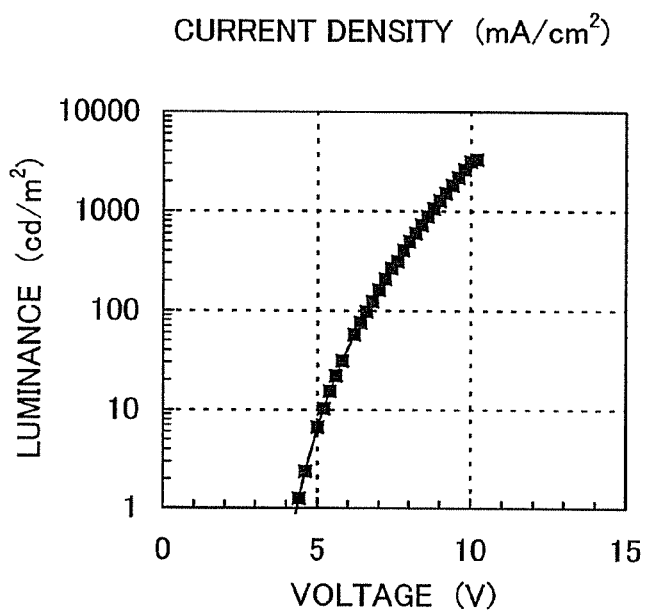
Figure 24C:
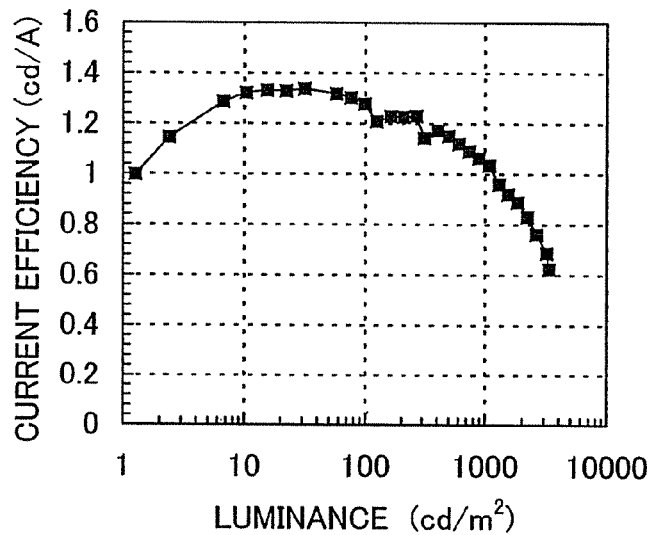

The obtained light emitting element was sealed under a nitrogen atmosphere using a sealant, without being exposed to the atmosphere. Voltage was applied to the light emitting element formed in this embodiment so that electric potential of the first electrode 701 was higher than that of the second electrode 702, and operation characteristics of the light emitting element was measured. Note that the measurement was conducted at room temperature (in the condition kept at 25° C.). The results are shown in FIGS. 24A to 24C. FIG. 24A shows current density-luminance characteristics, FIG. 24B shows voltage-luminance characteristics, and FIG. 24C shows luminance-current efficiency characteristics. In FIG. 24A, the horizontal axis indicates a current density (mA/cm$^2$), and the vertical axis indicates luminance (cd/m$^2$). In FIG. 24B, the horizontal axis indicates voltage (V), and the vertical axis indicates luminance (cd/m$^2$). In FIG. 24C, the horizontal axis indicates luminance (cd/m$^2$), and the vertical axis indicates current efficiency (cd/A).

According to the results, the light emitting element formed in this embodiment emitted light with luminance of 500 cd/m$^2$ when a voltage of 8.0 V was applied, and current

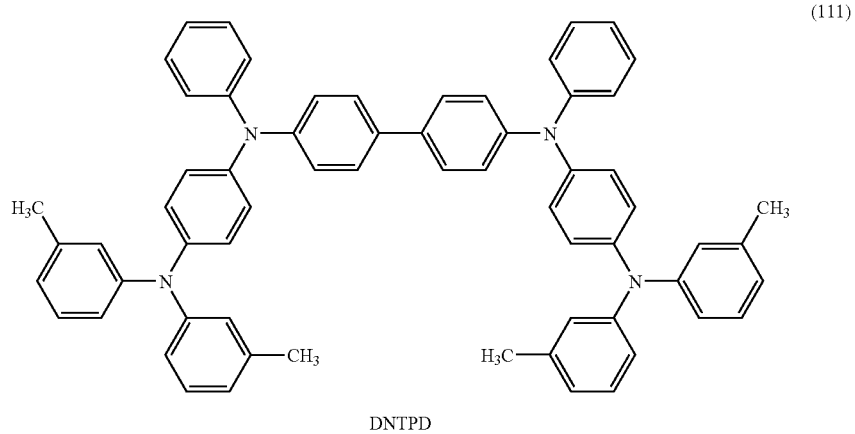

(111)

DNTPD density at that time was 43.4 mA/cm². In addition, current efficiency at that time was 1.2 cd/A.

Figure 25:
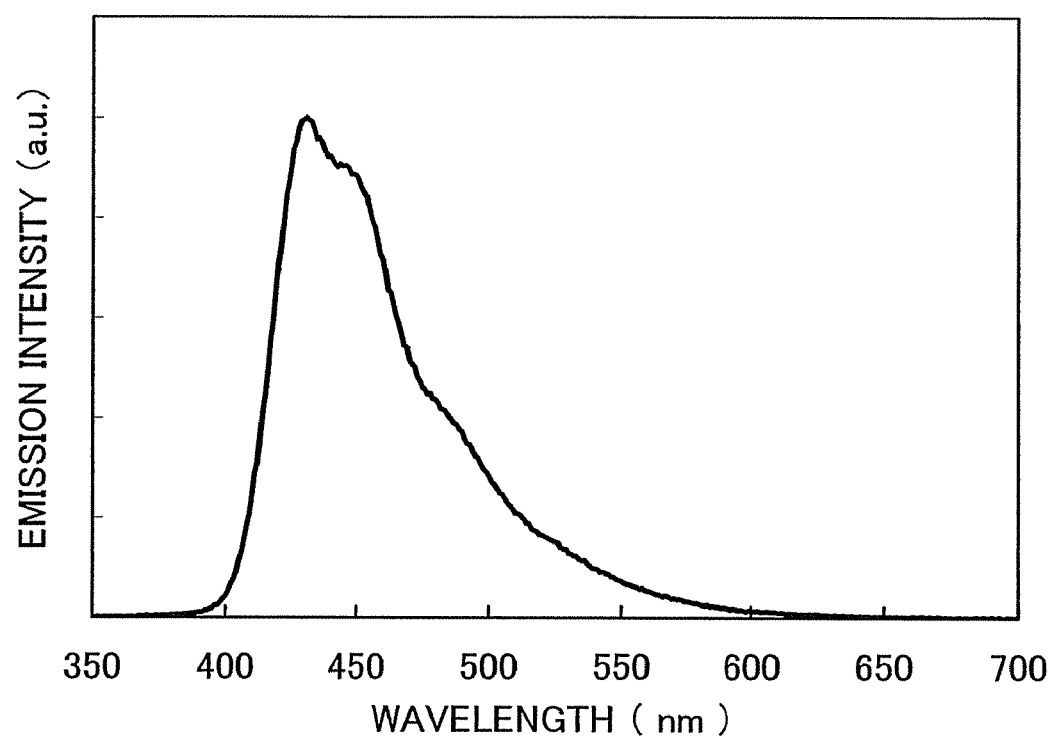
FIG. 25 is a graph showing an emission spectrum of the light emitting element formed in Embodiment 7.

An emission spectrum of the light emitting element formed in this embodiment is shown in FIG. 25. In FIG. 25, the horizontal axis indicates a wavelength (nm) and the vertical axis indicates intensity (arbitrary unit). According to FIG. 25, it is found that the light emitting element in this embodiment has a light emission peak at 431 nm and exhibits blue light emission. In addition, a CIE chromaticity coordinate of light emission obtained when a voltage of 8.0 V was applied was (x, y)=(0.15, 0.09). Since chromaticity coordinate of blue in NTSC standard is (x, y)=(0.14, 0.08), it is found that the light emitting element in this embodiment exhibits blue light with excellent color purity close to NTSC standard.

Embodiment 8

In this embodiment, a manufacturing method of a light emitting element in which (E)-4,4'-bis(9-phenylcarbazol-3-yl)stilbene (abbr.: PCz₂S), which is synthesized in Synthesis Example 2, is used in a light emitting layer, and operation characteristics of the light emitting element are described with reference to FIG. 19. Note that a structure of the light emitting layer is different from that in Embodiment 7.

First, ITSO was deposited over the glass substrate 700 by a sputtering method to be the first electrode 701.

Then, the glass substrate 700, over which the first electrode 701 was formed, was fixed to a substrate holder in a vacuum evaporation apparatus in a manner such that the surface on which the first electrode 701 was formed faced downward. Then, the hole injecting layer 711 was formed by depositing DNTPD and molybdenum trioxide by co-evaporation to have a thickness of 50 nm on the first electrode 701. Note that a mass ratio of DNTPD to molybdenum trioxide was set to be 4:2 (=DNTPD:molybdenum trioxide).

Then, the hole transporting layer 712 was formed by depositing NPB on the hole injecting layer 711 by an evaporation method to have a thickness of 10 nm.

Then, the light emitting layer 713 was formed by depositing PCz₂S by an evaporation method on the hole transporting layer 712 to have a thickness of 30 nm.

The electron transporting layer 714 was formed by depositing BCP on the light emitting layer 713 to have a thickness of 10 nm. Note that an evaporation method was employed for the film formation.

The electron injecting layer 715 was formed by depositing Alq₃ and Li by co-evaporation on the electron transporting layer 714 to have a thickness of 20 nm. Note that a mass ratio of Alq₃ to Li was set to be 1:0.01 (=Alq₃:Li).

The second electrode 702 was formed by depositing aluminum by an evaporation method on the electron injecting layer 715.

In the foregoing manner, the light emitting element was formed by stacking the hole injecting layer 711, the hole transporting layer 712, the light emitting layer 713, the electron transporting layer 714, and the electron injecting layer 715, between the first electrode 701 and the second electrode 702.

Figure 26A:
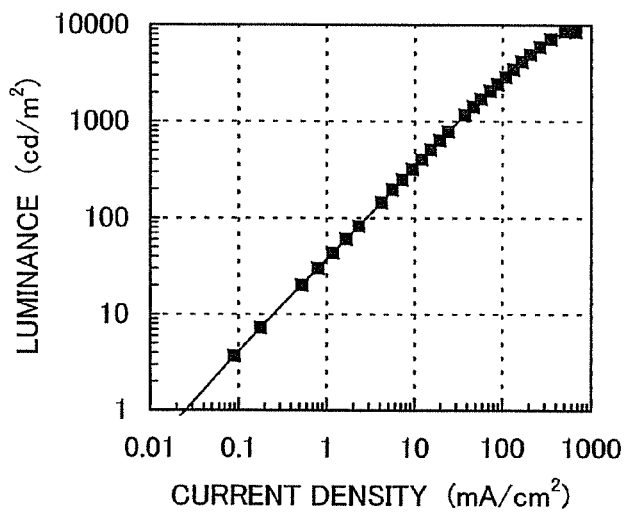
FIGS. 26A to 26C are graphs showing operation characteristics of a light emitting element formed in Embodiment 8.
Figure 26B:
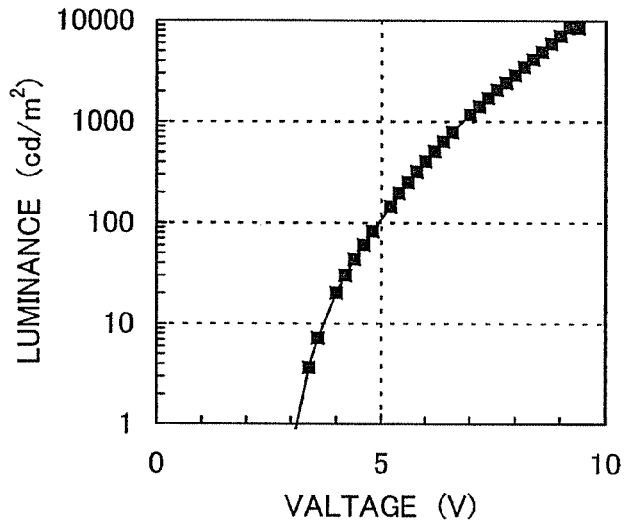
Figure 26C:
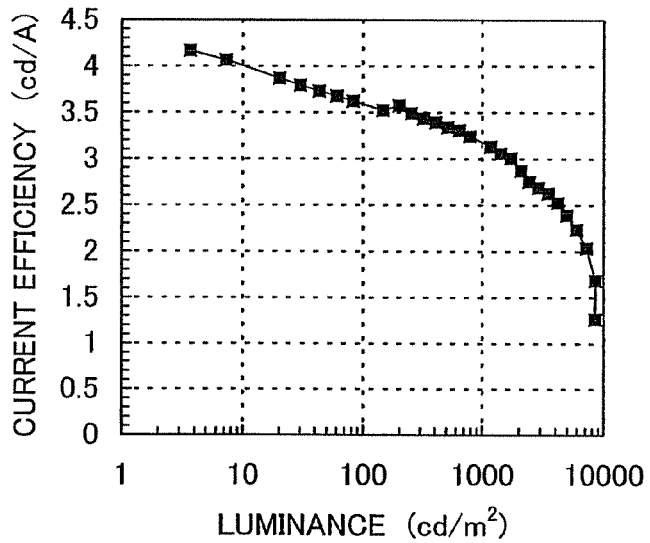

The obtained light emitting element was sealed under a nitrogen atmosphere using a sealant, without being exposed to the atmosphere. Voltage was applied to the light emitting element formed in this embodiment so that electric potential of the first electrode 701 was higher than that of the second electrode 702, and operation characteristics of the light emitting element was measured. Note that the measurement was conducted at room temperature (in the condition kept at 25° C.). The results are shown in FIGS. 26A to 26C. FIG. 26A shows current density-luminance characteristics, FIG. 26B shows voltage-luminance characteristics, and FIG. 26C shows luminance-current efficiency characteristics. In FIG. 26A, the horizontal axis indicates a current density (mA/cm²), and the vertical axis indicates luminance (cd/m²). In FIG. 26B, the horizontal axis indicates voltage (V), and the vertical axis indicates luminance (cd/m²). In FIG. 26C, the horizontal axis indicates luminance (cd/m²), and the vertical axis indicates current efficiency (cd/A).

According to the results, the light emitting element formed in this embodiment emitted light with luminance of 510 cd/m² when a voltage of 6.2 V was applied, and current density at that time was 15.3 mA/cm². In addition, current efficiency at that time was 3.3 cd/A.

Figure 27:
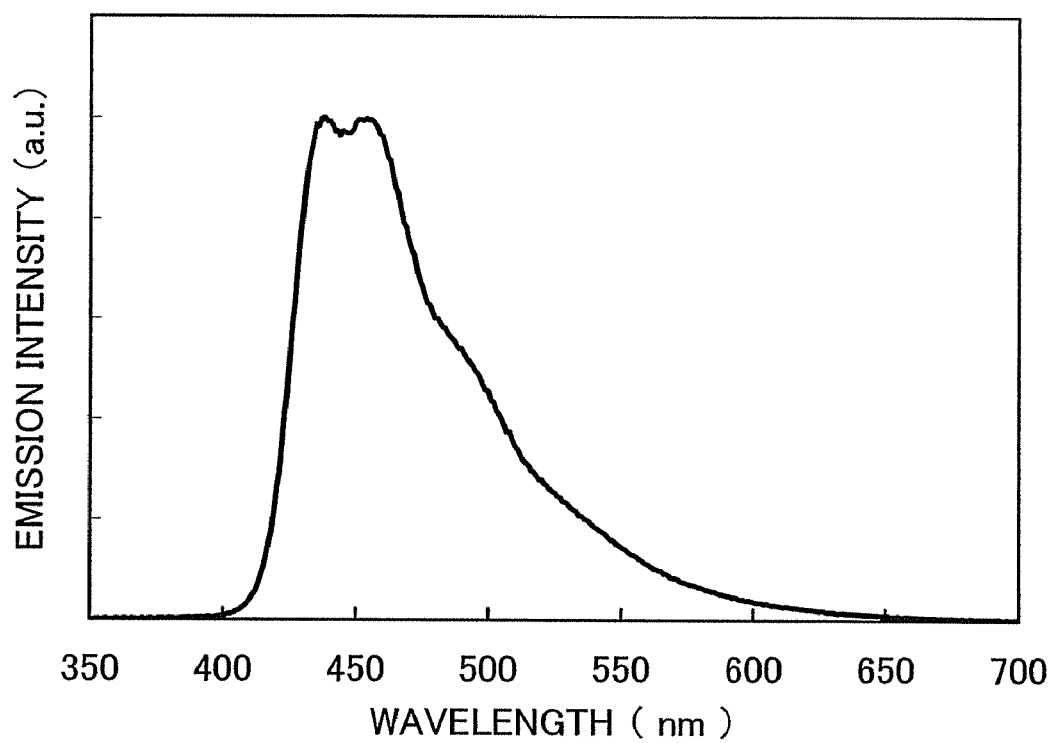
FIG. 27 is a graph showing an emission spectrum of the light emitting element formed in Embodiment 8

An emission spectrum of the light emitting element formed in this embodiment is shown in FIG. 27. In FIG. 27, the horizontal axis indicates a wavelength (nm) and the vertical axis indicates intensity (arbitrary unit). According to FIG. 27, it is found that the light emitting element in this embodiment has a light emission peak at 438 nm and exhibits blue light emission.

In addition, a CIE chromaticity coordinate of light emission obtained when a voltage of 6.2 V was applied was (x, y)=(0.16, 0.14). As described in this embodiment, it is found that, in the case where PCz₂S, which is a stilbene derivative of the present invention, is applied to a light emitting element, a light emitting element which exhibits blue light emission with excellent color purity can be obtained even when a light emitting layer is formed of only PCz₂S.

This application is based on Japanese Patent Application serial no. 2006-261336 filed in Japan Patent Office on Sep. 26, 2006, the entire contents of which are hereby incorporated by reference.

What is claimed is:

1. A stilbene derivative represented by a general formula (G1),

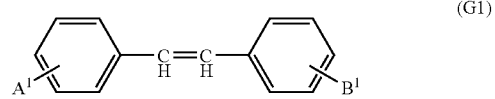

wherein each of A¹ and B¹ represents any one of structures represented by general formulae (G1-1) to (G1-4) shown below,

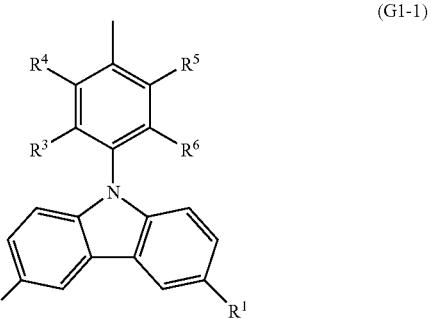

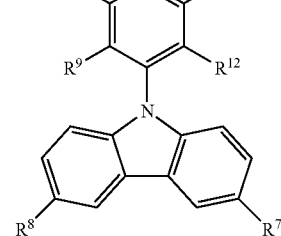

-continued (G1-3)

(G1-4)

wherein each of R$^1$ to R$^{24}$ represents any one of hydrogen and an alkyl group having 1 to 4 carbon atoms.

2. A light emitting device comprising:
an anode;
a cathode; and
a light emitting layer provided between the anode and the cathode,
wherein the light emitting layer comprises the stilbene derivative according to claim 1.

3. An electronic appliance comprising a light emitting device,
wherein the light emitting device comprises a light emitting layer interposed between an anode and a cathode, and
wherein the light emitting layer comprises the stilbene derivative according to claim 1.

4. A stilbene derivative according to claim 1 wherein A$^1$ and B$^1$ each are bonded to para positions of benzene rings of the stilbene derivative with respect to a double bond of the stilbene derivative.

5. A stilbene derivative represented by a general formula (G2), (G2)

wherein C$^1$ represents any one of structures represented by general formulae (G1-1) to (G1-4) shown below, and each of R$^{25}$ to R$^{27}$ represents any one of hydrogen and an alkyl group having 1 to 4 carbon atoms, (G1-1)

(G1-2)

(G1-3)

(G1-4)

wherein each of R$^1$ to R$^{24}$ represents any one of hydrogen and an alkyl group having 1 to 4 carbon atoms.

6. A light emitting device comprising:
an anode;
a cathode; and
a light emitting layer provided between the anode and the cathode,
wherein the light emitting layer comprises the stilbene derivative according to claim 5.

7. An electronic appliance comprising a light emitting device,
wherein the light emitting device comprises a light emitting layer interposed between an anode and a cathode, and wherein the light emitting layer comprises the stilbene derivative according to claim 5.

8. A stilbene derivative according to claim 5 wherein $C^1$ is bonded to para position of benzene ring of the stilbene derivative with respect to a double bond of the stilbene derivative.

9. A stilbene derivative represented by a general formula (G5),

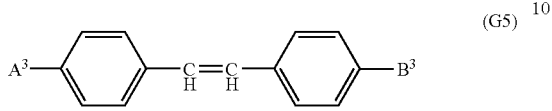
(G5)

wherein each of $A^3$ and $B^3$ represents any one of structures represented by general formulae (G2-1) and (G2-2) shown below, and

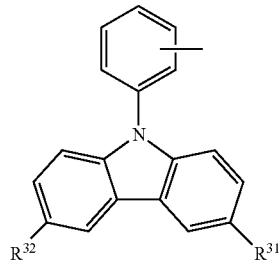
(G2-1)

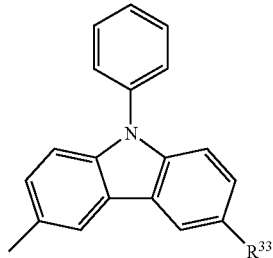
(G2-2)

wherein each of $R^{31}$ to $R^{33}$ represents any one of hydrogen and an alkyl group having 1 to 4 carbon atoms.

10. A light emitting device comprising:
an anode;
a cathode; and
a light emitting layer provided between the anode and the cathode,
wherein the light emitting layer comprises the stilbene derivative according to claim 9.

11. An electronic appliance comprising a light emitting device,
wherein the light emitting device comprises a light emitting layer interposed between an anode and a cathode, and
wherein the light emitting layer comprises the stilbene derivative according to claim 9.

* * * * *

UNITED STATES PATENT AND TRADEMARK OFFICE
CERTIFICATE OF CORRECTION

PATENT NO. : 7,758,972 B2  
APPLICATION NO. : 11/856160  
DATED : July 20, 2010  
INVENTOR(S) : Masakazu Egawa, Sachiko Kawakami and Nobuharu Ohsawa Page 1 of 1

It is certified that error appears in the above-identified patent and that said Letters Patent is hereby corrected as shown below:

Column 67, Line 43; Change "dibenzo[fh]" to --dibenzo[f, h]--.

Column 76, Line 52; Change "receive" to --receiver--.

Column 79, Line 60; Change "shown Fig. 7B" to --shown in FIG. 7B--.

Column 94, Line 3; Change "10 mm" to --10 nm--.

Signed and Sealed this  
Twenty-ninth Day of May, 2012

David J. Kappos  
*Director of the United States Patent and Trademark Office*